(12) United States Patent
Graupe et al.

(10) Patent No.: US 7,488,848 B2
(45) Date of Patent: Feb. 10, 2009

(54) ALPHA KETOAMIDE COMPOUNDS AS CYSTEINE PROTEASE INHIBITORS

(75) Inventors: Michael Graupe, Pacifica, CA (US); John O. Link, San Francisco, CA (US); Michael G. Roepel, San Francisco, CA (US)

(73) Assignee: Virobay, Inc., Menlo Park, CA (US)

( * ) Notice: Subject to any disclaimer, the term of this patent is extended or adjusted under 35 U.S.C. 154(b) by 448 days.

(21) Appl. No.: 11/384,023

(22) Filed: Mar. 17, 2006

(65) Prior Publication Data

US 2007/0021353 A1    Jan. 25, 2007

Related U.S. Application Data

(60) Provisional application No. 60/684,623, filed on May 24, 2005, provisional application No. 60/663,970, filed on Mar. 21, 2005.

(51) Int. Cl.
*C07C 233/05* (2006.01)
*A61K 31/65* (2006.01)

(52) U.S. Cl. .................. 564/152; 564/154; 546/333; 514/357; 514/616

(58) Field of Classification Search ............... 564/152, 564/154; 546/333; 514/357, 616
See application file for complete search history.

(56) References Cited

U.S. PATENT DOCUMENTS

| | | | |
|---|---|---|---|
| 6,420,364 B1 | 7/2002 | Emmanuel et al. |
| 6,506,733 B1 | 1/2003 | Buysse et al. |
| 6,730,671 B2 | 5/2004 | Cywin et al. |
| 2003/0092634 A1 | 5/2003 | Buysse et al. |
| 2004/0127426 A1 | 7/2004 | Graupe et al. |
| 2005/0014941 A1 | 1/2005 | Black et al. |
| 2005/0182096 A1 | 8/2005 | Link et al. |
| 2005/0240023 A1 | 10/2005 | Bayly et al. |
| 2006/0111440 A1 | 5/2006 | Gauthier et al. |

FOREIGN PATENT DOCUMENTS

| | | |
|---|---|---|
| EP | 0 623 627 | 11/1994 |
| WO | WO 99/24460 A3 | 5/1999 |
| WO | WO/00/51998 | 9/2000 |
| WO | WO 00/55125 A2 | 9/2000 |
| WO | WO/00/55144 | 9/2000 |
| WO | WO/01/19796 | 3/2001 |
| WO | WO/01/19816 | 3/2001 |
| WO | WO 01/49288 A1 | 7/2001 |
| WO | WO 01/68645 A2 | 9/2001 |
| WO | WO 02/20485 A1 | 3/2002 |
| WO | WO/02/069901 | 9/2002 |
| WO | WO 02/074904 A2 | 9/2002 |
| WO | WO 02/098850 A2 | 12/2002 |
| WO | WO/03/024924 | 3/2003 |
| WO | WO/03/029200 | 4/2003 |
| WO | WO 03/075836 A2 | 9/2003 |
| WO | WO/03/097617 | 11/2003 |
| WO | WO 03/097617 A1 | 11/2003 |
| WO | WO 2004/083182 A1 | 3/2004 |
| WO | WO/2004/033445 | 4/2004 |
| WO | WO/2004/108661 | 12/2004 |
| WO | WO 2005/021487 A1 | 3/2005 |
| WO | WO 2005/028429 A2 | 3/2005 |
| WO | WO/2005/028454 | 3/2005 |
| WO | WO 2005/040142 | 5/2005 |
| WO | WO/2005/058348 | 6/2005 |
| WO | WO/2005/063742 | 7/2005 |
| WO | WO/2005/074904 | 8/2005 |
| WO | WO/2006/034004 | 3/2006 |

OTHER PUBLICATIONS

Bundgaard, et al. "A Novel Solution-Stable, Water-Soluble Prodrug Type for Drugs Containing a Hydroxyl or an NH-Acidic Group," J. Med. Chem., 19898, vol. 32, No. 12, pp. 2503-2507.
Greenspan, et al. Identification of Dipeptidyl Nitriles as Potent and Selective Inhibitors of Cathepsin B through Structure-Based Drug Design, J. Med. Chem., 2001, vol. 44, pp. 4524-4534.
Gong, Y., et al., "Convenient Substitution of Hydroxypyridines with Trifluoroacetaldehyde Ethyl Hemiacetal," Journal of Heterocyclic Chemistry 2001, vol. 38, No. 1, p. 25-28.
Volonterio, et al., "Solution/solid-phase synthesis of partially modified retro-ψ [NHCH(CF$_3$)]- peptidyl hydroxamates", Tetrahedron Letters, 2001, vol. 42, pp. 3141-3144.

*Primary Examiner*—Shailendra Kumar
(74) *Attorney, Agent, or Firm*—Townsend and Townsend and Crew LLP

(57) ABSTRACT

The present invention is directed to compounds that are inhibitors of cysteine proteases, in particular, cathepsins B, K, L, F, and S and are therefore useful in treating diseases mediated by these proteases. The present invention is directed to pharmaceutical compositions comprising these compounds and processes for preparing them.

44 Claims, No Drawings

ALPHA KETOAMIDE COMPOUNDS AS CYSTEINE PROTEASE INHIBITORS

CROSS-REFERENCES TO RELATED APPLICATIONS

This application claims the benefit of Provisional Patent Application No. 60/663,970, filed Mar. 21, 2005 and Provisional Patent Application No. 60/684,623, filed May 24, 2005, both of which are incorporated herein by reference.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

FIELD OF THE INVENTION

The present invention is directed to compounds that are inhibitors of cysteine proteases, in particular, cathepsins B, K, L, F, and S and are therefore useful in treating diseases mediated by these proteases. The present invention is also directed to pharmaceutical compositions comprising these compounds and processes for preparing them.

STATE OF THE ART

Cysteine proteases represent a class of peptidases characterized by the presence of a cysteine residue in the catalytic site of the enzyme. Cysteine proteases are associated with the normal degradation and processing of proteins. The aberrant activity of cysteine proteases, e.g., as a result of increased expression or enhanced activation, however, may have pathological consequences. In this regard, certain cysteine proteases are associated with a number of disease states, including arthritis, muscular dystrophy, inflammation, tumor invasion, glomerulonephritis, malaria, periodontal disease, metachromatic leukodystrophy and others. For example, increased cathepsin B levels and redistribution of the enzyme are found in tumors; thus, suggesting a role for the enzyme in tumor invasion and metastasis. In found in tumors; thus, suggesting a role for the enzyme in tumor invasion and metastasis. In addition, aberrant cathepsin B activity is implicated in such disease states as rheumatoid arthritis, osteoarthritis, pneumocystis carinii, acute pancreatitis, inflammatory airway disease and bone and joint disorders.

The prominent expression of cathepsin K in osteoclasts and osteoclast-related multinucleated cells and its high collagenolytic activity suggest that the enzyme is involved in osteoclast-mediated bone resorption and, hence, in bone abnormalities such as occurs in osteoporosis. In addition, cathepsin K expression in the lung and its elastinolytic activity suggest that the enzyme plays a role in pulmonary disorders as well.

Cathepsin L is implicated in normal lysosomal proteolysis as well as in several disease states, including, but not limited to, metastasis of melanomas. Cathepsin S is implicated in Alzheimer's disease and certain autoimmune disorders, including, but not limited to juvenile onset diabetes, multiple sclerosis, pemphigus vulgaris, Graves' disease, myasthenia gravis, systemic lupus erythemotasus, rheumatoid arthritis, neuropathic pain, and Hashimoto's thyroiditis. In addition, cathepsin S is implicated in: allergic disorders, including, but not limited to asthma; and allogeneic immune reponses, including, but not limited to, rejection of organ transplants or tissue grafts.

In view of the number of diseases wherein it is recognized that an increase in cysteine protease activity contributes to the pathology and/or symptomatology of the disease, molecules which inhibit the activity of this class of enzymes, in particular molecules which inhibit cathepsins B, K, L, F, and/or S, will therefore be useful as therapeutic agents.

SUMMARY OF THE INVENTION

In one aspect, this invention is directed to a compound of Formula (I):

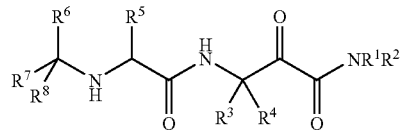

where:
$R^1$ is hydrogen or alkyl;
$R^2$ is cycloalkyl, cycloalkylalkyl, aralkyl, heteroaryl, or heteroaralkyl optionally substituted with one or two substitutents independently selected from alkyl, alkoxy, or halo;
$R^3$ is hydrogen, alkyl or alkoxyalkyl;
$R^4$ is alkyl; or
$R^3$ and $R^4$ together with the carbon atom to which they are attached form cycloalkylene optionally substituted with one to four fluoro or heterocycloalkylene optionally substituted with alkyl, alkoxyalkyl, hydroxyalkyl, acyl, cycloalkyl, cycloalkylalkyl, or haloalkyl;
$R^5$ is alkyl, haloalkyl optionally substituted with cycloalkyl, aryl, heteroaryl, or heterocycloalkyl, cycloalkylalkyl, aralkyl, heteroaralkyl, heterocycloalkylalkyl, -(alkylene)-X—$R^9$ (where X is —O—, —S—, —SO—, —SO$_2$—, —CONH—, —NHCO—, or —NHSO$_2$— and $R^9$ is alkyl, haloalkyl, cycloalkyl, cycloalkylalkyl, aryl, aralkyl, heteroaryl, heteroaralkyl, heterocycloalkyl, or heterocycloalkylalkyl), or -(alkylene)-$X^1$-(haloalkylene)-$R^{10}$ (where $X^1$ is —O—, —S—, —SO—, —SO$_2$—, —CONH—, —NHCO—, or —NHSO$_2$— and $R^{10}$ is cycloalkyl, aryl, heteroaryl, or heterocycloalkyl), wherein the aromatic or alicyclic ring in $R^5$ is optionally substituted with one, two, or three $R^a$ independently selected from alkyl, haloalkyl, alkoxy, hydroxy, haloalkoxy, cyano, halo, carboxy, or alkoxycarbonyl; or optionally substituted with one or two $R^b$ independently selected from hydrogen, alkyl, haloalkyl, alkoxy, hydroxy, haloalkoxy, halo, carboxy, or alkoxycarbonyl and one $R^c$ selected from hydroxyalkyl, alkoxyalkyl, aminoalkyl, aryl, heteroaryl, aralkyl, heteroaralkyl, cycloalkyl, cycloalkylalkyl, heterocycloalkyl, heterocycloalkylalkyl, acyl, acylalkyl, aryloxycarbonyl, aralkyloxycarbonyl, heteroaryloxycarbonyl, heteroaralkyloxycarbonyl, heterocycloalkyloxycarbonyl, cycloalkyloxycarbonyl, aryloxy, heteroaryloxy, aralkyloxy, heteroaralkyloxy, aminocarbonyl, aminosulfonyl, or —SO$_2R^{11}$ (where $R^{11}$ is alkyl, cycloalkyl, aryl, heteroaryl, or heterocycloalkyl); and further wherein the aromatic or alicyclic ring in $R^c$ is optionally substituted with one, two, or three $R^d$ independently selected from alkyl, alkylsulfonyl, haloalkyl, alkoxy, hydroxy, haloalkoxy, or halo;

$R^6$ is haloalkyl;

$R^7$ is hydrogen, alkyl, or haloalkyl; and $R^8$ is hydrogen, alkyl, haloalkyl, cycloalkyl, aryl, heteroaryl, heterocycloalkyl attached via a carbon atom wherein the aromatic or alicyclic ring in $R^8$ is optionally substituted with one, two, or three $R^e$ independently selected from alkyl, halo, haloalkyl, hydroxy, alkoxy, haloalkoxy, alkylcarbonyl, alkoxycarbonyl, carboxy, cyano, alkylsulfonyl, alkylsulfonylamino, aminocarbonyl, or aminosulfonyl; or a pharmaceutically acceptable salts thereof.

In a second aspect, this invention is directed to a pharmaceutical composition comprising a compound of Formula (I) or a pharmaceutically acceptable salt thereof in admixture with one or more suitable excipients.

In a third aspect, this invention is directed to a method for treating a disease in an animal mediated by cysteine proteases, in particular cathepsin S, which method comprises administering to the animal a pharmaceutical composition comprising a therapeutically effective amount of a compound of Formula (I) or a pharmaceutically acceptable salt thereof in admixture with one or more suitable excipients.

In a fourth aspect, this invention is directed to processes for preparing compounds of Formula (I).

In a fifth aspect, this invention is directed to a method of treating a patient undergoing a therapy wherein the therapy causes an immune response, preferably a deleterious immune response, in the patient comprising administering to the patient a compound of Formula (I) or a pharmaceutically acceptable salt thereof. Preferably, the immune response is mediated by MHC class II molecules. The compound of this invention can be administered prior to, simultaneously, or after the therapy. Preferably, the therapy involves treatment with a biologic. Preferably, the therapy involves treatment with a small molecule.

Preferably, the biologic is a protein, preferably an antibody, more preferably a monoclonal antibody. More preferably, the biologic is Remicade®, Refacto®, Referon-A®, Factor VIII, Factor VII, Betaseron®, Epogen®, Enbrel®, Interferon beta, Botox®, Fabrazyme®, Elspar®, Cerezyme®, Myobloc®, Aldurazyme®, Verluma®, Interferon alpha, Humira®, Aranesp®, Zevalin® or OKT3.

Preferably, the treatment involves use of heparin, low molecular weight heparin, procainamide or hydralazine.

In a sixth aspect, this invention is directed to a method of treating immune response in an animal that is caused by administration of a biologic to the animal which method comprises administering to the animal in need of such treatment a therapeutically effective amount of a compound of Formula (I) or a pharmaceutically acceptable salt thereof.

In a seventh aspect, this invention is directed to a method of conducting a clinical trial for a biologic comprising administering to an individual participating in the clinical trial a compound of Formula (I) or a pharmaceutically acceptable salt thereof with the biologic.

In an eigth aspect, this invention is directed to a method of prophylactically treating a patient undergoing treatment with a biologic with a compound of Formula (I) or a pharmaceutically acceptable salt thereof to treat the immune response caused by the biologic in the patient.

In a ninth aspect, this invention is directed to a method of determing the loss in the efficacy of a biologic in an animal due to the immune response caused by the biologic comprising administering the biologic to the animal in the presence and absence of a compound of Formula (I) or a pharmaceutically acceptable salt thereof.

In a tenth aspect, this invention is directed to a method of improving efficacy of a biologic in an animal comprising administering the biologic to the animal with a compound of Formula (I) or a pharmaceutically acceptable salt thereof.

In an eleventh aspect, this invention is directed to the use of a compound of Formula (I) or a pharmaceutically acceptable salt thereof for the manufacture of a medicament. Preferably, the medicament is for use in the treatment of a disease mediated by Cathepsin S.

In a twelfth aspect, this invention is directed to the use of a compound of Formula (I) or a pharmaceutically acceptable salt thereof for the manufacture of a medicament for combination therapy with a biologic, wherein the compound of this invention treats the immune response caused by the biologic. Preferably, the compound(s) of the invention is administered prior to the administration of the biological agent. Preferably, the compound(s) of the invention is administered concomitantly with the biological agent. Preferably, the compound(s) of the invention is administered after the administration of the biological agent.

DETAILED DESCRIPTION OF THE INVENTION

Definitions:

Unless otherwise stated, the following terms used in the specification and claims are defined for the purposes of this Application and have the following meanings.

"Alicyclic" means a moiety characterized by arrangement of the carbon atoms in closed non-aromatic ring structures e.g., cycloalkyl and heterocycloalkyl rings as defined herein.

"Alkyl" represented by itself means a straight or branched, saturated aliphatic radical containing one to eight carbon atoms, unless otherwise indicated e.g., alkyl includes methyl, ethyl, propyl, isopropyl, butyl, sec-butyl, isobutyl, tert-butyl, and the like.

"Alkylene", unless indicated otherwise, means a straight or branched, saturated aliphatic, divalent radical having the number of one to six carbon atoms, e.g., methylene (—$CH_2$—), ethylene (—$CH_2CH_2$—), trimethylene (—$CH_2CH_2CH_2$—), tetramethylene (—$CH_2CH_2CH_2CH_2$—) 2-methyltetramethylene (—$CH_2CH(CH_3)CH_2CH_2$—), pentamethylene (—$CH_2CH_2CH_2CH_2CH_2$—), and the like.

"Alkylsulfonyl" means —$SO_2R$ radical where R is alkyl as defined herein e.g., methylsulfonyl, ethylsulfonyl, and the like.

"Alkylsulfonylamino" means —$NHSO_2R$ radical where R is alkyl as defined herein e.g., methylsulfonylamino, ethylsulfonylamino, and the like.

"Alkoxy" refers to a —OR radical where R is an alkyl group as defined above e.g., methoxy, ethoxy, and the like.

"Alkoxyalkyl" means a linear monovalent hydrocarbon radical of one to six carbon atoms or a branched monovalent hydrocarbon radical of three to six carbons substituted with at least one alkoxy group, preferably one or two alkoxy groups, as defined above, e.g., 2-methoxy-ethyl, 1-, 2-, or 3-methoxypropyl, 2-ethoxyethyl, and the like.

"Alkoxycarbonyl" refers to a —C(O)OR radical where R is an alkyl group as defined above e.g., methoxycarbonyl, ethoxycarbonyl, and the like.

"Aminoalkyl" means a linear monovalent hydrocarbon radical of one to six carbon atoms or a branched monovalent hydrocarbon radical of three to six carbons substituted with at least one, preferably one or two, —NRR' where R is hydrogen, alkyl, acyl, hydroxyalkyl, alkoxyalkyl, aryl, aralkyl, heteroaryl, heteroaralkyl or heterocycloalkylalkyl and R' is hydrogen, alkyl, hydroxyalkyl, alkoxyalkyl, aryl, aralkyl, heteroaryl, heteroaralkyl, heterocycloalkylalkyl, cycloalkyl, cycloalkylalkyl, aminocarbonyl, or aminosulfonyl as defined herein e.g., aminomethyl, methylaminoethyl, dimethylaminoethyl, 1,3-diaminopropyl, acetylaminopropyl, and the like.

"Acyl" refers to a —COR radical where R is hydrogen, alkyl, haloalkyl, cycloalkyl, aryl, aralkyl, heteroaryl, heteroaralkyl, or heterocycloalkyl as defined herein, e.g., formyl, acetyl, trifluoroacetyl, benzoyl, piperazin-1-ylcarbonyl, and the like. When R is alkyl it is referred to in this application as alkylcarbonyl.

"Acylalkyl" means a linear monovalent hydrocarbon radical of one to six carbon atoms or a branched monovalent hydrocarbon radical of three to six carbons substituted with at least one, preferably one or two, acyl group(s) as defined herein e.g., methylcarbonylmethyl, benzoylethyl, piperidin-1-ylcarbonylmethyl or ethyl, and the like.

"Aminocarbonyl" means —CONRR' radical where R and R' are independently selected from hydrogen, alkyl, aryl, aralkyl, heteroaryl, heteroaralkyl, or heterocycloalkylalkyl or R and R' together with the nitrogen atom to which they are attached form heterocycloamino as defined herein.

"Aminosulfonyl" means —SO$_2$NRR' radical where R and R' are independently selected from hydrogen, alkyl, aryl, aralkyl, heteroaryl, heteroaralkyl, or heterocycloalkylalkyl or R and R' together with the nitrogen atom to which they are attached form heterocycloamino as defined herein.

"Animal" includes humans, non-human mammals (e.g., dogs, cats, rabbits, cattle, horses, sheep, goats, swine, deer, and the like) and non-mammals (e.g., birds, and the like).

"Aromatic" refers to a moiety wherein the constituent atoms make up an unsaturated ring system, all atoms in the ring system are sp$^2$ hybridized and the total number of pi electrons is equal to 4n+2.

"Aryl" refers to a monocyclic or fused bicyclic ring assembly containing 6 to 10 ring carbon atoms wherein each ring is aromatic e.g., phenyl or naphthyl.

"Aryloxy" refers to a —O—R radical where R is aryl as defined above e.g., phenoxy, napthyloxy, and the like.

"Aryloxycarbonyl" refers to a —C(O)OR radical where R is aryl as defined above e.g., phenyloxycarbonyl, naphthyloxycarbonyl, and the like.

"Aralkyl" refers to a -(alkylene)-R radical where R is aryl as defined above e.g., benzyl, phenethyl, and the like.

"Aralkyloxy" refers to a —O—R radical where R is aralkyl as defined above e.g., benzyloxy, phenethyloxy, and the like.

"Aralkyloxycarbonyl" refers to a —C(O)OR radical where R is aralkyl as defined above e.g., benzyloxycarbonyl, phenethyloxycarbonyl, and the like.

"Biologic" means a therapeutic agent originally derived from living organisms for the treatment or management of a disease. Examples include, but are not limited to, proteins (recombinant and plasma derived), monoclonal or polyclonal, humanized or murine antibodies, toxins, hormones, and the like. Biologics are currently available for the treatment of a variety of diseases such as cancer, rheumatoid arthritis, and hemophilia.

"Carboxy" refers to —C(O)OH radical.

"Cycloalkyl" refers to a monovalent saturated monocyclic ring containing three to eight ring carbon atoms e.g., cyclopropyl, cyclobutyl, cyclopentyl, cyclohexyl, and the like.

"Cycloalkylalkyl" refers to a -(alkylene)-R radical where R is cycloalkyl as defined above e.g., cyclopropylmethyl, cyclobutylethyl, cyclobutylmethyl, and the like.

"Cycloalkyloxycarbonyl" refers to a —C(O)OR radical where R is cyccloalkyl as defined above e.g., cyclopropyloxycarbonyl, cyclopentyloxycarbonyl, and the like.

"Cycloalkylene" refers to a divalent saturated monocyclic ring containing three to eight ring carbon atoms. For example, the instance wherein "R$^3$ and R$^4$ together with the carbon atom to which both R$^1$ and R$^2$ are attached form cycloalkylene" includes, but is not limited to, the following:

, and the like.

"Disease" specifically includes any unhealthy condition of an animal or part thereof and includes an unhealthy condition that may be caused by, or incident to, medical or veterinary therapy applied to that animal, i.e., the "side effects" of such therapy.

"Derived" means a similar agent can be traced to.

"Deleterious immune response" means an immune response that prevents effective treatment of a patient or causes disease in a patient. As an example, dosing a patient with a murine antibody either as a therapy or a diagnostic agent causes the production of human antimouse antibodies that prevent or interfere with subsequent treatments. The incidence of antibody formation versus pure murine monoclonals can exceed 70%. (see Khazaeli, M. B. et al. *J. Immunother.* 1994, 15, pp 42-52; Dillman R. O. et al. *Cancer Biother.* 1994, 9, pp 17-28; and Reinsberg, J. *Hybridoma.* 1995, 14, pp 205-208). Additional examples of known agents that suffer from deleterious immune responses are blood-clotting factors such as factor VIII. When administered to hemophilia A patients, factor VIII restores the ability of the blood to clot. Although factor VIII is a human protein, it still elicits an immune response in hemophiliacs as endogenous factor VIII is not present in their blood and thus it appears as a foreign antigen to the immune system. Approximately 29-33% of new patients will produce antibodies that bind and neutralize the therapeutically administered factor VIII (see Lusher J. M. *Semin Thromb Hemost.* 2002, 28(3), pp 273-276). These neutralizing antibodies require the administration of larger amounts of factor VIII in order to maintain normal blood clotting parameters; an expensive regimen of treatment in order to induce immune tolerance (see Briet E et al. *Adv. Exp. Med. Bio.* 2001, 489, pp 89-97). Another immunogenic example is adenoviral vectors. Retroviral therapy remains experimental and is of limited utility. One reason is that the application of a therapeutic virus generates an immune response capable of blocking any subsequent administration of the same or similar virus (see Yiping Yang et al. *J. of Virology.* 1995, 69, pp 2004-2015). This ensures that retroviral therapies must be based on the transient expression of a protein or the direct incorporation of viral sequence into the host genome. Directed research has identified multiple viral neutralizing epitopes recognized by host antibodies (see Hanne, Gahery-Segard et al. *J. of Virology* 1998. 72, pp 2388-2397) suggesting that viral modifications will not be sufficient to overcome this obstacle. This invention will enable a process whereby an adenoviral therapy will have utility for repeated application. Another example of an immunogenic agent that elicits neutralizing antibodies is the well-known cosmetic agent Botox. Botulin toxin protein, is purified from the fermentation of *Clostridium botulinum*. As a therapeutic agent, it is used for muscle disorders such as cervical dystonia in addition to cosmetic application. After repeated exposure patients generate neutralizing antibodies to the toxin that results in reduced efficacy (see Birklein F. et al. *Ann Neurol.* 2002, 52, pp 68-73 and Rollnik, J. D. et al. *Neurol. Clin. Neurophysiol.* 2001, 2001(3), pp 2-4). A "deleterious immune response" also encompasses diseases caused by therapeutic agents. A specific example of this is the immune response to therapy with recombinant human erythropoietin (EPO). Erythropoietin is used to stimulate the growth or of red cells and restore red blood cell counts in patients who have undergone chemotherapy or dialysis. A small percentage of patients develop antibodies to EPO and subsequently are unresponsive to both therapeutically administered EPO and their own endogenous EPO (see Casadevall, N. et al., *NEJM.* 2002, 346, pp 469-475). They contract a disorder, pure red cell aplasia, in which red blood cell production is severely diminished (see Gershon S. K. et. al. *NEJM.* 2002, 346, pp 1584-1586). This complication of EPO therapy is lethal if untreated. Another specific example is the murine antibody, OKT3 (a.k.a., Orthoclone) a monoclonal antibody directed towards CD-3 domain of activated T-cells. In clinical trials 20-40% of patients administered OKT3 produce antibodies versus the therapy. These antibodies, besides neutralizing the therapy, also stimulate a strong host immune reaction. The immune reaction is severe enough that patients with high titers of human anti-mouse antibodies are specifically restricted from taking the drug (see Orthoclone package label). A final example is a human antibody therapeutic. Humira® is a monoclonal antibody directed against TNF and is used to treat rheumatoid arthritis patients. When taken alone ~12% of patients develop neutralizing antibodies. In addition, a small percentage of patients given the drug also contract a systemic lupus erthematosus-like condition that is an IgG-mediated immune response induced by the therapeutic agent (see Humira package label).

Another example of "deleterious immune response" is a host reaction to small molecule drugs. It is known to those skilled in the art that certain chemical structures will conjugate with host proteins to stimulate immune recognition (see Ju. C. et al. 2002. *Current Drug Metabolism* 3, pp 367-377 and Kimber I. et al. 2002, *Toxicologic Pathology* 30, pp 54-58.) A substantial portion of these host reactions are IgG mediated. Specific "deleterious immune responses" that are IgG mediated include: hemolytic anemia, Steven-Johnson syndrome and drug induced Lupus.

"Halo" refers to fluoro, chloro, bromo or iodo.

"Haloalkyl" refers to alkyl as defined above substituted by one or more, for example from one to thirteen, preferably from one to seven, "halo" atoms, as such terms are defined in this Application. Haloalkyl includes monohaloalkyl, dihaloalkyl, trihaloalkyl, perhaloalkyl and the like e.g. chloromethyl, dichloromethyl, difluoromethyl, trifluoromethyl, 2,2,2-trifluoroethyl, perfluoroethyl, 2,2,2-trifluoro-1,1-dichloroethyl, and the like.

"Haloalkylene" means alkylene radical as defined above wherein one to four, preferably one or two hydrogen atoms in the alkylene chain has(have) been replaced by fluorine atom (s).

"Haloalkoxy" refers to a —OR radical where R is haloalkyl group as defined above e.g., trifluoromethoxy, 2,2,2-trifluoroethoxy, difluoromethoxy, and the like.

"Heteroaryl" as a group or part of a group denotes an aromatic monocyclic or bicyclic moiety of 5 to 10 ring atoms in which one or more, preferably one, two, or three, of the ring atom(s) is(are) selected from nitrogen, oxygen or sulfur, the remaining ring atoms being carbon. Representative heteroaryl rings include, but are not limited to, pyrrolyl, furanyl, thienyl, oxazolyl, isoxazolyl, thiazolyl, imidazolyl, triazolyl, tetrazolyl, pyridinyl, pyrimidinyl, pyrazinyl, pyridazinyl, indolyl, benzofuranyl, benzothiophenyl, benzimidazolyl, quinolinyl, isoquinolinyl, quinazolinyl, quinoxalinyl, pyrazolyl, and the like.

"Heteroaryloxy" refers to a —O—R radical where R is heteroaryl as defined above e.g., furanyloxy, pyridinyloxy, indolyloxy, and the like.

"Heteroaryloxycarbonyl" refers to a —C(O)O—R radical where R is heteroaryl as defined above e.g., pyridinyloxycarbonyl, pyrimidinyloxycarbonyl, and the like.

"Heteroaralkyl" refers to a -(alkylene)-R radical where R is heteroaryl as defined above e.g., pyridinylmethyl, 1- or 2-furanylethyl, imidazolylmethyl, and the like.

"Heteroaralkyloxy" refers to a —O—R radical where R is heteroaralkyl as defined above e.g., pyridinylmethyloxy, furanylethyloxy, and the like.

"Heteroaralkyloxycarbonyl" refers to a —C(O)O—R radical where R is heteroaralkyl as defined above e.g., pyridinylmethyloxycarbonyl, pyrimidinylmethyloxycarbonyl, and the like.

"Heterocycloalkyl" refers to a saturated or partially unsaturated, mono or bicyclic radical of 4, 5 or 6 carbon ring atoms wherein one or more, preferably one, two, or three of the ring carbon atoms are replaced by a heteroatom selected from —N=, —N—, —O—, —S—, —SO—, or —S(O)$_2$— and further wherein one or two ring carbon atoms are optionally replaced by a keto (—CO—) group. The heterocycloalkyl ring is optionally fused to cycloalkyl, aryl or heteroaryl ring as defined herein. Representative examples include, but are not limited to, imidazolidinyl, morpholinyl, thiomorpholinyl, thiomorpholino-1-oxide, thiomorpholino-1,1-dioxide, tetrahydrofuranyl, tetrahydropyranyl, tetrahydrothiopyranyl, 1-oxo-tetrahydrothiopyranyl, 1,1-dioxotetrathio-pyranyl, indolinyl, piperazinyl, piperidyl, pyrrolidinyl, pyrrolinyl, quinuclidinyl,3,4-dihydroisoquinolinyl, dihydroindolyl, and the like.

When the heterocycloalkyl group contains at least one nitrogen ring atom it is referred to herein as "heterocycloamino" and is a subset of the heterocycloalkyl group as defined above.

"Heterocyclylalkylene" refers to a divalent heterocyclyl group, as defined in this Application, e.g., the instance wherein $R^3$ and $R^4$ together with the carbon atom to which both $R^3$ and $R^4$ are attached form heterocyclylalkylene" includes, but is not limited to, the following:

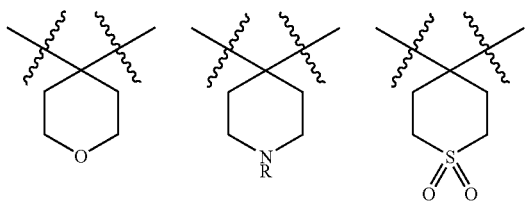

in which R is a substituent defined in the Summary of the Invention

"Heterocycloalkylalkyl" refers to a -(alkylene)-R radical where R is heterocycloalkyl as defined above e.g., pyrrolidinylmethyl, tetrahydrofuranylethyl, pyridinylmethylpiperidinylmethyl, and the like.

"Heterocycloalkyloxycarbonyl" refers to a —C(O)OR radical where R is heterocycloalkyl as defined above e.g., pyridinyloxycarbonyl, pyrimidinyloxycarbonyl, and the like.

"Hydroxy" means —OH radical. Unless indicated otherwise, the compounds of the invention containing hydroxy radicals include protected derivatives thereof. Suitable protecting groups for hydroxy moieties include benzyl and the like.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Isomers" mean compounds of Formula (I) having identical molecular formulae but differ in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center that has two enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992). It is understood that the names and illustration used in this Application to describe compounds of Formula (I) are meant to be encompassed all possible stereoisomers.

"Optional" or "optionally" or "may be" means that the subsequently described event or circumstance may or may not occur, and that the description includes instances where the event or circumstance occurs and instances in which it does not. For example, the phrase "wherein the aromatic ring in $R^a$ is optionally substituted with one or two substituents independently selected from alkyl" means that the aromatic ring may or may not be substituted with alkyl in order to fall within the scope of the invention.

The present invention also includes N-oxide derivatives of a compound of Formula (I). N-oxide derivative mean a compound of Formula (I) in which a nitrogen atom is in an oxidized state (i.e., N→O) e.g., pyridine N-oxide, and which possess the desired pharmacological activity.

"Pathology" of a disease means the essential nature, causes and development of the disease as well as the structural and functional changes that result from the disease processes.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of Formula (I) which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl) benzoic acid, cinnamic acid, mandelic acid, methylsulfonic acid, ethanesulfonic acid, 1,2-ethanedisulfonic acid, 2-hydroxy-ethanesulfonic acid, benzenesulfonic acid, p-chlorobenzenesulfonic acid, 2-naphthalenesulfonic acid, p-toluenesulfonic acid, camphorsulfonic acid, 4-methylbicyclo [2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

The present invention also includes prodrugs of a compound of Formula (I). Prodrug means a compound that is convertible in vivo by metabolic means (e.g. by hydrolysis) to a compound of Formula (I). For example, an ester of a compound of Formula (I) containing a hydroxy group may be convertible by hydrolysis in vivo to the parent molecule. Alternatively an ester of a compound of Formula (I) containing a carboxy group may be convertible by hydrolysis in vivo to the parent molecule. Suitable esters of compounds of Formula (I) containing a hydroxy group, are for example acetates, citrates, lactates, tartrates, malonates, oxalates, salicylates, propionates, succinates, fumarates, maleates, methylene-bis-βb-hydroxynaphthoates, gentisates, isethionates, di-p-toluoyltartrates, methylsulphonates, ethanesulphonates, benzenesulphonates, p-toluenesulphonates, cyclohexylsulphamates and quinates. Suitable esters of compounds of Formula (I) containing a carboxy group, are for example those described by Leinweber, F. J. Drug Metab. Res., 1987, 18, page 379. An especially useful class of esters of compounds of Formula (I) containing a hydroxy group, may be formed from acid moieties selected from those described by Bundgaard et al., J. Med. Chem., 1989, 32, pp 2503-2507, and include substituted (aminomethyl)-benzoates, for example, dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl) benzoates, e.g. 3- or 4-(morpholinomethyl)-benzoates, and (4-alkylpiperazin-1-yl)benzoates, e.g. 3- or 4-(4-alkylpiperazin-1-yl)benzoates.

"Protected derivatives" means derivatives of compounds of Formula (I) in which a reactive site or sites are blocked with protecting groups. Protected derivatives of compounds of Formula (I) are useful in the preparation of compounds of Formula (I) or in themselves may be active cathepsin S inhibitors. A comprehensive list of suitable protecting groups can be found in T. W. Greene, *Protective Groups in Organic Synthesis*, 3rd edition, John Wiley & Sons, Inc. 1999.

"Therapeutically effective amount" means that amount which, when administered to an animal for treating a disease, is sufficient to effect such treatment for the disease.

"Treatment" or "treating" means any administration of a compound of the present invention and includes:
(1) preventing the disease from occurring in an animal which may be predisposed to the disease but does not yet experience or display the pathology or symptomatology of the disease,
(2) inhibiting the disease in an animal that is experiencing or displaying the pathology or symptomatology of the diseased (i.e., arresting further development of the pathology and/or symptomatology), or
(3) ameliorating the disease in an animal that is experiencing or displaying the pathology or symptomatology of the diseased (i.e., reversing the pathology and/or symptomatology).

"Treatment" or "treating" with respect to combination therapy i.e., use with a biologic means any administration of a compound of the present invention and includes:
(1) preventing the immune response from occurring in an animal which may be predisposed to the immune response but does not yet experience or display the pathology or symptomatology of the immune response,
(2) inhibiting the immune response in an animal that is experiencing or displaying the pathology or symptomatology of the immune response (i.e., arresting further development of the pathology and/or symptomatology), or
(3) ameliorating the immune response in an animal that is experiencing or displaying the pathology or symptomatology of the immune response (i.e., reducing in degree or severity, or extent or duration, the overt manifestations of the immune response or reversing the pathology and/or symptomatology e.g., reduced binding and presentation of antigenic peptides by MHC class II molecules, reduced activation of T-cells and B-cells, reduced humoral and cell-mediated responses and, as appropriate to the particular immune response, reduced inflammation, congestion, pain, necrosis, reduced loss in the efficacy of a biologic agent, and the like).

The expression "wherein the aromatic or alicyclic ring in $R^5$ is optionally substituted with one, two, or three $R^a$ independently selected from alkyl, haloalkyl, alkoxy, hydroxy, haloalkoxy, or halo; or optionally substituted with one or two $R^b$ independently selected from hydrogen, alkyl, haloalkyl, alkoxy, hydroxy, haloalkoxy, halo, carboxy, or alkoxycarbonyl and one $R^c$ selected from hydroxyalkyl, alkoxyalkyl, aminoalkyl, aryl, heteroaryl, aralkyl, heteroaralkyl, cycloalkyl, cycloalkylalkyl, . . . " in the definition of $R^5$ in the compound of Formula (I) means that all the aromatic and alicyclic rings within the scope of $R^5$ whether directly or indirectly attached (e.g., $R^5$ is cycloalkylalkyl, -alkylene-X—$R^9$ where X is as defined in the Summary of the Invention and $R^9$ is ary, aralkyl, etc, . . . ) are optionally substituted with $R^a$, or $R^b$ and $R^c$, or $R^c$ alone.

Preferred Embodiments

I. Certain compounds of Formula (I) within the broadest scope set forth in the Summary of the Invention are preferred. For example:
(A) A preferred group of compounds is that wherein:
$R^1$ is hydrogen or methyl, preferably hydrogen;
$R^2$ is cyclopropyl, 1-phenylethyl[-CH($C_6H_5$)$CH_3$], or 1H-pyrazol-5-yl; preferably cyclopropyl.

(1) Within the above preferred group (A) and more preferred group contained therein, a more preferred group of compounds is that wherein $R^3$ is hydrogen and $R^4$ is alkyl, preferably methyl, ethyl, propyl or butyl, more preferably $R^4$ is ethyl or propyl.

(2) Within the above preferred group (A) and more preferred group contained therein, a more preferred group of compounds is that wherein $R^3$ is alkyl, preferably methyl or ethyl and $R^4$ is alkyl, preferably methyl, ethyl, propyl or butyl, more preferably $R^4$ is methyl. Preferably, $R^3$ and $R^4$ are methyl.

(3) Within the above preferred group (A) and more preferred groups contained therein, a more preferred group of compounds is that wherein $R^3$ and $R^4$ together with the carbon atom to which they are attached form cycloalkylene, preferably cyclopropylene, cyclopentylene, or cyclohexylene, more preferably cyclopropylene.

(4) Within the above preferred group (A) and more preferred group contained therein, a more preferred group of compounds is that wherein $R^3$ and $R^4$ together with the carbon atom to which they are attached form piperidin-4-yl substituted at the nitrogen atom with ethyl, 2,2,2-trifluoroethyl or cyclopropyl, tetrahydropyran-4-yl, tetrahydrothiopyran-4-yl, or 1,1-dioxotetrahydrothiopyran-4-yl.

(i) Within the above preferred groups (A) and A(1-4) and more preferred groups contained therein, a more preferred group of compounds is that wherein $R^6$ is haloalkyl, preferably, difluoromethyl, trifluoromethyl, 2,2,2-trifluoroethyl, 1,1,2,2,2-pentafluoroethyl, 1,1,2,2,3,3,3-heptafluoropropyl and $R^7$ and $R^8$ are hydrogen.

(ii) Within the above preferred groups (A) and A(1-4) and more preferred groups contained therein, a more preferred group of compounds is that wherein $R^6$ is haloalkyl, preferably, difluoromethyl, trifluoromethyl, 2,2,2-trifluoroethyl, or 1,1,2,2,2-pentafluoroethyl, $R^7$ is haloalkyl, preferably, trifluoromethyl, 2,2,2-trifluoroethyl, or 1,1,2,2,2-pentafluoroethyl, and $R^8$ is hydrogen.

(iii) Within the above preferred groups (A) and A(1-4) and more preferred groups contained therein, a more preferred group of compounds is that wherein $R^6$ is haloalkyl, preferably, difluoromethyl, trifluoromethyl, 2,2,2-trifluoroethyl, or 1,1,2,2,2-pentafluoroethyl, $R^7$ is alkyl, preferably, methyl, ethyl, or propyl, and $R^8$ is hydrogen.

(iv) Within the above preferred groups (A) and A(1-4) and more preferred groups contained therein, a more preferred group of compounds is that wherein $R^6$ is haloalkyl, preferably, difluoromethyl, trifluoromethyl, 2,2,2-trifluoroethyl, or 1,1,2,2,2-pentafluoroethyl, $R^7$ is haloalkyl, preferably, trifluoromethyl or 2,2,2-trifluoroethyl, and $R^8$ is aryl optionally substituted with one, two, or three $R^e$. Preferably $R^8$ is phenyl, 4-fluorophenyl, 2,3-, 2,4-, 2,5-, 2,6-, 3,4, or 3,5-difluorophenyl. More preferably, $R^6$ and $R^7$ are trifluoromethyl and $R^8$ is phenyl, 4-fluorophenyl, 2,3-, 2,4-, 2,5-, 2,6-, 3,4,- or 3,5-difluorophenyl.

(iv) Within the above preferred groups (A) and A(1-4) and more preferred groups contained therein, a more preferred group of compounds is that wherein $R^6$ is haloalkyl, preferably, difluoromethyl, trifluoromethyl, 2,2,2-trifluoroethyl, or 1,1,2,2,3-pentafluoroethyl, $R^7$ is alkyl, preferably, methyl or ethyl, and $R^8$ is aryl optionally substituted with one, two, or three $R^e$. Preferably $R^8$ is phenyl, 4-fluorophenyl, 2,3-, 2,4-, 2,5-, 2,6-, 3,4, or 3,5-difluorophenyl. More preferably, $R^6$ is trifluoromethyl and $R^7$ is methyl and $R^8$ is phenyl, 4-fluorophenyl, 2,3-, 2,4-, 2,5-, 2,6-, 3,4,- or 3,5-difluorophenyl.

(v) Within the above preferred groups (A) and A(1-4) and more preferred groups contained therein, a more preferred group of compounds is that wherein $R^6$ is haloalkyl, preferably, trifluoromethyl, difluoromethyl, 2,2,2-trifluoroethyl, or 1,1,2,2,2-pentafluoroethyl, $R^7$ is hydrogen, and $R^8$ is aryl optionally substituted with one, two, or three $R^e$. Preferably $R^8$ is phenyl, 4-fluorophenyl, 2,3-, 2,4-, 2,5-, 2,6-, 3,4,- or 3,5-difluorophenyl. More preferably, $R^6$ is trifluoromethyl and $R^8$ is phenyl, 4-fluorophenyl, 2,3-, 2,4-, 2,5-, 2,6-, 3,4, or 3,5-difluorophenyl, preferably 2,4-difluorophenyl.

(vi) Within the above preferred groups (A) and A(1-4) and more preferred groups contained therein, a more preferred group of compounds is that wherein $R^6$ is haloalkyl, preferably, trifluromethyl, 2,2,2-trifluoroethyl, or 1,1,2,2,2-pentafluoroethyl, $R^7$ is haloalkyl, preferably, trifluoromethyl or 2,2,2-trifluoroethyl, and $R^8$ is heteroaryl optionally substituted with one, two, or three $R^e$. Preferably $R^8$ is indol-5-yl, benzoxazol-5-yl, thiophen-3-yl, thiophen-2-yl, furan-2-yl, pyridin-4-yl, pyridin-3-yl, pyridin-2-yl, imidazol-5-yl, pyrimidin-2-yl, pyrazin-2-yl, pyrimidin-5-yl, pyrimdin-4-yl, pyridazin-4-yl, isoxazol-4-yl, imidazol-2-yl, [1.2.3]thiadiazol-4-yl, imidazol-4-yl, pyrazol-4-yl, thiazol-2-yl, pyrazol-4-yl, pyrrol-2-yl, pyrrol-3-yl, thiazol-4-yl, thiazol-5-yl optionally substituted with one or two methyl.

(vii) Within the above preferred groups (A) and A(1-4) and more preferred groups contained therein, a more preferred group of compounds is that wherein $R^6$ is haloalkyl, preferably, trifluromethyl, 2,2,2-trifluoroethyl, or 1,1,2,2,2-pentafluoroethyl, $R^7$ is alkyl, preferably, methyl or ethyl, and and $R^8$ is heteroaryl optionally substituted with one, two, or three $R^e$. Preferably $R^8$ is indol-5-yl, benzoxazol-5-yl, thiophen-3-yl, thiophen-2-yl, furan-2-yl, pyridine-4-yl, pyridin-3-yl, pyridin-2-yl, imidazol-5-yl, pyrimidin-2-yl, pyrazin-2-yl, pyrimidin-5-yl, pyrimdin-4-yl, pyridazin-4-yl, isoxazol-4-yl, imidazol-2-yl, [1.2.3]thiadiazol-4-yl, imidazol-4-yl, pyrazol-4-yl, thiazol-2-yl, pyrazol-4-yl, pyrrol-2-yl, pyrrol-3-yl, thiazol-4-yl, thiazol-5-yl optionally substituted with one or two methyl.

(viii) Within the above preferred groups (A) and A(1-4) and more preferred groups contained therein, a more preferred group of compounds is that wherein $R^6$ is haloalkyl, preferably, trifluromethyl, 2,2,2-trifluoroethyl, or 1,1,2,2,2-pentafluoroethyl, $R^7$ is hydrogen, and and $R^8$ is heteroaryl optionally substituted with one, two, or three $R^e$. Preferably $R^8$ is indol-5-yl, benzoxazol-5-yl, thiophen-3-yl, thiophen-2-yl, furan-2-yl, pyridin-4-yl, pyridin-3-yl, pyridin-2-yl, imidazol-5-yl, pyrimidin-2-yl, pyrazin-2-yl, pyrimidin-5-yl, pyrimdin-4-yl, pyridazin-4-yl, isoxazol-4-yl, imidazol-2-yl, [1.2.3] thiadiazol-4-yl, imidazol-4-yl, pyrazol-4-yl, thiazol-2-yl, pyrazol-4-yl, pyrrol-2-yl, pyrrol-3-yl, thiazol-4-yl, thiazol-5-yl optionally substituted with one or two methyl.

(a) Within the above preferred groups (A), A(1-4), A(i-viii) and A(1-4)(i-viii), and more preferred groups contained therein, an even more preferred group of compounds is that wherein $R^5$ is cycloalkylalkyl optionally substituted with one, two, or three $R^a$ independently selected from alkyl or halo or an $R^c$ selected from aralkyl or heteroaralkyl, preferably 1-methylcyclopentylmethyl, 1-methylcyclohexylmethyl, 1-methylcyclobutylmethyl, 1-methyl-3,3-difluorocyclobutylmethyl, 1-methyl-4,4-difluorocyclohexylmethyl, 1-benzylcyclopropylmethyl, 1-thiazol-2-ylmethylcyclopropylmethyl, or 1-methyl-3,3-difluorocyclopentylmethyl.

(b) Within the above preferred groups (A), A(1-4), A(1-viii) and A(i-4)(i-viii), and more preferred groups contained therein, an even more preferred group of compounds is that wherein $R^5$ is alkyl, preferably 2,2-dimethylpropyl, 3,3-dimethylpentyl, 2,2,3,3-tetramethylbutyl.

(c) Within the above preferred groups (A), A(1-4), A(1-viii) and A(i-4)(i-viii), and more preferred groups contained therein, an even more preferred group of compounds is that wherein $R^5$ is haloalkyl, preferably 2,2-dichloroethyl, 3,3,3-trifluoropropyl, 2,2-trifluoromethylethyl, or 2,2,2-trifluoroethyl.

(d) Within the above preferred groups (A), A(1-4), A(i-viii) and A(1-4)(i-viii), and more preferred groups contained therein, an even more preferred group of compounds is that wherein $R^5$ is haloalkyl substituted with aryl, heteroaryl or heterocycloalkyl, preferably 2,2-difluoro-3-phenylpropyl, 2,2-difluoro-3-tetrahydropyran-4-ylpropyl, 2,2-difluoro-3-morpholin-4-ylpropyl, 2,2-difluoro-3-pyridin-2-ylpropyl, 2,2-difluoro-3-pyridin-3-ylpropyl, or 2,2-dichloro-3-phenylpropyl.

(e) Within the above preferred groups (A), A(1-4), A(i-viii) and A(1-4)(i-viii), and more preferred groups contained therein, an even more preferred group of compounds is that wherein $R^5$ is aralkyl optionally substituted with one, two, or three $R^a$ independently selected from alkyl, haloalkyl, alkoxy, hydroxy, haloalkoxy, cyano, or halo; or optionally substituted with one or two $R^b$ independently selected from hydrogen, alkyl, haloalkyl, alkoxy, hydroxy, haloalkoxy, halo, carboxy, or alkoxycarbonyl and one $R^c$ selected from hydroxyalkyl, alkoxyalkyl, aminoalkyl, aryl, heteroaryl, aralkyl, heteroaralkyl, cycloalkyl, cycloalkylalkyl, heterocycloalkyl, heterocycloalkylalkyl, acyl, aryloxycarbonyl, aralkyloxycarbonyl, heteroaryloxycarbonyl, heteroaralkyloxycarbonyl, heterocycloalkyloxycarbonyl, aryloxy, heteroaryloxy, aralkyloxy, heteroaralkyloxy, aminocarbonyl, aminosulfonyl, or $-SO_2R^{11}$ (where $R^{11}$ is alkyl, cycloalkyl, aryl, heteroaryl, or heterocycloalkyl); and further wherein the aromatic or alicyclic ring in $R^c$ is optionally substituted with one, two, or three $R^d$ independently selected from alkyl, haloalkyl, alkoxy, hydroxy, haloalkoxy, or halo. Preferably, $R^5$ is benzyl, 4-methoxybenzyl, 3,4-dichlorobenzyl, 2-chlorobenzyl, 4-ethoxybenzyl, biphen-4-ylmethyl, naphth-1-ylmethyl, naphth-2-ylmethyl, 4-chlorobenzyl, 3-chlorobenzyl, 4-fluorobenzyl, 2-phenethyl, 4-hydroxybenzyl, 2-(4-hydroxyphenyl)ethyl, 2,6-difluorobenzyl, biphenyl-3-ylmethyl, 3-phenylpropyl, or 2,2-dimethyl-3-phenylpropyl. Preferably, $R^5$ is 2-chlorobenzyl, 3-chlorobenzyl, or 4-fluorobenzyl.

(f) Within the above preferred groups (A), A(1-4), A(i-viii) and A(1-4)(i-viii), and more preferred groups contained therein, an even more preferred group of compounds is that wherein $R^5$ is heteroaralkyl optionally substituted with one, two, or three $R^a$ independently selected from alkyl, haloalkyl, alkoxy, hydroxy, haloalkoxy, cyano, or halo; or optionally substituted with one or two $R^b$ independently selected from hydrogen, alkyl, haloalkyl, alkoxy, hydroxy, haloalkoxy, halo, carboxy, or alkoxycarbonyl and one $R^c$ selected from hydroxyalkyl, alkoxyalkyl, aminoalkyl, aryl, heteroaryl, aralkyl, heteroaralkyl, cycloalkyl, cycloalkylalkyl, heterocycloalkyl, heterocycloalkylalkyl, acyl, aryloxycarbonyl, aralkyloxycarbonyl, heteroaryloxycarbonyl, heteroaralkyloxycarbonyl, aryloxy, heteroaryloxy, aralkyloxy, heteroaralkyloxy, aminocarbonyl, aminosulfonyl, or $-SO_2R^{11}$ (where $R^{11}$ is alkyl, aryl, heteroaryl, or heterocycloalkyl); and further wherein the aromatic or alicyclic ring in $R^c$ is optionally substituted with one, two, or three $R^d$ independently selected from alkyl, haloalkyl, alkoxy, hydroxy, haloalkoxy, or halo. Preferably, $R^5$ is 2-bromothiophen-5-ylmethyl, pyridin-4-ylmethyl, or 2,2-dimethyl-3-pyridin-3-ylpropyl.

(g) Within the above preferred groups (A), A(1-4), A(i-viii) and A(1-4)(i-viii), and more preferred groups contained therein, an even more preferred group of compounds is that wherein $R^5$ is -(alkylene)-$S(O)_2$—$R^9$ where $R^9$ is alkyl, preferably $R^5$ is methylsulfonylmethyl, ethylsulfonylmethyl, propyl-1-sulfonylmethyl, 2-methylpropylsulfonylmethyl, 2-methyl-sulfonylethyl, or 2-ethylsulfonylethyl.

(h) Within the above preferred groups (A), A(1-4), A(i-viii) and A(1-4)(i-viii), and more preferred groups contained therein, an even more preferred group of compounds is that wherein $R^5$ is -(alkylene)-S(O)$_2$—$R^9$ where $R^9$ is aryl or aralkyl optionally substituted with one, two, or three $R^a$ independently selected from alkyl, haloalkyl, alkoxy, hydroxy, haloalkoxy, cyano, or halo; or optionally substituted with one or two $R^b$ independently selected from hydrogen, alkyl, haloalkyl, alkoxy, hydroxy, haloalkoxy, halo, carboxy, or alkoxycarbonyl and one $R^c$ selected from hydroxyalkyl, alkoxyalkyl, aminoalkyl, aryl, heteroaryl, aralkyl, heteroaralkyl, cycloalkyl, cycloalkylalkyl, heterocycloalkyl, heterocycloalkylalkyl, acyl, aryloxycarbonyl, aralkyloxycarbonyl, heteroaryloxycarbonyl, heteroaralkyloxycarbonyl, aryloxy, heteroaryloxy, aralkyloxy, heteroaralkyloxy, aminocarbonyl, aminosulfonyl, or —SO$_2$R$^{11}$ (where R$^{11}$ is alkyl, aryl, heteroaryl, or heterocycloalkyl); and further wherein the aromatic or alicyclic ring in R$^c$ is optionally substituted with one, two, or three $R^d$ independently selected from alkyl, haloalkyl, alkoxy, hydroxy, haloalkoxy, or halo. Preferably $R^5$ is 2-difluoromethoxyphenyl-methanesulfonylmethyl, 2-phenylsulfonylethyl, 4-fluorophenylmethanesulfonylmethyl, 4-aminocarbonylphenylmethanesulfonylmethyl, 4-piperazin-1-ylphenylmethanesulfonylmethyl, 2-fluorophenylmethanesulfonylmethyl, 3-fluorophenylmethanesulfonylmethyl, 2,4,6-trifluorophenylmethanesulfonylmethyl, 2-, 3-, or 4-trifluoromethylphenylmethanesulfonylmethyl, phenylmethanesulfonylmethyl, 2-(2-, 3-, or 4-trifluoromethylphenyl)sulfonylethyl, or 2-(2-, 3-, or 4-fluorophenyl)sulfonylethyl.

(i) Within the above preferred groups (A), A(1-4), A(i-viii) and A(1-4)(i-viii), and more preferred groups contained therein, an even more preferred group of compounds is that wherein $R^5$ is -(alkylene)-S(O)$_2$—$R^9$ where $R^9$ is heteroaryl or heteroaralkyl optionally substituted with one, two, or three $R^a$ independently selected from alkyl, haloalkyl, alkoxy, hydroxy, haloalkoxy, cyano, or halo; or optionally substituted with one or two $R^b$ independently selected from hydrogen, alkyl, haloalkyl, alkoxy, hydroxy, haloalkoxy, halo, carboxy, or alkoxycarbonyl and one $R^c$ selected from hydroxyalkyl, alkoxyalkyl, aminoalkyl, aryl, heteroaryl, aralkyl, heteroaralkyl, cycloalkyl, cycloalkylalkyl, heterocycloalkyl, heterocycloalkylalkyl, acyl, aryloxycarbonyl, aralkyloxycarbonyl, heteroaryloxycarbonyl, heteroaralkyloxycarbonyl, aryloxy, heteroaryloxy, aralkyloxy, heteroaralkyloxy, aminocarbonyl, aminosulfonyl, or —SO$_2$R$^{11}$ (where R$^{11}$ is alkyl, aryl, heteroaryl, or heterocycloalkyl); and further wherein the aromatic or alicyclic ring in R$^c$ is optionally substituted with one, two, or three $R^d$ independently selected from alkyl, haloalkyl, alkoxy, hydroxy, haloalkoxy, or halo. Preferably $R^5$ is pyridin-2-ylmethanesulfonylmethyl, pyridin-3-ylmethanesulfonylmethyl, pyridin-4-ylmethanesulfonylmethyl, 3-difluoromethoxypyridin-2-ylmethanesulfonylmethyl, 2-difluoromethoxypyridin-3-ylmethanesulfonylmethyl, 4-difluoromethoxypyridin-3-ylmethanesulfonylmethyl, 3-difluoromethoxypyridin-4-ylmethanesulfonylmethyl, pyrimidin-2-ylmethanesulfonylmethyl, pyrimidin-5-ylmethanesulfonylmethyl, 3-trifluoromethylpyridin-2-ylmethanesulfonylmethyl, 4-trifluoromethylpyridin-3-ylmethanesulfonylmethyl, 3,5-dimethylisoxazol-4-ylmethanesulfonylmethyl, 2-fluorofuran-5-ylmethanesulfonylmethyl, 2-methylthiazol-4-ylmethanesulfonylmethyl, furan-2-ylmethanesulfonylmethyl, 2-pyridin-2-ylethanesulfonylmethyl, 2-pyridin-3-ylethanesulfonylmethyl, 2-pyridin-4-ylethanesulfonylmethyl, 2-pyridin-3-ylsulfonylethyl, 2-pyridin-4-ylsulfonylethyl, 3-pyridin-3-ylsulfonylpropyl, 1,3,5-triazin-2-ylmethanesulfonylmethyl, 1,3,4-thiadiazol-2-ylmethanesulfonylmethyl, oxazol-5-ylmethanesulfonylmethyl, thiazol-5-ylmethanesulfonylmethyl, or thiazol-2-ylmethanesulfonylmethyl.

(j) Within the above preferred groups (A), A(1-4), A(i-viii) and A(1-4)(i-viii), and more preferred groups contained therein, an even more preferred group of compounds is that wherein $R^5$ is -(alkylene)-S(O)$_2$—$R^9$ where $R^9$ is heterocycloalkyl or heterocycloalkylalkyl optionally substituted with one, two, or three $R^a$ independently selected from alkyl, haloalkyl, alkoxy, hydroxy, haloalkoxy, cyano, or halo; or optionally substituted with one or two $R^b$ independently selected from hydrogen, alkyl, haloalkyl, alkoxy, hydroxy, haloalkoxy, halo, carboxy, or alkoxycarbonyl and one $R^c$ selected from hydroxyalkyl, alkoxyalkyl, aminoalkyl, aryl, heteroaryl, aralkyl, heteroaralkyl, cycloalkyl, cycloalkylalkyl, heterocycloalkyl, heterocycloalkylalkyl, acyl, aryloxycarbonyl, aralkyloxycarbonyl, heteroaryloxycarbonyl, heteroaralkyloxycarbonyl, aryloxy, heteroaryloxy, aralkyloxy, heteroaralkyloxy, aminocarbonyl, aminosulfonyl, or —SO$_2$R$^{11}$ (where R$^{11}$ is alkyl, cycloalkyl, aryl, heteroaryl, or heterocycloalkyl); and further wherein the aromatic or alicyclic ring in R$^c$ is optionally substituted with one, two, or three $R^d$ independently selected from alkyl, haloalkyl, alkoxy, hydroxy, haloalkoxy, or halo. Preferably, $R^5$ is piperidin-1-ylsulfonylmethyl or piperidin-4-ylmethanesulfonylmethyl wherein the nitrogen atom in the piperidine ring is substituted with methyl, ethyl, acetyl, methylsulfonyl, or aminosulfonyl, tetrahydropyran-4-ylsulfonylmethyl, tetrahydropyran-4-ylsulfonylmethyl, 1,1-dioxotetrahydrothiopyran-4-ylmethanesulfonylmethyl, or morpholin-4-ylmethanesulfonyl-methyl.

(k) Within the above preferred groups (A), A(1-4), A(i-viii) and A(1-4)(i-viii), and more preferred groups contained therein, an even more preferred group of compounds is that wherein $R^5$ is -(alkylene)-S(O)$_2$—$R^9$ where $R^9$ is cycloalkylalkyl, preferably $R^5$ is cyclopropylmethylsulfonylmethyl.

(l) Within the above preferred groups (A), A(1-4), A(i-viii) and A(1-4)(i-viii), and more preferred groups contained therein, $R^5$ is ethylsulfonylmethyl, 2-methysulfonylethyl, 2-methylpropylsulfonylmethyl, benzenesulfonylmethyl, 2-phenylsulfonylethyl, naphth-2-ylmethanesulfonylmethyl, biphenyl-2-ylmethanesulfonylmethyl, biphenyl-4-ylmethanesulfonylmethyl, phenylmethanesulfonylmethyl, 2-phenylmethanesulfonylethyl, 4-tert-butylphenylmethanesulfonylmethyl, 2-fluoro-phenylmethanesulfonylmethyl, 3-fluorophenylmethane-sulfonylmethyl, 4-fluorophenylmethanesulfonylmethyl, 2-chlorophenylmethanesulfonylmethyl, 3-chlorophenylmethanesulfonylmethyl, 4-chlorophenylmethanesulfonylmethyl, 2-methoxyphenylmethanesulfonylmethyl, 4-methoxyphenylmethanesulfonylmethyl, 2-trifluoromethoxyphenylmethanesulfonylmethyl, 3-trifluoromethoxyphenylmethanesulfonyl-methyl, 4-trifluoromethoxyphenylmethanesulfonylmethyl, 2-trifluoromethylphenyl-methanesulfonylmethyl, 3-trifluoromethylphenylmethanesulfonylmethyl, 4-trifluoromethylphenylmethanesulfonylmethyl, 2-cyanophenylmethanesulfonylmethyl, 3-cyanophenylmethanesulfonylmethyl, 2-bromophenylmethanesulfonylmethyl, 2-methylphenylmethanesulfonylmethyl, 3-methylphenylmethanesulfonylmethyl, 4-methylphenylmethanesulfonylmethyl, 2-(4-trifluoromethoxy-benzenesulfonyl)ethyl, 2-(3-trifluoromethoxybenzenesulfonyl)ethyl, 2-(2-trifluoromethoxybenzenesulfonyl)-ethyl, 2-difluoromethoxyphenylmethanesulfonylmethyl, 3-difluoromethoxyphenylmethanesulfonylmethyl, 4-difluoromethoxyphenylmethanesulfonylmethyl, 2-(4-difluoromethoxybenzenesulfonyl)ethyl, 2-(2-difluoromethoxybenzenesulfonyl)ethyl, 2-(3-difluoromethoxybenzenesulfonyl)ethyl, 3-chloro-2-fluorophenylmethanesulfonylmethyl, 3,5-dimethylphenylmethanesulfonylmethyl, 3,5-bis-trifluoromethylphenylmethanesulfonylmethyl, 2,5-difluorophenylmethanesulfonylmethyl, 2,6-difluorophenylmethanesulfonylmethyl, 2,3-difluorophenylmethanesulfonylmethyl, 3,4-difluorophenylmethanesulfonylmethyl, 2,4-difluorophenylmethanesulfonylmethyl, 2,5-dichlorophenylmethanesulfonylmethyl, 3,4-dichlorophenylmethanesulfonylmethyl, 2,6-dichlorophenylmethanesulfonylmethyl, 2-fluoro-3-methylphenylmethanesulfonylmethyl, 4-fluoro-2-trifluoromethoxyphenylmethanesulfonylmethyl, 2-fluoro-6-trifluoromethylphenylmethanesulfonylmethyl, 2-fluoro-3-trifluoromethylphenylmethanesulfonylmethyl, 2-fluoro-4-trifluoromethylphenylmethanesulfonylmethyl, 2-fluoro-5-trifluoromethylphenylmethanesulfonylmethyl, 4-fluoro-3-trifluoromethylphenylmethanesulfonylmethyl, 2-chloro-5-trifluoromethylphenylmethanesulfonylmethyl, 2,4,6-trifluorophenylmethanesulfonylmethyl, 2,4,5-trifluorophenylmethanesulfonylmethyl, 2,3,4-trifluorophenylmethanesulfonylmethyl, 2,3,5-trifluorophenylmethanesulfonylmethyl, 2,5,6-trifluorophenylmethanesulfonyl-methyl, 3,4,5-trimethoxyphenylmethanesulfonylmethyl, pyridin-2-ylmethanesulfonylmethyl, pyridin-3-ylmethanesulfonylmethyl, pyridin-4-ylmethanesulfonylmethyl, 2-(pyridin-2-ylsulfonyl)ethyl, 2-(pyridin-4-ylsulfonyl)ethyl, oxypyridin-2-ylmethanesulfonylmethyl, cyclohexylmethanesulfanylmethyl, cyclohexylmethanesulfonylmethyl, cyclopropylmethanesulfonylmethyl, thiophene-2-sulfonylmethyl, 5-chlorothien-2-ylmethanesulfonylmethyl, or 3,5-dimethyl-isoxazol-4-ylmethanesulfonylmethyl.

(m) Within the above preferred groups (A), A(1-4), A(i-viii) and A(1-4)(i-viii), and more preferred groups contained therein, $R^5$ is 1-ethoxycarbonylpiperidin-4-ylmethyl, 1-methylpiperidin-4-ylmethyl, 2-tetrahydropyran-4-ylethyl, pyrrolidin-1-ylmethyl, piperidin-1-ylmethyl, morpholin-4-ylmethyl, 2-morpholin-4-ylethyl, thiomorpholin-4-ylmethyl, 1-oxo-thiomorpholin-4-ylmethyl, 1,1-dioxothiomorpholin-4-ylmethyl, tetrahydrothiopyran-4-ylmethyl, 1-oxotetrahydrothiopyran-4-ylmethyl, 1,1-dioxotetrahydrothiopyran-4-ylmethyl, 1-methylpiperazin-4-ylmethyl, benzyloxymethyl, ethoxymethyl, isopropyloxymethyl, 2-piperidin-1-yl-ethyl, 2-pyrrolidin-1-ylethyl, tert-butyloxymethyl, imidazol-4-ylmethyl, indol-3-ylmethyl, indol-2-ylmethyl, 1-benzyl-imidazol-4-ylmethyl, 4-ethyl-4-methylpiperidin-1-ylmethyl, indol-1-ylmethyl, 1-methyl-piperidin-2-ylmethyl, 2,2,-difluoro-3-thien-2-ylmethyl, or pyridin-4-ylmethyl.

(n) Within the above preferred groups (A), A(1-4), A(i-viii) and A(1-4)(i-viii), and more preferred groups contained therein, $R^5$ is 3,5-dimethylisoxazol-4-ylmethanesulfonylmethyl; 2-CF$_3$methylphenylmethane-sulfonylmethyl, 3-CF$_3$pyridin-2-ylmethanesulfonylmethyl, 2-F-furan-5-ylmethanesulfonyl-methyl, 2-methylthiazol-4-ylmethanesulfonylmethyl, tetrahydropyran-4-ylmethane-sulfonylmethyl, 1,1-dioxo-1$\lambda^6$-hexahydrothiopyran-4-ylmethanesulfonylmethyl, 1-ethylpiperidin-4-ylmethanesulfonylmethyl, 2-oxo-tetrahydropyrimidin-4-ylmethane-sulfonylmethyl, 1-ethyl-2-oxopiperidin-4-ylmethanesulfonylmethyl, 1-acetylpiperidin-4-ylmethanesulfonylmethyl, 1-ethoxycarbonylpiperidin-4-ylmethanesulfonylmethyl, 1-methylsulfonylpiperidin-4-ylmethanesulfonylmethyl, 1-cyclopropylpiperidin-4-ylmethane-sulfonylmethyl, 1-acetylazetidin-3-ylmethanesulfonylmethyl, 1-ethoxycarbonylazetidin-3-ylmethanesulfonylmethyl, 1-methylsulfonylazetidin-3-ylmethanesulfonylmethyl, 1-ethylazetidin-3-ylmethanesulfonylmethyl, 1-cyclopropylazetidin-3-ylmethanesulfonylmethyl furan-2-ylmethanesulfonylmethyl, difluoro-(4-fluorophenyl)methanesulfonylmethyl, difluoro-(pyrazin-2-yl)methanesulfonylmethyl, difluoro-(2-difluoromethoxyphenyl)-methanesulfonylmethyl, 1-acetylpiperidin-4-ylsulfonylmethyl, 1-ethoxycarbonylpiperidin-4-ylsulfonylmethyl, 1-cyclopropyllpiperidin-4-ylsulfonylmethyl, 2-(pyridin-2-yl)ethanesulfonyl-methyl, 2-(pyridin-3-yl)ethanesulfonylmethyl, 2-(pyridin-4-yl)ethanesulfonylmethyl, 3-(pyridin-2-yl)propanesulfonylmethyl, 2,6-difluorophenylmethanesulfonyl, [1.3.5]triazin-2-ylmethanesulfonylmethyl, [1.3.4]thiadiazol-2-ylmethanesulfonylmethyl, oxazol-5-ylmethanesulfonylmethyl, thiazol-5-ylmethanesulfonylmethyl, 4-fluorophenylmethanesulfonylmethyl, 4-aminocarbonylphenylmethanesulfonylmethyl, 4-piperazin-4-ylphenylmethanesulfonylmethyl, 5-fluoroindol-3-ylmethanesulfonylmethyl, 4,6-difluoroindol-3-ylmethanesulfonylmethyl, 1-methylindol-3-ylmethanesulfonylmethyl, 4-fluoroindol-3-ylmethanesulfonylmethyl, 2-(5-fluoroindol-3-yl)ethanesulfonylmethyl, 2-(4,6-difluoroindol-3-yl)ethanesulfonylmethyl, 2-(1-methylindol-3-yl)ethanesulfonylmethyl, 2-(4-fluoroindol-3-yl)ethanesulfonylmethyl, 2-quinolin-3-ylethanesulfonylmethyl, 2-quinolin-2-ylethanesulfonylmethyl, isoquinolin-3-ylmethanesulfonylmethyl, 2-(isoquinolin-3-yl)ethanesulfonylmethyl, 2,4-difluoropyridin-3-ylmethane-sulfonylmethyl, 3,4-difluoropyridin-4-ylmethanesulfonylmethyl, 2-(2,4-difluoropyridin-3-yl)ethanesulfonylmethyl, 2-(3,4-difluoropyridin-4-yl)ethanesulfonylmethyl, fluoro-(2,4-difluoropyridin-3-yl)methanesulfonylmethyl, fluoro-(3,4-difluoropyridin-4-yl)methane-sulfonylmethyl, 2,4-diCF$_3$pyridin-3-ylmethanesulfonylmethyl, 3,4-diCF$_3$pyridin-4-ylmethane-sulfonylmethyl, 2-(2,4-diCF$_3$pyridin-3-yl)ethanesulfonylmethyl, 2-(3,4-diCF$_3$pyridin-4-yl)ethanesulfonylmethyl, fluoro-(2,4-diCF$_3$pyridin-3-yl)methanesulfonylmethyl, fluoro-(3,4-diCF$_3$pyridin-4-yl)methanesulfonylmethyl, 4-F-pyridin-3-ylmethanesulfonylmethyl, 3-F-pyridin-5-ylmethanesulfonylmethyl, 2-F-pyridin-5-ylmethanesulfonylmethyl, 2-F-pyridin-3-ylmethanesulfonylmethyl, 5-F-pyridin-2-ylmethanesulfonylmethyl, 4-F-pyridin-2-ylmethanesulfonylmethyl, 4-F-1-oxopyridin-3-ylmethanesulfonylmethyl, 3-F-1-oxopyridin-5-ylmethanesulfonylmethyl, 2-F-1-oxopyridin-5-ylmethanesulfonylmethyl, 2-F-1-oxopyridin-3-ylmethanesulfonylmethyl, 5-F-1-oxopyridin-2-ylmethanesulfonylmethyl, 4-F-1-oxopyridin-2-ylmethanesulfonylmethyl, 4-CF$_3$-pyridin-2-ylmethanesulfonylmethyl, 3-CF$_3$-pyridin-5-ylmethane-sulfonylmethyl, 3-F-pyridin-2-ylmethanesulfonylmethyl, 2-CF$_3$-pyridin-3-ylmethane-sulfonylmethyl, 4-CF$_3$-1-oxopyridin-2-ylmethanesulfonylmethyl, 3-CF$_3$-1-oxopyridin-5-ylmethanesulfonylmethyl, 3-F-1-oxopyridin-2-ylmethanesulfonylmethyl, 2-CF$_3$-1-oxopyridin-3-ylmethanesulfonylmethyl, 5-CF$_3$-1-oxopyridin-2-ylmethanesulfonylmethyl, 2-CH$_3$-pyridin-6-ylmethanesulfonylmethyl, 3-CH$_3$-pyridin-2-ylmethanesulfonylmethyl, 4-CH$_3$-pyridin-3-ylmethanesulfonylmethyl, 3-CH$_3$-pyridin-4-ylmethanesulfonylmethyl, 2-(2-CH$_3$-pyridin-6-yl)ethanesulfonylmethyl, 2-(3-CF$_3$-pyridin-2-yl)ethanesulfonylmethyl, 2-(4-CF$_3$-pyridin-3-yl)ethanesulfonylmethyl, 2-(3-CF$_3$-pyridin-4-yl)ethanesulfonylmethyl, 2-C$_2$H$_5$-pyridin-6-ylmethanesulfonylmethyl, 3-C$_2$H$_5$-pyridin-2-ylmethanesulfonylmethyl, 4-C$_2$H$_5$-pyridin-3-ylmethanesulfonylmethyl, 3-C$_2$H$_5$-pyridin-4-ylmethanesulfonylmethyl, 2-(2-C$_2$H$_5$-pyridin-6-yl)ethanesulfonylmethyl, 2-(3-C$_2$H$_5$-pyridin-2-yl)ethanesulfonylmethyl, 2-(4-C$_2$H$_5$-pyridin-3-yl)ethanesulfonylmethyl, 2-C$_2$H$_5$-pyridin-4-yl)ethanesulfonylmethyl, 2-(2-CH$_3$-pyridin-3-yl)ethanesulfonylmethyl, 2-CF$_3$-pyridin-3-ylmethanesulfonylmethyl, 2-(3-CF$_3$-pyridin-4-yl)ethanesulfonylmethyl, 3-CF$_3$-pyridin-4-ylmethanesulfonylmethyl, cinnolin-3-ylmethanesulfonylmethyl, 2-(cinnolin-3-yl)ethanesulfonylmethyl, phthalazin-1-ylmethanesulfonylmethyl, 2-(phthalazin-1-yl)ethanesulfonylmethyl, 2-(quinoxalin-2-yl)ethanesulfonylmethyl, quinazolin-2-ylmethanesulfonylmethyl, 2-(quinazolin-2-yl)ethanesulfonylmethyl, [1,8]naphthyridin-2-ylmethanesulfonylmethyl, 2-([1,8]naphthyridin-2-yl)ethanesulfonylmethyl, [1,8]naphthyridin-3-ylmethanesulfonylmethyl, 2-([1,8]naphthyridin-3-yl)ethanesulfonylmethyl, 3-Cl-pyridin-2-ylmethanesulfonylmethyl, 4-Cl-pyridin-3-ylmethanesulfonylmethyl, 3-Cl-pyridin-4-ylmethanesulfonylmethyl, 3-F-pyridin-2-ylmethanesulfonylmethyl, 4-F-pyridin-3-ylmethanesulfonyl-methyl, 3-F-pyridin-4-ylmethanesulfonylmethyl, isoquinolin-4-ylmethanesulfonylmethyl, 6-phenylpyridin-2-ylmethanesulfonylmethyl, 3-phenylpyridin-2-ylmethanesulfonylmethyl, 4-phenylpyridin-3-ylmethanesulfonylmethyl, 3-phenylpyridin-4-ylmethanesulfonylmethyl, 2-(6-phenylpyridin-2-yl)ethanesulfonylmethyl, 2-(3-phenylpyridin-2-yl)ethanesulfonylmethyl, 2-(4-phenylpyridin-3-yl)ethanesulfonylmethyl, 2-(3-phenylpyridin-4-yl)ethanesulfonylmethyl, 6-(pyridin-2-yl)pyridin-2-ylmethanesulfonylmethyl, 3-(pyridin-2-yl)pyridin-2-ylmethane-sulfonylmethyl, 4-(pyridin-2-yl)pyridin-3-ylmethanesulfonylmethyl, 3-(pyridin-2-yl)pyridin-4-ylmethanesulfonylmethyl, 2-[6-(pyridin-2-yl)pyridin-2-yl]ethanesulfonylmethyl, 2-[3-(pyridin-2-yl)pyridin-2-yl]ethanesulfonylmethyl, 2-[4-(pyridin-2-yl)pyridin-3-yl]ethanesulfonylmethyl, 2-[3-(pyridin-2-yl)pyridin-4-yl]ethanesulfonylmethyl, 6-(pyridin-3-yl)pyridin-2-ylmethane-sulfonylmethyl, 3-(pyridin-3-yl)pyridin-2-ylmethanesulfonylmethyl, 4-(pyridin-3-yl)pyridin-3-ylmethanesulfonylmethyl, 3-(pyridin-3-yl)pyridin-4-ylmethanesulfonylmethyl, 2-[6-(pyridin-3-yl)pyridin-2-yl]ethanesulfonylmethyl, 2-[3-(pyridin-3-yl)pyridin-2-yl]ethanesulfonylmethyl, 2-[4-(pyridin-3-yl)pyridin-3-yl]ethanesulfonylmethyl, 2-[3-(pyridin-3-yl)pyridin-4-yl]ethanesulfonylmethyl, 6-(pyridin-4-yl)pyridin-2-ylmethanesulfonylmethyl, 3-(pyridin-4-yl)pyridin-2-ylmethanesulfonylmethyl, 4-(pyridin-4-yl)pyridin-3-ylmethanesulfonylmethyl, 3-(pyridin-4-yl)pyridin-4-ylmethanesulfonylmethyl, 2-[6-(pyridin-4-yl)pyridin-2-yl]ethanesulfonylmethyl, 2-[3-(pyridin-4-yl)pyridin-2-yl]ethanesulfonylmethyl, 2-[4-(pyridin-4-yl)pyridin-3-yl]ethanesulfonylmethyl, 2-[3-(pyridin-4-yl)pyridin-4-yl]ethanesulfonylmethyl, 2,2-dimethylcyclopropylmethanesulfonylmethyl, biphen-2-ylmethanesulfonylmethyl, 2-thiophen-2-ylphenylmethanesulfonylmethyl, 2-thiazol-2-ylphenylmethanesulfonylmethyl, 2-thiazol-5-ylphenylmethanesulfonylmethyl, 2-[1.2.3]thiadiazol-5-ylphenylmethanesulfonylmethyl, 2-isoxazol-5-ylphenylmethanesulfonylmethyl, 2-(1-methylpyrazol-5-yl)phenyl-methanesulfonylmethyl, 2-[1.2.3]triazol-5-ylphenylmethanesulfonylmethyl, 2-[1.2.3]oxadiazol-5-ylphenylmethanesulfonylmethyl, 2-[(1.2.3)triazol-5-yl]phenylmethanesulfonylmethyl, 2-[(1.2.3)triazol-1-yl]phenylmethanesulfonylmethyl, oxazolo[5,4-b]pyridin-2-ylmethane-sulfonylmethyl, oxazolo[4,5-c]pyridin-2-ylmethanesulfonylmethyl, oxazolo[4,5-b]pyridin-2-ylmethanesulfonylmethyl, benzimidazol-5-ylmethanesulfonylmethyl, benzimidazol-4-ylmethanesulfonylmethyl, 3H-imidazo[4,5-b]pyridin-2-ylmethanesulfonylmethyl, 3H-imidazo[4,5-c]pyridin-2-ylmethanesulfonylmethyl, 3-CF$_3$-3H-imidazo[4,5-b]pyridin-2-ylmethanesulfonylmethyl, 3-CF$_3$-3H-imidazo[4,5-c]pyridin-2-ylmethanesulfonylmethyl, 1-CF$_3$-1H-imidazo[4,5-c]pyridin-2-ylmethanesulfonylmethyl, 1-CF$_3$-1H-imidazo[4,5-b]pyridin-2-ylmethanesulfonylmethyl, thiazolo[5,4-b]pyridin-2-ylmethanesulfonylmethyl, thiazolo[4,5-c]pyridin-2-ylmethanesulfonylmethyl, thiazolo[4,5-b]pyridin-2-ylmethanesulfonylmethyl, 5-CF$_3$thiazolo[5,4-b]pyridin-2-ylmethanesulfonylmethyl, 4-CF$_3$-thiazolo[4,5-c]pyridin-2-ylmethanesulfonylmethyl, 7-CF$_3$-thiazolo[4,5-b]pyridin-2-ylmethanesulfonylmethyl, 3-CF$_3$-1H-pyrrolo[2,3-b]pyridin-2-ylmethanesulfonylmethyl, 3-CF$_3$-1H-pyrrolo[3,2-c]pyridin-2-ylmethanesulfonylmethyl, 3-CF$_3$-1H-pyrrolo[3,2-b]pyridin-2-ylmethanesulfonylmethyl, imidazo[1,2-c]pyrimidin-2-methanesulfonylmethyl, 8-CF$_3$-imidazo[1,2-c]pyrimidin-2-methanesulfonylmethyl, imidazo[1,2-a]pyrimidin-2-methanesulfonylmethyl, 8-CF$_3$-imidazo[1,2-b]pyridazin-2-ylmethanesulfonylmethyl, imidazo[1,2-a]pyrazin-2-methanesulfonylmethyl, 8-CF$_3$-imidazo[1,2-a]pyrazin-2-methanesulfonylmethyl, pyrazolo[1,5-c]pyrimidin-2-ylmethanesulfonylmethyl, 3-CF$_3$-pyrazolo[1,5-c]pyrimidin-2-ylmethanesulfonylmethyl, 4-CF$_3$-pyrazolo[1,5-c]pyrimidin-2-ylmethanesulfonylmethyl, imidazo[1,2-d][1,2,4]triazin-2-methanesulfonylmethyl, 3-CF$_3$-imidazo[1,2-d][1,2,4]triazin-2-methanesulfonylmethyl, [1,3]benzoxazol-2-ylmethanesulfonylmethyl, 5-F-[1,3]benzoxazol-2-ylmethanesulfonylmethyl[1,3]benzoxazol-4-ylmethanesulfonylmethyl, 2-CF$_3$-[1,3]benzoxazol-4-ylmethanesulfonyl-methyl, [1,3]benzoxazol-7-ylmethanesulfonylmethyl, 2-CF$_3$-[1,3]benzoxazol-7-ylmethane-sulfonylmethyl, [1,2]benzoxazol-3-ylmethanesulfonylmethyl, [1,2]benzoxazol-4-ylmethanesulfonylmethyl, 5-CF$_3$-[1,2]benzoxazol-4-ylmethanesulfonylmethyl, 3-CF$_3$-[1,2]benzoxazol-4-ylmethanesulfonylmethyl, 6-CF$_3$-[1,2]benzoxazol-7-ylmethane-sulfonylmethyl, 6-CN-[1,2]benzoxazol-7-ylmethanesulfonylmethyl, 3-CF$_3$-[1,2]benzoxazol-7-ylmethanesulfonylmethyl, 5-F-[1,3]benzoxazol-3-ylmethanesulfonylmethyl, [2,3]benzoxazol-7-ylmethanesulfonylmethyl, 6-CF$_3$-[2,3]benzoxazol-7-ylmethanesulfonylmethyl, 1-CF$_3$-[2,3]benzoxazol-7-ylmethanesulfonylmethyl, 5-CF$_3$-[2,3]benzoxazol-4-ylmethanesulfonylmethyl, 5-CN-[2,3]benzoxazol-4-ylmethanesulfonylmethyl, 1-CF$_3$-[2,3]benzoxazol-4-ylmethanesulfonylmethyl, benzothiazol-2-ylmethanesulfonylmethyl, 5-F-benzothiazol-2- ylmethanesulfonylmethyl, benzothiazol-4-ylmethanesulfonylmethyl, 2-CF$_3$-benzothiazol-4-ylmethanesulfonylmethyl, benzothiazol-7-ylmethanesulfonylmethyl, 2-CF$_3$-benzothiazol-7-ylmethanesulfonylmethyl, [1,2]benzothiazol-3-ylmethanesulfonylmethyl, [1,2]benzothiazol-4-ylmethanesulfonylmethyl, 5-CF$_3$-[1,2]benzothiazol-4-ylmethanesulfonylmethyl, 3-CF$_3$-[1,2]benzothiazol-4-ylmethanesulfonylmethyl, 6-CF$_3$-[1,2]benzothiazol-7-ylmethanesulfonylmethyl, 6-CN-[1,2]benzothiazol-7-ylmethanesulfonylmethyl, 3-CF$_3$-[1,2]benzothiazol-7-ylmethanesulfonylmethyl, 5-F-[1,2]benzothiazol-3-ylmethanesulfonylmethyl, [2,3]benzothiazol-7-ylmethanesulfonylmethyl, 6-CF$_3$-[2,3]benzothiazol-7-ylmethane-sulfonylmethyl, 1-CF$_3$-[2,3]benzothiazol-7-ylmethanesulfonylmethyl, 5-CF$_3$-[2,3]benzothiazol-4-ylmethanesulfonylmethyl, 5-CN-[2,3]benzothiazol-4-ylmethanesulfonylmethyl, 1-CF$_3$-[2,3]benzothiazol-4-ylmethanesulfonylmethyl, 4-CF$_3$-2-CH$_3$-thiazol-5-ylmethanesulfonyl-methyl, 4-CF$_3$-thiazol-5-ylmethanesulfonylmethyl, 4-CF$_3$-2-phenyl-thiazol-5-ylmethanesulfonylmethyl, 5-CF$_3$-2-CH$_3$-thiazol-4-ylmethanesulfonylmethyl, 5-CF$_3$-thiazol-4-ylmethanesulfonylmethyl, 5-CF$_3$-2-phenyl-thiazol-4-ylmethanesulfonylmethyl, 5-CF$_3$-thiazol-2-ylmethanesulfonylmethyl, 5-CF$_3$-thiazol-2-ylmethanesulfonylmethyl, 5-phenyl-thiazol-2-ylmethanesulfonylmethyl, 4-CH$_3$-thiazol-2-ylmethanesulfonylmethyl, 4-CF$_3$-thiazol-2-ylmethanesulfonylmethyl, 4-phenyl-thiazol-2-ylmethanesulfonylmethyl, 5-CH$_3$-2-(pyridin-2-yl)-[1,2,3]triazol-4-ylmethanesulfonylmethyl, 5-CF$_3$-2-(pyridin-2-yl)-[1,2,3]triazol-4-ylmethanesulfonylmethyl, 5-CF$_3$-2-(4-methylsulfonylphenyl)-[1,2,3]triazol-4-ylmethane-sulfonylmethyl, 4,5-dimethyl-[1,2,4]triazol-3-ylmethanesulfonylmethyl, 5-CF$_3$-4-CH$_3$-[1,2,4]triazol-3-ylmethanesulfonylmethyl, 4-CH$_3$-5-phenyl-[1,2,4]triazol-3-ylmethane-sulfonylmethyl, 5-CF$_3$-4-cyclopropyl-[1,2,4]triazol-3-ylmethanesulfonylmethyl, 2,5-dimethyl-[1,2,4]triazol-ylmethanesulfonylmethyl, 5-CF$_3$-2-CH$_3$-[1,2,4]triazol-3-ylmethane-sulfonylmethyl, 2-CH$_3$-5-phenyl-[1,2,4]triazol-3-ylmethanesulfonylmethyl, 2-cyclopropyl-5-phenyl-[1,2,4]triazol-3-ylmethanesulfonylmethyl, 5-CF$_3$-1-CH$_3$-[1,2,4]triazol-3-ylmethane-sulfonylmethyl, 1-CH$_3$-5-phenyl-[1,2,4]triazol-3-ylmethanesulfonylmethyl, 5-CF$_3$-1-phenyl-[1,2,4]triazol-3-ylmethanesulfonylmethyl, 3-CH$_3$-[1,2,4]oxadiazol-5-ylmethanesulfonylmethyl 3-CF$_3$-[1,2,4]oxadiazol-5-ylmethanesulfonylmethyl, 3-phenyl-[1,2,4]oxadiazol-5-ylmethane-sulfonylmethyl, 5-CH$_3$-[1,2,4]oxadiazol-3-ylmethanesulfonylmethyl, 5-CF$_3$-[1,2,4]oxadiazol-3-ylmethanesulfonylmethyl, 5-phenyl-[1,2,4]oxadiazol-3-ylmethanesulfonylmethyl, 2-CH$_3$-[1,3,4]oxadiazol-5-ylmethanesulfonylmethyl, 2-CF$_3$-[1,3,4]oxadiazol-5-ylmethane-sulfonylmethyl, 2-phenyl-[1,3,4]oxadiazol-5-ylmethanesulfonylmethyl, 3-CH$_3$-[1,2,4]thiadiazol-5-ylmethanesulfonylmethyl, 3-CF$_3$-[1,2,4]thiadiazol-5-ylmethanesulfonylmethyl, 3-phenyl-[1,2,4]thiadiazol-5-ylmethanesulfonylmethyl, 5-CH$_3$-[1,2,4]thiadiazol-3-ylmethane-sulfonylmethyl, 5-CF$_3$-[1,2,4]thiadiazol-3-ylmethanesulfonylmethyl, 5-phenyl-[1,2,4]thiadiazol-3-ylmethanesulfonylmethyl, 2-CH$_3$-[1,3,4]thiadiazol-5-ylmethanesulfonylmethyl, 2-CF$_3$-[1,3,4]thiadiazol-5-ylmethanesulfonylmethyl, 2-phenyl-[1,3,4]thiadiazol-5-ylmethane-sulfonylmethyl, 2,2-difluoropyrrolidinylmethanesulfonylmethyl, 3,3-difluoropyrrolidinyl-methanesulfonylmethyl, 3-CF$_3$—N—CH$_3$-pyrrol-2-ylmethanesulfonylmethyl, 3-CN—N—CH$_3$-pyrrol-2-ylmethanesulfonylmethyl, 4-CF$_3$—N—CH$_3$-pyrrol-2-ylmethanesulfonylmethyl, 4-(1-CH$_3$-1-hydroxyethyl)-N—CH$_3$-pyrrol-2-ylmethanesulfonylmethyl, 1,3-dimethylpyrrol-2-ylmethanesulfonylmethyl, 4-CF$_3$—N—CH$_3$-pyrrol-3-ylmethanesulfonylmethyl, 4-CN—N—CH$_3$-pyrrol-3-ylmethanesulfonylmethyl, 4-CN—N-(3,3,3-trifluoropropyl)-pyrrol-3-ylmethanesulfonylmethyl, 2-CF$_3$—N—CH$_3$-pyrrol-3-ylmethanesulfonylmethyl, 2-CF$_3$—N-phenyl-pyrrol-3-ylmethane-sulfonylmethyl, 4-CF$_3$-pyrrol-2-ylmethanesulfonylmethyl, 4-(1-CH$_3$-1-hydroxyethyl)-pyrrol-2-ylmethanesulfonylmethyl, 3-CH$_3$-pyrrol-2-ylmethanesulfonylmethyl, 4-CF$_3$-pyrrol-3-ylmethane-sulfonylmethyl, 2-CF$_3$-pyrrol-3-ylmethanesulfonylmethyl, 3-CF$_3$-pyrrol-2-ylmethane-sulfonylmethyl, 2-CF$_3$-pyrrol-4-ylmethanesulfonylmethyl, 2-CF$_3$—N—CH$_3$-pyrrol-4-ylmethane-sulfonylmethyl, 3-CF$_3$-fur-2-ylmethanesulfonylmethyl, 3-CN-fur-2-ylmethanesulfonylmethyl, 3-CF$_3$-fur-4-ylmethanesulfonylmethyl, 3-CN-fur-4-ylmethanesulfonylmethyl, 2-CF$_3$-fur-3-ylmethanesulfonylmethyl, 3-CF$_3$-thiazol-2-ylmethanesulfonylmethyl, 3-CN-thiazol-2-ylmethanesulfonylmethyl, 3-CF$_3$-thiazol-4-ylmethanesulfonylmethyl, 3-CN-thiazol-4-ylmethanesulfonylmethyl, 2-CF$_3$-thiazol-3-ylmethanesulfonylmethyl, N—CH$_3$-3-CF$_3$-1H-pyrazol-5-ylmethanesulfonylmethyl, N—CH$_3$-3-(1-CH$_3$-1-hydroxyethyl)-1H-pyrazol-5-ylmethane-sulfonylmethyl, N—CH$_3$-3-phenyl-1H-pyrazol-5-ylmethanesulfonylmethyl, N—CH$_3$-3-CF$_3$-1H-pyrazol-4-ylmethanesulfonylmethyl, N—CH$_3$-4-CN-1H-pyrazol-3-ylmethanesulfonylmethyl, N-phenyl-4-CN-1H-pyrazol-3-ylmethanesulfonylmethyl, N-phenyl-3-CF$_3$-1H-pyrazol-4-ylmethanesulfonylmethyl, N-phenyl-5-CF$_3$-1H-pyrazol-4-ylmethanesulfonylmethyl, (N—CH$_3$-4-CF$_3$-1H-imidazol-2-ylmethane)-sulfonylmethyl, [N—CH$_3$-4-(1-CH$_3$-1-hydroxyethyl)-1H-imidazol-2-ylmethane]-sulfonylmethyl, (N—CH$_3$-4-phenyl-1H-imidazol-2-ylmethane)-sulfonylmethyl, N—CH$_3$-3-CF$_3$-1H-pyrazol-4-ylmethanesulfonylmethyl, (N—CH$_3$-2-CF$_3$-1H-imidazol-5-ylmethane)-sulfonylmethyl, (N—CH$_3$-2-phenyl-1H-imidazol-5-ylmethane)-sulfonylmethyl, (N—CH$_3$-5-CF$_3$-1H-imidazol-4-ylmethane)-sulfonylmethyl, (N-phenyl-5-CF$_3$-1H-imidazol-4-ylmethane)-sulfonylmethyl, 4-CN-[1,2]oxazol-5-ylmethanesulfonylmethyl 4-CN-3-phenyl-[1,2]oxazol-5-ylmethanesulfonylmethyl, 4-CN-[1,2]oxazol-3-ylmethanesulfonylmethyl, 4-CN-5-phenyl-[1,2]oxazol-3-ylmethanesulfonylmethyl, 4-CN-isothiazol-5-ylmethanesulfonylmethyl, 4-CN-3-phenyl-isothiazol-5-ylmethanesulfonylmethyl, 4-CN-isothiazol-3-ylmethanesulfonylmethyl, 4-CN-5-phenyl-isothiazol-3-ylmethane-sulfonylmethyl, 4-CF$_3$-[1,2]oxazol-5-ylmethanesulfonylmethyl, 4-CF$_3$-3-CH$_3$-[1,2]oxazol-5-ylmethanesulfonylmethyl, 4-CF$_3$-3-phenyl-[1,2]oxazol-5-ylmethanesulfonylmethyl, 4-CF$_3$-[1,2]oxazol-3-ylmethanesulfonylmethyl, 4-CF$_3$-5-CH$_3$-[1,2]oxazol-3-ylmethanesulfonylmethyl 4-CF$_3$-5-phenyl-[1,2]oxazol-3-ylmethanesulfonylmethyl. 3-CF$_3$-[1,2]oxazol-4-ylmethane-sulfonylmethyl, 5-CF$_3$-[1,2]oxazol-4-ylmethanesulfonylmethyl, 4-CF$_3$-[1,2]oxazol-5-ylmethanesulfonylmethyl, 4-CF$_3$-3-CH$_3$-[1,2]oxazol-5-ylmethanesulfonylmethyl, 4-CF$_3$-3-phenyl-[1,2]oxazol-5-ylmethanesulfonylmethyl, 4-CF$_3$-[1,2]oxazol-3-ylmethanesulfonylmethyl, 4-CF$_3$-5-CH$_3$-[1,2]oxazol-3-ylmethanesulfonylmethyl, 4-CF$_3$-5-phenyl-[1,2]oxazol-3-ylmethanesulfonylmethyl, 3-CF$_3$-[1,2]oxazol-4-ylmethanesulfonylmethyl, 5-CF$_3$-[1,2]oxazol-4-ylmethanesulfonylmethyl, 4-CH$_3$-[1,2]oxazol-5-ylmethanesulfonylmethyl, 4-CH$_3$-3-phenyl-[1,2]oxazol-5-ylmethanesulfonylmethyl, 4-CH$_3$-[1,2]oxazol-3- ylmethanesulfonylmethyl, 4-CH₃-5-phenyl-[1,2]oxazol-3-ylmethanesulfonylmethyl, 3-CH₃-[1,2]oxazol-4-ylmethanesulfonylmethyl, 5-CH₃-[1,2]oxazol-4-ylmethanesulfonylmethyl, 4-CH₃-isothiazol-5-ylmethanesulfonylmethyl, 4-CH₃-3-phenyl-isothiazol-5-ylmethanesulfonylmethyl, 4-CH₃-isothiazol-3-ylmethanesulfonylmethyl, 4-CH₃-5-phenyl-isothiazol-3-ylmethanesulfonylmethyl, 3-CH₃-isothiazol-4-ylmethanesulfonylmethyl, 5-CH₃-isothiazol-4-ylmethanesulfonylmethyl, 4-CF₃-2-CH₃-[1,3]oxazol-5-ylmethanesulfonylmethyl, 4-CF₃-[1,3]oxazol-5-ylmethanesulfonylmethyl, 4-CF₃-2-phenyl-[1,3]oxazol-5-ylmethanesulfonylmethyl, 5-CF₃-2-CH₃-[1,3]oxazol-4-ylmethanesulfonylmethyl, 5-CF₃-[1,3]oxazol-4-ylmethanesulfonylmethyl, 5-CF₃-2-phenyl-[1,3]oxazol-4-ylmethanesulfonylmethyl, 5-CH₃-[1,3]oxazol-2-ylmethanesulfonylmethyl, 5-CF₃-[1,3]oxazol-2-ylmethanesulfonylmethyl, 5-phenyl-[1,3]oxazol-2-ylmethane-sulfonylmethyl, 4-CH₃-[1,3]oxazol-2-ylmethanesulfonylmethyl, 4-CF₃-[1,3]oxazol-2-ylmethanesulfonylmethyl, 4-phenyl-[1,3]oxazol-2-ylmethanesulfonylmethyl, N-methyl-indol-2-ylmethanesulfonylmethyl, 3-CF₃-indol-2-ylmethanesulfonylmethyl, 3-CF₃—N-methyl-indol-2-ylmethanesulfonylmethyl, 5-fluoro-N-methyl-indol-2-ylmethanesulfonylmethyl, N-methyl-indol-3-ylmethanesulfonylmethyl, 2-CF₃-indol-3-ylmethanesulfonylmethyl, 2-CF₃—N-methyl-indol-3-ylmethanesulfonylmethyl, 5-fluoro-N-methyl-indol-3-ylmethanesulfonylmethyl, 5-CF₃—N-methyl-indol-4-ylmethanesulfonylmethyl, 5-CN—N-methyl-indol-4-ylmethanesulfonylmethyl, 2-CF₃—N-methyl-indol-4-ylmethanesulfonylmethyl, 3-CF₃—N-methyl-indol-4-ylmethanesulfonylmethyl, 6-CF₃—N-methyl-indol-7-ylmethanesulfonylmethyl, 6-CN—N-methyl-indol-7-ylmethanesulfonylmethyl, 2-CF₃—N-methyl-indol-7-ylmethanesulfonylmethyl, 3-CF₃—N-methyl-indol-7-ylmethanesulfonylmethyl, benzofuran-2-ylmethanesulfonylmethyl, 3-CF₃-benzofuran-2-ylmethanesulfonylmethyl, 3-CN-benzofuran-2-ylmethanesulfonylmethyl, 5-F-benzofuran-2-ylmethanesulfonylmethyl, benzofuran-3-ylmethanesulfonylmethyl, 2-CF₃-benzofuran-3-ylmethanesulfonylmethyl, 2-CH₃-benzofuran-3-ylmethanesulfonylmethyl,5-F-benzofuran-3-ylmethanesulfonylmethyl, 5-CF₃-benzofuran-4-ylmethanesulfonylmethyl, 5-CN-benzofuran-4-ylmethanesulfonylmethyl, 2-CF₃-benzofuran-4-ylmethanesulfonylmethyl, 3-CF₃-benzofuran-4-ylmethanesulfonylmethyl, 6-CF₃-benzofuran-7-ylmethanesulfonylmethyl, 6-CN-benzofuran-7-ylmethanesulfonylmethyl, 2-CF₃-benzofuran-7-ylmethanesulfonylmethyl, 3-CF₃-benzofuran-7-ylmethanesulfonylmethyl, benzothien-2-ylmethanesulfonylmethyl, (3-CF₃-benzothien-2-ylmethane)-sulfonylmethyl, (3-CN-benzothien-2-ylmethane)-sulfonylmethyl, (5-F-benzothien-2-ylmethane)-sulfonylmethyl, benzothien-3-ylmethanesulfonylmethyl, (2-CF₃-benzothien-3-ylmethane)-sulfonylmethyl, (2-CH₃-benzothien-3-ylmethane)-sulfonylmethyl, (5-fluoro-benzothien-3-ylmethane)-sulfonylmethyl, (5-CF₃-benzothien-4-ylmethane)-sulfonylmethyl, (5-CN-benzothien-4-ylmethane)-sulfonylmethyl, (2-CF₃-benzothien-4-ylmethane)-sulfonylmethyl, (3-CF₃-benzothien-4-ylmethane)-sulfonylmethyl, (6-CF₃-benzothien-7-ylmethane)-sulfonylmethyl, (6-CN-benzothien-7-ylmethane)-sulfonylmethyl, (2-CF₃-benzothien-7-ylmethane)-sulfonylmethyl, (3-CF₃-benzothien-7-ylmethane)-sulfonylmethyl, N-methyl-benzimidazol-2-ylmethanesulfonylmethyl, (5-fluoro-N-methyl-benzimidazol-2-ylmethane)-sulfonylmethyl, (N-methyl-indazol-3-ylmethane)-sulfonylmethyl, (5-fluoro-N-methyl-indazol-3-ylmethane)-sulfonylmethyl, (2-CF₃—N-methyl-benzimidazol-4-ylmethane)-sulfonylmethyl, (2-CF₃—N-methyl-benzimidazol-7-ylmethane)-sulfonylmethyl, (N-methyl-indazol-4-ylmethane)-sulfonylmethyl, (5-CF₃—N-methyl-indazol-4-ylmethane)-sulfonylmethyl, (3-CF₃—N-methyl-indazol-4-ylmethane)-sulfonylmethyl, (6-CF₃—N-methyl-indazol-7-ylmethane)-sulfonylmethyl, (6-CN—N-methyl-indazol-7-ylmethane)-sulfonylmethyl, or (3-CF₃—N-methyl-indazol-7-ylmethane)-sulfonylmethyl.

Within the groups above, the stereochemistry at the carbon to which $R^5$ is attached is (R) and to which $R^4$ and $R^6$ are attached is (S).

Within the groups above, the stereochemistry at the carbon to which $R^5$ and $R^6$ are attached is (R) and to which $R^4$ is attached is (S).

(B) Another preferred group of compounds of Formula (I) is that wherein:

$R^3$ is alkyl, preferably methyl or ethyl and $R^4$ is alkyl, preferably methyl, ethyl, propyl or butyl, more preferably $R^4$ is methyl. Preferably, $R^3$ and $R^4$ are methyl.

(C) Yet another preferred group of compounds of Formula (I) is that wherein $R^3$ and $R^4$ together with the carbon atom to which they are attached form cycloalkylene, preferably cyclopropylene, cyclopentylene, or cyclohexylene, more preferably cyclopropylene.

(D) Yet another preferred group of compounds of Formula (I) is that wherein $R^3$ and $R^4$ together with the carbon atom to which they are attached form piperidin-4-yl substituted at the nitrogen atom with ethyl, 2,2,2-trifluoroethyl or cyclopropyl, tetrahydropyran-4-yl, tetrahydrothiopyran-4-yl, or 1,1-dioxotetrahydrothiopyran-4-yl.

(E) Yet another preferred group of compounds of Formula (I) is that wherein $R^6$ is haloalkyl, preferably, difluoromethyl, trifluoromethyl, 2,2,2-trifluoroethyl, or 1,1,2,2,2-pentafluoroethyl and $R^7$ and $R^8$ are hydrogen.

(F) Yet another preferred group of compounds of Formula (I) is that wherein $R^6$ is haloalkyl, preferably, difluoromethyl, trifluoromethyl, 2,2,2-trifluoroethyl, or 1,1,2,2,2-pentafluoroethyl, $R^7$ is haloalkyl, preferably, trifluoromethyl, 2,2,2-trifluoroethyl, or 1,1,2,2,2-pentafluoroethyl, and $R^8$ are hydrogen.

(G) Yet another preferred group of compounds of Formula (I) is that wherein $R^6$ is haloalkyl, preferably, difluoromethyl, trifluoromethyl, 2,2,2-trifluoroethyl, or 1,1,2,2,2-pentafluoroethyl, $R^7$ is alkyl, preferably, methyl, ethyl, or propyl, and $R^8$ are hydrogen.

(H) Yet another preferred group of compounds of Formula (I) is that wherein $R^6$ is haloalkyl, preferably, 1,1,2,2,2-pentafluoroethyl or 1,1,2,2,3,3,3-heptafluoropropyl, $R^7$ and $R^8$ are hydrogen.

With the preferred groups (B)-(H), more preferred groups of compounds are those wherein $R^1$, $R^2$, $R^5$, $R^6$, $R^7$ and $R^8$ are as defined for group (A) above.

With the preferred groups (D)-(H), more preferred groups of compounds are those wherein $R^1$, $R^2$, $R^3$, $R^4$, and $R^5$ are as defined for group (A) above.

It should be noted that reference to the preferred embodiments set forth above includes all combinations of particular and preferred groups unless stated otherwise.

Representative compound of the compound of Formula (I) where $R^1$ is hydrogen, $R^6$ is trifluoromethyl and other groups are as defined in Table I below are:

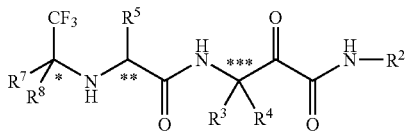

| Cpd. # | Stereochem. at *C,C,*C | R2 | R3 | R4 | R3 + R4 | R5 | R7 | R8 |
|---|---|---|---|---|---|---|---|---|
| 1 | (S,R,S) | cyclopropyl | H | n-propyl | | cyclopropylmethanesulfonylmethyl | H | 4-Fphenyl |
| 2 | (S,R,S) | cyclopropyl | H | n-propyl | | pyridin-3-ylmethanesulfonyl-methyl | H | 4-Fphenyl |
| 3 | (R,R,S) | cyclopropyl | H | n-propyl | | cyclopropylmethanesulfonylmethyl | H | 4-Fphenyl |
| 4 | (*S,**R) | cyclopropyl | | | cyclopropylene | cyclopropylmethanesulfonylmethyl | H | 4-Fphenyl |
| 5 | (*S,**R) | cyclopropyl | CH3 | CH3 | | cyclopropylmethanesulfonylmethyl | H | 4-Fphenyl |
| 6 | (R,*S) | cyclopropyl | H | ethyl | | cyclopropylmethanesulfonylmethyl | H | H |
| 7 | (*S,**R) | cyclopropyl | | | cyclopropylene | pyridin-3-ylmethanesulfonyl-methyl | H | 4-Fphenyl |
| 8 | (R,R,S) | cyclopropyl | H | ethyl | | 4-CF3pyridin-3-ylmethane-sulfonylmethyl | H | 4-Fphenyl |
| 9 | (S,R,S) | cyclohexyl | H | ethyl | | cyclopropylmethanesulfonylmethyl | H | 4-Fphenyl |
| 10 | (S,R,S) | benzyl | H | ethyl | | cyclopropylmethanesulfonylmethyl | H | 4-Fphenyl |
| 11 | (*S,**R) | benzyl | CH3 | CH3 | | pyridin-3-ylmethanesulfonylmethyl | H | 4-Fphenyl |
| 12 | (*S,**R) | cyclopropyl | CH3 | CH3 | | pyridin-3-ylmethanesulfonylmethyl | H | 4-Fphenyl |
| 13 | (*S,**R) | benzyl | CH3 | CH3 | | cyclopropylmethanesulfonylmethyl | H | 4-Fphenyl |
| 14 | (*R,**R) | benzyl | CH3 | CH3 | | cyclopropylmethanesulfonylmethyl | H | 4-Fphenyl |
| 15 | (*S,**R) | benzyl | CH3 | CH3 | | cyclopropylmethanesulfonylmethyl | H | 4-Fphenyl |
| 16 | (R,R,S) | cyclopropyl | H | ethyl | | pyridin-3-ylmethanesulfonylmethyl | H | 4-Fphenyl |
| 17 | (S,R,S) | cyclopropyl | H | ethyl | | pyridin-2-ylmethanesulfonylmethyl | H | 3,4-diFphenyl |
| 18 | (*S,**R) | cyclopropyl | CH3 | CH3 | | 4-CF3pyridin-3-ylmethane-sulfonylmethyl | H | 4-Fphenyl |
| 19 | (S,R,S) | cyclopropyl | H | ethyl | | 2-pyridin-2-ylethanesulfonylmethyl | H | 4-Fphenyl |
| 20 | (*S,**R) | cyclopropyl | CH3 | CH3 | | 2-pyridin-2-ylethanesulfonylmethyl | H | 4-Fphenyl |
| 21 | (*S,**R) | cyclopropyl | | | cyclopropyl | 2-pyridin-2-ylethanesulfonylmethyl | H | 4-Fphenyl |
| 22 | (*S,**R) | cyclopropyl | | | cyclopropyl | 4-CF3pyridin-3-ylmethane-sulfonylmethyl | H | 4-Fphenyl |
| 23 | (*S,**R) | cyclopropyl | CH3 | CH3 | | pyridin-3-ylmethanesulfonylmethyl | H | 2,4-diFphenyl |
| 24 | (*R,**R) | cyclopropyl | CH3 | CH3 | | pyridin-3-ylmethanesulfonylmethyl | H | 2,4-diFphenyl |
| 25 | (*S,**R) | cyclopropyl | | | cyclopropyl | pyridin-3-ylmethanesulfonylmethyl | H | 2,4-diFphenyl |
| 26 | (*R,**R) | cyclopropyl | | | cyclopropyl | pyridin-3-ylmethanesulfonylmethyl | H | 2,4-diFphenyl |
| 27 | (*S,**R) | cyclopropyl | | | cyclopropyl | 1-oxopyridin-3-ylmethane-sulfonylmethyl | H | 2,4-diFphenyl |
| 28 | (*R,**R) | cyclopropyl | | | cyclopropyl | 1-oxopyridin-3-ylmethane-sulfonylmethyl | H | 2,4-diFphenyl |
| 29 | (*S,**R) | cyclopropyl | CH3 | CH3 | | 4-CNpyridin-3-ylmethane-sulfonylmethyl | H | 4-Fphenyl |
| 30 | (S,R,S) | cyclopropyl | H | ethyl | | 2-(2,3-dioxoindol-1-yl)-ethanesulfonylmethyl | H | 4-Fphenyl |
| 31 | (*S,**R) | cyclopropyl | | | cyclohexyl | pyridin-3-ylmethanesulfonylmethyl | H | 4-Fphenyl |
| 32 | (R,*S) | cyclopropyl | CH3 | CH3 | | 2-cyanophenylmethanesulfonylmethyl | H | H |
| 33 | (*S,**R) | cyclopropyl | CH3 | CH3 | | 2-CH3SO2phenylmethane-sulfonylmethyl | H | 4-F-phenyl |
| 34 | (*S,**R) | cyclopropyl | CH3 | CH3 | | 2-(2-oxoimidazolidin-1-yl)-ethylsulfonylmethyl | H | 4-F-phenyl |
| 35 | (S,R,S) | cyclopropyl | H | ethyl | | phenylsulfonylmethyl | H | 4-F-phenyl |
| 36 | (*S,**R) | cyclopropyl | CH3 | CH3 | | 3-CH3SO2phenylmethanesulfonylmethyl | H | 4-F-phenyl |
| 37 | (S,R,S) | cyclopropyl | H | ethyl | | 2-cyclopropylmethanesulfonylethyl | H | 4-F-phenyl |
| 38 | (*S,**R) | cyclopropyl | CH3 | CH3 | | 4-CH3SO2phenylmethanesulfonylmethyl | H | 4-F-phenyl |
| 39 | (S,R,S) | cyclopropyl | H | cyclobutylmethyl | | cyclopropylmethanesulfonylmethyl | H | 4-F-phenyl |
| 40 | (*S,**R) | cyclopropyl | | | cyclopropylene | 2-cyanophenylmethanesulfonylmethyl | H | 4-Fphenyl |
| 41 | (*S,**R) | cyclopropyl | CH3 | CH3 | | 2-cyanophenylmethanesulfonylmethyl | H | 4-Fphenyl |
| 42 | (*S,R,*S) | cyclopropyl | H | ethyl | | 4-(4-fluorobenzoyl)-piperazin-1-ylsulfonylmethyl | H | 4-Fphenyl |
| 43 | (*S,**R) | cyclopropyl | CH3 | CH3 | | 4-(4-fluorobenzoyl)-piperazin-1-ylsulfonylmethyl | H | 4-Fphenyl |
| 44 | (*S,S,*S) | cyclopropyl | H | ethyl | | 2-chlorobenzyl | H | 4-Fphenyl |
| 45 | (*S,R,*S) | cyclopropyl | H | ethyl | | biphenyl-4-ylsulfonylmethyl | H | 4-Fphenyl |
| 46 | (*S,R,*S) | cyclopropyl | H | ethyl | | 3-trifluoromethylphenylsulfonylmethyl | H | 4-Fphenyl |
| 47 | (*S,R,*S) | cyclopropyl | H | ethyl | | 3-methylsulfonylbenzylsulfonylmethyl | H | 4-Fphenyl |
| 48 | (*S,R,*S) | cyclopropyl | H | ethyl | | cyclopropylmethanesulfonylmethyl | H | 4-Fphenyl |
| 49 | (*S,R,*S) | cyclopropyl | H | ethyl | | 4-trifluorophenylsulfonylmethyl | H | 4-Fphenyl |
| 50 | (*S,R,*S) | cyclopropyl | H | ethyl | | 4-methylsulfonylphenylsulfonylmethyl | H | 4-Fphenyl |
| 51 | (*S,S,*S) | cyclopropyl | H | ethyl | | 2-cyclohexylethyl | H | 4-Fphenyl |
| 52 | (*S,R,*S) | cyclopropyl | H | ethyl | | pyrid-3-ylmethylsulfonylmethyl | H | 4-Fphenyl |

-continued

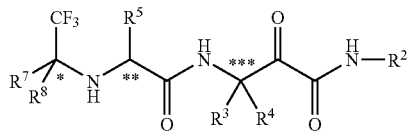

| Cpd. # | Stereochem. at *C,C,*C | R² | R³ | R⁴ | R³ + R⁴ | R⁵ | R⁷ | R⁸ |
|---|---|---|---|---|---|---|---|---|
| 53 | (S,*S) | cyclopropyl | H | ethyl | | benzyloxymethyl | H | 4-Fphenyl |
| 54 | (*S,R,*S) | cyclopropyl | H | ethyl | | naphth-2-ylsulfonylmethyl | H | 4-Fphenyl |
| 55 | (*S,S,*S) | cyclopropyl | H | ethyl | | 2-phenylsulfonylethyl | H | 4-Fphenyl |
| 56 | (*S,S,*S) | cyclopropyl | H | ethyl | | tert-butylmethyl | H | 4-Fphenyl |
| 57 | (*S,R,*S) | cyclopropyl | H | ethyl | | pyrid-3-ylsulfonylmethyl | H | 4-Fphenyl |
| 58 | (*S,R,*S) | cyclopropyl | H | ethyl | | morpholin-4-ylsulfonylmethyl | H | 4-Fphenyl |
| 59 | (*S,R,*S) | cyclopropyl | H | ethyl | | phenylsulfonylmethyl | H | phenyl |
| 60 | (*S,R,*S) | cyclopropyl | H | ethyl | | naphth-1-ylsulfonylmethyl | H | 4-Fphenyl |
| 61 | (*S,S,*S) | cyclopropyl | H | ethyl | | 3,3-dimethylpentyl | H | 4-Fphenyl |
| 62 | (R,*S) | cyclopropyl | H | ethyl | | cyclopropylmethylsulfonylmethyl | H | tetrahydro-pyran-4-yl |
| 63 | (*S,R,*S) | cyclopropyl | H | ethyl | | 3,5-trifluoromethylphenylsulfonylmethyl | H | 4-Fphenyl |
| 64 | (*S,R,*S) | cyclopropyl | H | ethyl | | quinolin-3-ylsulfonylmethyl | H | 4-Fphenyl |
| 65 | (*S,R,*S) | cyclopropyl | H | ethyl | | pyrid-4-ylsulfonylmethyl | H | 4-Fphenyl |
| 66 | (*S,S,*S) | cyclopropyl | H | ethyl | | 2,2-difluoro-3-phenylpropyl | H | 4-Fphenyl |
| 67 | (*S,S,*S) | cyclopropyl | H | ethyl | | 2,2,2-trifluoroethyl | H | 4-Fphenyl |
| 68 | (*S,R,*S) | cyclopropyl | H | ethyl | | 3-methoxyphenylsulfonylmethyl | H | 4-Fphenyl |
| 69 | (*S,R,*S) | cyclopropyl | H | ethyl | | 4-methoxyphenylsulfonylmethyl | H | 4-Fphenyl |
| 70 | (*S,R,*S) | cyclopropyl | H | ethyl | | 2-methoxyphenylsulfonylmethyl | H | 4-Fphenyl |
| 71 | (*S,R,*S) | cyclopropyl | H | ethyl | | isoquinolin-4-ylsulfonylmethyl | H | 4-Fphenyl |
| 72 | (*S,R,*R) | cyclopropyl | H | ethyl | | phenylsulfonylmethyl | H | 4-Fphenyl |
| 73 | (*S,S,*S) | cyclopropyl | H | ethyl | | isobutyl | H | 4-Fphenyl |
| 74 | (*S,R,*R) | pyrazol-3-yl | H | ethyl | | cyclopropylmethylsulfonylmethyl | H | 4-Fphenyl |
| 75 | (*S,S,*R) | cyclopropyl | H | ethyl | | benzyl | H | 4-Fphenyl |
| 76 | (*S,R,*R) | cyclopropyl | H | ethyl | | cyclopropylmethylsulfonylmethyl | H | tetrahydro-pyran-4-yl |
| 77 | (*S,R,*R) | cyclopropyl | H | ethyl | | phenylsulfonylmethyl | H | tetrahydro-pyran-4-yl |
| 78 | (*S,S,*S) | cyclopropyl | H | ethyl | | 2-methanesulfonylethyl | H | 4-Fphenyl |
| 79 | (*S,S,*S) | cyclopropyl | H | ethyl | | cyclopropylmethyl | H | 4-Fphenyl |
| 80 | (*S,S,*S) | cyclopropyl | H | ethyl | | cyclopropylmethyl | H | tetrahydro-pyran-4-yl |
| 81 | (*S,S,*S) | cyclopropyl | H | ethyl | | 2,2-difluoro-4-methylpentyl | H | 4-Fphenyl |
| 82 | (*S,S,*S) | cyclopropyl | H | ethyl | | phenylsulfonylaminomethyl | H | 4-Fphenyl |
| 83 | (*S,S,*S) | cyclopropyl | H | ethyl | | isopropylsulfonylaminomethyl | H | 4-Fphenyl |
| 84 | (*S,S,*S) | cyclopropyl | H | ethyl | | methylsulfonylaminomethyl | H | 4-Fphenyl |
| 85 | (*S,S,*S) | cyclopropyl | H | ethyl | | 2-(4-trifluoromethyl-phenylsulfonyl)ethyl | H | 4-Fphenyl |
| 86 | (*S,S,*S) | cyclopropyl | H | ethyl | | 2-(4-trifluoromethylphenylsulfanyl)ethyl | H | 4-Fphenyl |
| 87 | (*S,S,*S) | cyclopropyl | H | ethyl | | 2-methylsulfinylethyl | H | 4-Fphenyl |
| 88 | (*S,S,*S) | cyclopropyl | H | ethyl | | 2-pyrid-3-ylsulfonylethyl | H | 4-Fphenyl |
| 89 | (*S,S,*S) | cyclopropyl | H | ethyl | | 3-phenylpropyl | H | 4-Fphenyl |
| 90 | (*S,S,*S) | cyclopropyl | H | ethyl | | 2-(4-methylsulfonylphenylsulfonyl)ethyl | H | 4-Fphenyl |
| 91 | (*S,S,*S) | cyclopropyl | H | ethyl | | 1-(tert-butoxycarbonyl)-piperidin-4-ylmethyl | H | 4-Fphenyl |
| 92 | (*S,S,*S) | cyclopropyl | H | ethyl | | 2-chlorobenzyl | H | 4-Fphenyl |
| 93 | (*S,S,*S) | cyclopropyl | H | ethyl | | 2,2-difluoro-2-phenylethyl | H | tetrahydro-pyran-4-yl |
| 94 | (*S,S,*S) | cyclopropyl | H | ethyl | | 1-methylsulfonylpiperidin-4-ylmethyl | H | 4-Fphenyl |
| 95 | (*S,S,*S) | cyclopropyl | H | ethyl | | 1-aminocarbonylpiperidin-4-ylmethyl | H | 4-Fphenyl |
| 96 | (*S,S,*S) | cyclopropyl | H | ethyl | | 1-methylcyclopentylmethyl | H | 4-Fphenyl |
| 97 | (*S,S,*S) | pyrazol-3-yl | H | ethyl | | 1-methylcyclopentylmethyl | H | 4-Fphenyl |
| 98 | (*S,S,*S) | cyclopropyl | H | ethyl | | 1-methylcyclopentylmethyl | H | tetrahydro-pyran-4-yl |

Representative compound of the compound of Formula (I) where $R^1$, $R^7$ and $R^8$ are hydrogen and other groups are as defined in Table II below are:

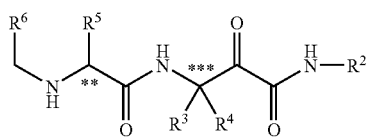

| Cpd. # | Stereochem. At C*C | $R^2$ | $R^3$ | $R^4$ | $R^3 + R^4$ | $R^5$ | $R^6$ |
|---|---|---|---|---|---|---|---|
| 1 | (R,*S) | cyclopropyl | H | ethyl | | pyridine-3-ylmethanesulfonylmethyl | 1,1,2,2,2-pentafluoroethyl |
| 2 | (R,*S) | cyclopropyl | H | ethyl | | cyclopropylmethanesulfonyl-methyl | 1,1,2,2,2-pentafluoroethyl |
| 3 | (R,*S) | cyclopropyl | H | ethyl | | pyridine-3-ylmethanesulfonyl-methyl | trifluoromethyl |
| 4 | (R,*S) | cyclopropyl | H | n-propyl | | cyclopropylmethanesulfonyl-methyl | 1,1,2,2,2-pentafluoroethyl |
| 5 | (R,*S) | cyclopropyl | H | n-propyl | | pyridine-3-ylmethanesulfonylmethyl | 1,1,2,2,2-pentafluoroethyl |
| 6 | (R,*S) | cyclopropyl | H | ethyl | | cyclopropylmethanesulfonyl-methyl | 1,1,2,2,-tetrafluoroethyl |
| 7 | (R,*S) | cyclopropyl | H | ethyl | | pyridine-3-ylmethanesulfonyl-methyl | 1,1,2,2,-tetrafluoroethyl |
| 8 | (R,*S) | cyclopropyl | H | ethyl | | cyclopropylmethanesulfonylmethyl | 1,1,2,2,3,3,3-heptafluoropropyl |
| 7 | (R,*S) | cyclopropyl | H | ethyl | | pyridine-3-ylmethanesulfonyl-methyl | 1,1,2,2,3,3,3-heptafluoropropyl |
| 8 | (R,*S) | cyclopropyl | H | ethyl | | 4-$CF_3$pyridin-3-ylmethane-sulfonylmethyl | 1,1,2,2,2-pentafluoroethyl |
| 9 | (R,*S) | cyclopropyl | H | ethyl | | 2-(cyclopropylmethanesulfonyl)-ethyl | 1,1,2,2,2-pentafluoroethyl |
| 10 | (R,*S) | cyclopropyl | H | ethyl | | 2-(pyridine-3-ylmethanesulfonyl)-ethyl | 1,1,2,2,2-pentafluoroethyl |
| 11 | (R,*S) | cyclopropyl | H | ethyl | | 2-(cyclopropylmethanesulfonyl)-ethyl | trifluoromethyl |
| 12 | (R,*S) | cyclopropyl | H | ethyl | | cyclopropylmethanesulfonylmethyl | chlorodifluoromethyl |
| 13 | (R,*S) | cyclopropyl | H | ethyl | | cyclopropylmethanesulfonylmethyl | —$(CF_2)_3CHF_2$ |
| 14 | (R,*S) | cyclopropyl | H | ethyl | | pyridine-3-ylmethanesulfonylmethyl | —$(CF_2)_3CHF_2$ |
| 15 | (R,*S) | cyclopropyl | H | ethyl | | piperidin-1-ylsulfonylmethyl | trifluoromethyl |
| 16 | (R,*S) | cyclopropyl | H | ethyl | | cyclopropylmethanesulfonylmethyl | perfluoropentyl |
| 17 | (**R) | cyclopropyl | H | ethyl | | cyclopropylmethanesulfonylmethyl | 1,1,2,2,3,3-hexafluoropropyl |
| 18 | (R,*S) | cyclopropyl | $CH_3$ | $CH_3$ | | 2-methylsulfonylbenzylsulfonylmethyl | trifluoromethyl |
| 19 | (R,*S) | cyclopropyl | $CH_3$ | $CH_3$ | | 3-methylsulfonylbenzylsulfonylmethyl | trifluoromethyl |
| 20 | (R,*S) | cyclopropyl | H | cyclobutyl-methyl | | cyclopropylmethanesulfonylmethyl | perfluoropropyl |
| 21 | (R,*S) | cyclopropyl | H | ethyl | | pyrid-2-ylmethanesulfonylmethyl | 1,1,2,2,3,3,4,4-octafluorobutyl |
| 22 | (R,*S) | cyclopropyl | H | ethyl | | pyrid-2-ylmethanesulfonylmethyl | 1,1,2,2,3,3-hexafluorobutyl |
| 23 | (R,*S) | cyclopropyl | H | ethyl | | pyrid-3-ylmethanesulfonylmethyl | 1,1,2,2,3,3-hexafluorobutyl |

The following represent compounds of the invention.

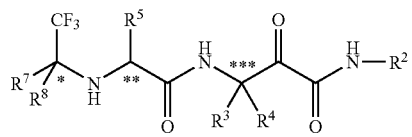

| Cpd. # | Stereochem. at *C,C,*C | $R^2$ | $R^3$ | $R^4$ | $R^3 + R^4$ | $R^5$ | $R^7$ | $R^8$ |
|---|---|---|---|---|---|---|---|---|
| 1 | (*S,**R) | cyclopropyl | | | cyclopropylene | 4-$CF_3$-pyridin-3-ylmethane-sulfonylmethyl | H | 4-Fphenyl |
| 2 | (*S,**R) | cyclopropyl | $CH_3$ | $CH_3$ | | 4-$CF_3$-pyridin-3-ylmethane-sulfonylmethyl | H | 4-Fphenyl |
| 3 | (*S,**R) | cyclopropyl | $CH_3$ | $CH_3$ | | 4-$CF_3$-pyridin-3-ylmethane-sulfonylmethyl | H | 2,4-diFphenyl |
| 4 | (*S,**R) | cyclopropyl | $CH_3$ | $CH_3$ | | pyridin-3-ylmethanesulfonylmethyl | H | 2,4-diFphenyl |
| 5 | (*S,**R) | cyclopropyl | | | cyclopropylene | 4-$CF_3$-pyridin-3-ylmethane-sulfonylmethyl | H | 2,4-diFphenyl |
| 6 | (*S,**R) | cyclopropyl | | | cyclopropylene | pyridin-3-ylmethanesulfonylmethyl | H | 2,4-diFphenyl |

General Synthetic Scheme

Compounds of this invention can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *"Protective Groups in Organic Chemistry"* John Wiley and Sons, 1999.

Compounds of Formula (I) where $R^1$, $R^2$, $R^3$, $R^4$, $R^5$, $R^6$ and $R^8$ are as defined in the Summary of the Invention and $R^7$ is hydrogen can be prepared by proceeding as in the following Reaction Scheme 1 below.

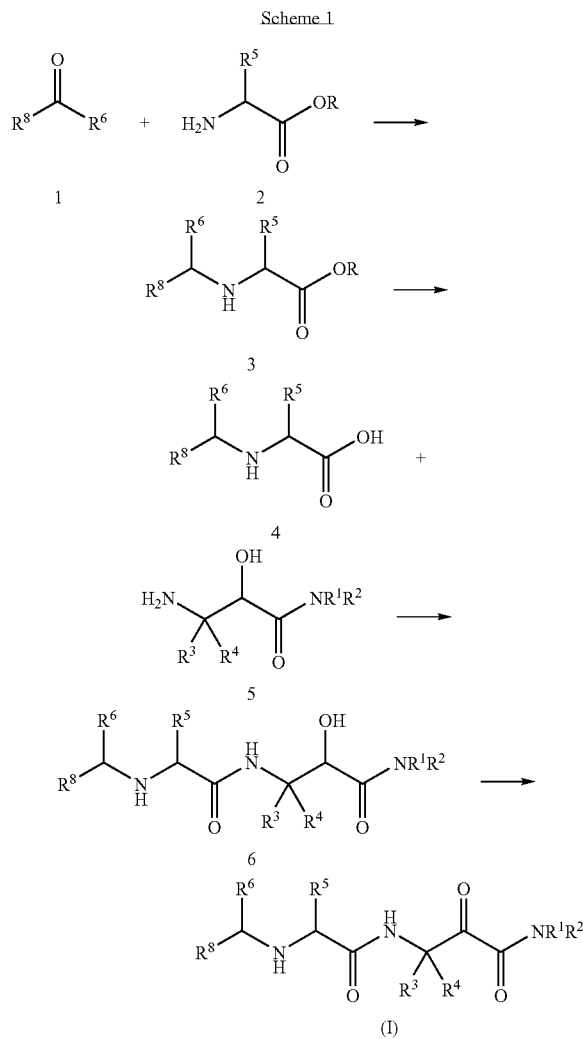

Reaction of a ketone of formula 1 where $R^6$ and $R^8$ are as defined in the Summary of the Invention with an α-amino ester of formula 2 where R is a carboxy protecting group, preferably an alkyl group, preferably methyl, and $R^5$ is as defined in the Summary of the Invention under reductive amination reaction conditions provide a compound of formula 3. The reaction is carried out in the presence of a suitable dehydrating agent such as $TiCl_4$, magnesium sulfate, isopropyl trifluoroacetate, in the presence of a base such as diisopropylethylamine, pyridine, and the like and in a suitable organic solvent such as methylene chloride to give an imine. The imine is reduced with a suitable reducing agent such as sodium borohydride, sodium cyanoborohydride, and the like in a suitable organic solvent such as methanol, ethanol, and the like.

Compounds of formula 1 such as 2,2,2-trifluoromethylacetophenone and 2,2,2,4'-tetrafluoroacetophenone are commercially available. Others can be prepared by methods well known in the art. α-Amino esters of formula 2 can be prepared by methods well known in the art e.g., PCT Applications Publication Nos. WO 03075836, WO 00/55144, WO 01/19816, WO 02/20485, WO 03/029200, U.S. Provisional Application No. 60/422,337, U.S. Pat. Nos. 6,353,017B1, 6,492,662B1, 6,353,017 B1 and 6,525,036B1, 6,229,011B1, 6,610,700, the disclosures of which are incorporated herein by reference in their entirety.

Hydrolysis of the ester group in compound 3 provides a compound of formula 4. The hydrolysis conditions depend on the nature of the protecting group. For example, when R is alkyl the hydrolysis is carried out under aqueous basic hydrolysis reaction conditions to give the corresponding acid of formula 4. The reaction is typically carried out with cesium carbonate, lithium hydroxide, and the like in an aqueous alcohol such as methanol, ethanol, and the like.

Compound 4 is then reacted with an α-hydroxyketoamide of formula 5 to give a compound of Formula 6. The reaction is typically carried out in the presence of a suitable coupling agent e.g., benzotriazole-1-yloxytrispyrrolidinophosphonium hexafluorophosphate (PyBOP®), O-benzotriazol-1-yl-N,N,N',N'-tetramethyl-uronium hexafluorophosphate (HBTU), O-(7-azabenzotriazol-1-yl)-1,1,3,3-tetramethyl-uronium hexafluorophosphate (HATU), 1-(3-dimethylaminopropyl)-3-ethylcarbodiimide hydrochloride (EDC), or 1,3-dicyclohexyl-carbodiimide (DCC), optionally in the presence of 1-hydroxy-benzotriazole (HOBT), and a base such as N,N-diisopropylethylamine, triethylamine, N-methylmorpholine, and the like. The reaction is typically carried out at 20 to 30° C., preferably at about 25° C., and requires 2 to 24 h to complete. Suitable reaction solvents are inert organic solvents such as halogenated organic solvents (e.g., methylene chloride, chloroform, and the like), acetonitrile, N,N-dimethylformamide, ethereal solvents such as tetrahydrofuran, dioxane, and the like.

Alternatively, the above coupling step can be carried out by first converting 4 into an active acid derivative such as succinimide ester and then reacting it with an α-hydroxyketoamide of formula 5. The reaction typically requires 2 to 3 h to complete. The conditions utilized in this reaction depend on the nature of the active acid derivative. For example, if it is an acid chloride derivative of 4, the reaction is carried out in the presence of a suitable base (e.g. triethylamine, diisopropylethylamine, pyridine, and the like). Suitable reaction solvents are polar organic solvents such as acetonitrile, N,N-dimethylformamide, dichloromethane, or any suitable mixtures thereof. Compounds of formula 5 can be prepared by methods well known in the art e.g., they can be prepared by the procedures described in PCT application publication No. WO 02/18369, the disclosure of which is incorporated herein by reference in its entirety.

Oxidation of the hydroxyl group in compound 6 with a suitable oxidizing agent such as OXONE® provides a compound of Formula (I).

Alternatively, compounds of Formula (I) where $R^1$, $R^2$, $R^3$, $R^4$, $R^5$, $R^6$ and $R^8$ are as defined in the Summary of the Invention and $R^7$ is hydrogen can be prepared by proceeding as in the following Reaction Scheme 2 below.

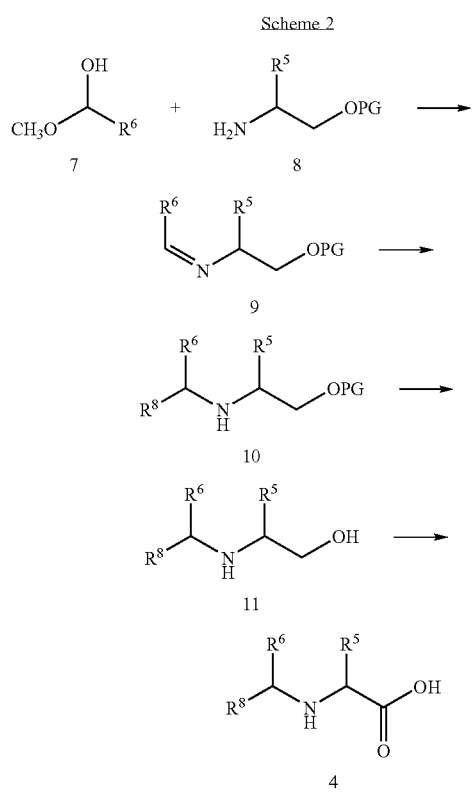

Reaction of a compound of formula 8 where $R^5$ is as defined in the Summary of the Invention and PG is a suitable oxygen protecting group with a hemiacetal of formula 7 where $R^6$ is as defined in the Summary of the Invention provides an imine compound of of formula 9. Treatment of 9 with an organolithium compound of formula $R^8Li$ where $R^8$ is not hydrogen provides compound 10. Removal of the oxygen protecting group, followed by oxidation of the resulting alcohol 11 provides a compound of formula 4 which is then converted to a compound of Formula (I) as described in Scheme 1 above. Suitable oxygen protecting groups and reaction conditions for putting them on and removing them can be found in Greene, T. W.; and Wuts, P. G. M.; *Protecting Groups in Organic Synthesis*; John Wiley & Sons, Inc. 1999.

Alternatively, compounds of Formula (I) where $R^1$, $R^2$, $R^3$, $R^4$, $R^5$, $R^6$ and $R^8$ are as defined in the Summary of the Invention and $R^7$ is hydrogen can be prepared by proceeding as in the following Reaction Scheme 3 below.

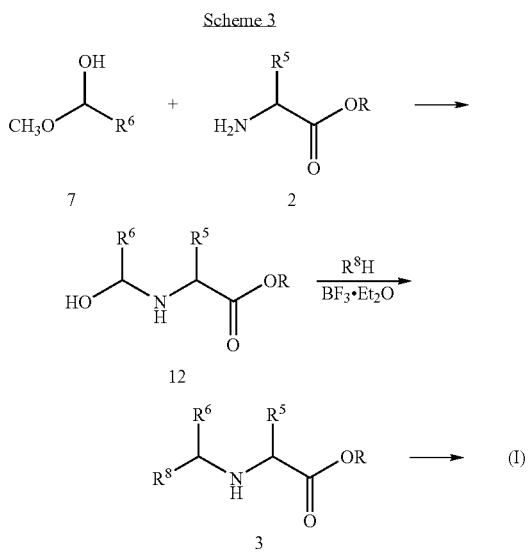

Reaction of an amino acid compound of formula 2 where R is alkyl and $R^5$ is as defined in the Summary of the Invention with a hemiacetal compound of formula 7 provides a 2-(1-hydroxy-2,2,2-trifluoroethylamino)acetate compound of formula 12. The reaction is carried out in the presence of a catalytic amount of an acid such as p-toluenesulfonic acid and in an aromatic hydrocarbon solvent such as toluene, benzene, and the like.

Treatment of 12 with a compound of formula $R^8H$ where $R^8$ is aryl or heteroaryl under Friedel-Crafts reaction conditions or trialkylaluminum in toluene provides a compound of formula 3 which is then converted to a compound of Formula (I) as described above.

Alternatively, compounds of Formula (I) where $R^1$, $R^2$, $R^3$, $R^4$, $R^5$, $R^6$ and $R^8$ are as defined in the Summary of the Invention and $R^7$ is hydrogen can be prepared by proceeding as in the following Reaction Scheme 4 below.

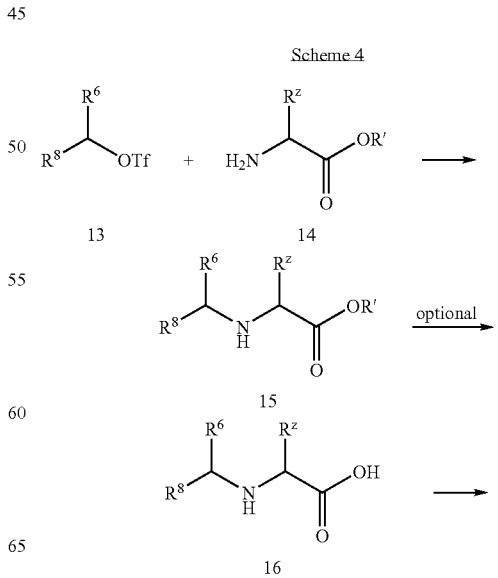

-continued

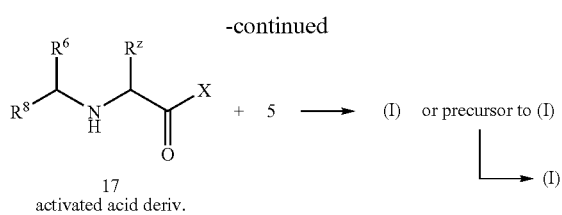

17
activated acid deriv.

Reaction of a compound of formula 13 where $R^6$ and $R^8$ is as defined in Summary of the Invention with a compound of formula 14 where R' is hydrogen or a carboxy protecting group and $R^z$ is $R^5$ or a precursor group (e.g., -alkylene-S-trityl, -alkylene-S-alkylene-heteroaryl, and the like) to $R^5$ group provides a compound of formula 15. The reaction is carried out in a suitable organic solvent, including but not limited to, diethyl ether, tetrahydrofuran, acetonitrile, benzene, toluene, xylene, and the like, or mixtures thereof and optionally in the presence of an organic or inorganic base. Preferably, the organic base is triethylamine, pyridine, N-methylmorpholine, collidine, diisopropylethylamine, and the like. Preferably, the inorganic base is cesium carbonate, sodium carbonate, sodium bicarbonate, and the like. The reaction is optionally carried out in the presence of a drying agent such as molecular sieves. Preferably, the reaction is carried out at room temperature.

Compounds of formula 13 can be prepared by methods well known in the art. For example, a compound of formula 13 where $R^8$ is phenyl or 4-fluorophenyl and $R^6$ is trifluoromethyl can be readily prepared from commercially available 2,2,2-trifluoroacetophenone or 2,2,2,4'-tetrafluoroacetophenone respectively, by reducing the keto group to an alcoholic group by suitable reducing agent such as sodium borohydride, lithium aluminum hydride, and the like. The solvent used depends on the type of reducing agent. For example, when sodium borohydride is used the reaction is carried out in an alcoholic organic solvent such as methanol, ethanol, and the like. When lithium aluminum hydride is used the reaction is carried out in an ethereal solvent such as tetrahydrofuran, and the like. Reaction of 2,2,2-trifluoro-1-phenylethanol or 2,2,2-trifluoro-1-(4-fluorophenyl)ethanol with triflic anhydride or trifluoromethanesulfonyl chloride provides the desired compound. Compounds of formula 13 where $R^7$ and $R^8$ are hydrogen and $R^6$ is 1,1,2,2,2-pentafluoroethyl can be prepared from commercially available 2,2,3,3,3-pentafluoropropan-1-ol can as described above. Optically enriched compound of formula 15 can be obtained by reduction of the corresponding halogenated acetophenone with a suitable reducing agent such as catecholborane or $BH_3$-DMS complex in the presence of a suitable catalyst such as (S) or (R)-methyl CBS oxazaborolidine catalyst or (S) or (R)-α,α-diphenyl-2-pyrrolidine-methanol in the presence of BBN to provide chiral alcohol which is then converted to compound 13 as described above. Compounds of formula 14 are either commercially available or they can be prepared by methods well known in the art.

Removal of the carboxy protecting group from a compound of formula 15 where R' is a protecting group provides a compound of formula 16. The conditions used to remove the carboxy protecting group depend on the nature of the carboxy protecting group. For example, if R' is alkyl, it is removed under basic hydrolysis reaction conditions utilizing aqueous base such as aqueous lithium hydroxide, sodium hydroxide, and the like in an alcoholic solvent such as methanol, ethanol, and the like. Additionally, if the $R^z$ group in compound 14 is a precursor group to $R^5$, it can be converted to $R^5$ prior or after the ester hydrolysis step.

Compound 15 (where R' is hydrogen) or 16 is then converted to an activated acid derivative 17 (X is a leaving group) and which upon reaction with an aminoacetonitrile compound of formula 5 provides a compound of Formula (I) when $R^z$ is $R^5$ or a precursor compound to (I) when $R^z$ is a precursor group to $R^5$. The activated acid derivative can be prepared and then reacted with compound 5 in a stepwise manner or the activated acid derivative can be generated in situ in the presence of compound 5. For example, if the activated acid is acid halide it is first prepared by reacting 16 with a halogenating agent such as thionyl chloride, oxalyl chloride and the like and then reacted with compound 5. Alternatively, the activated acid derivative is generated in situ by reacting compound 16 and 5 in the presence of a suitable coupling agent e.g., benzotriazole-1-yloxytrispyrrolidinophosphonium hexafluorophosphate (PyBOP®), O-benzotriazol-1-yl-N,N, N',N'-tetramethyl-uronium hexafluorophosphate (HBTU), O-(7-azabenzotriazol-1-yl)-1,1,3,3-tetramethyl-uronium hexafluorophosphate (HATU), 1-(3-dimethylaminopropyl)-3-ethylcarbodiimide hydrochloride (EDC), 1,3-dicyclohexyl-carbodiimide (DCC), an the like, optionally in the presence of 1-hydroxybenzotriazole (HOBT), and in the presence of a base such as N,N-diisopropylethylamine, triethylamine, N-methylmorpholine, and the like. Suitable reaction solvents are inert organic solvents such as halogenated organic solvents (e.g., methylene chloride, chloroform, and the like), acetonitrile, N,N-dimethylformamide, ethereal solvents such as tetrahydrofuran, dioxane, and the like. If $R^z$ is a precursor group to $R^5$, it is converted to $R^5$ group to provide a compound of Formula (I) e.g, conversion of -alkylene-S-alkylene-heteroaryl to -alkylene-$SO_2$-alkylene-heteroaryl under oxidation reaction conditions.

A compound of Formula (I) can be converted to other compounds of Formula (I). For example:

A compound of Formula (I) containing a hydroxy group may be prepared by de-alkylation/benzylation of an alkoxy/benzyloxy substituent; those containing an acid group, by hydrolysis of an ester group; and those containing a cyano, by displacement of a bromine atom on the corresponding compounds of Formula (1). A compound of Formula (I) containing a cyano group can be converted to a corresponding carboxy containing compound by hydrolysis of the cyano group. The carboxy group, in turn, can be converted to an ester group.

A compound of Formula (I) can be prepared as a pharmaceutically acceptable acid addition salt by reacting the free base form of the compound with a pharmaceutically acceptable inorganic or organic acid. Alternatively, a pharmaceutically acceptable base addition salt of a compound of Formula (I) can be prepared by reacting the free acid form of the compound with a pharmaceutically acceptable inorganic or organic base. Inorganic and organic acids and bases suitable for the preparation of the pharmaceutically acceptable salts of compounds of Formula (I) are set forth in the definitions section of this Application. Alternatively, the salt forms of the compounds of Formula (I) can be prepared using salts of the starting materials or intermediates.

The free acid or free base forms of the compounds of Formula (I) can be prepared from the corresponding base addition salt or acid addition salt form. For example, a compound of Formula (I) in an acid addition salt form can be converted to the corresponding free base by treating with a suitable base (e.g., ammonium hydroxide solution, sodium hydroxide, and the like). A compound of Formula (I) in a base addition salt form can be converted to the corresponding free acid by treating with a suitable acid (e.g., hydrochloric acid, etc).

The N-oxides of compounds of Formula (I) can be prepared by methods known to those of ordinary skill in the art. For example, N-oxides can be prepared by treating an unoxidized form of the compound of Formula (I) with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds of Formula (I) can be prepared from the N-oxide of an appropriate starting material.

Compounds of Formula (I) in unoxidized form can be prepared from N-oxides of compounds of Formula (I) by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g., acetonitrile, ethanol, aqueous dioxane, or the like) at 0 to 80° C.

Prodrug derivatives of the compounds of Formula (I) can be prepared by methods known to those of ordinary skill in the art (e.g., for further details see Saulnier et al. (1994), *Bioorganic and Medicinal Chemistry Letters*, Vol. 4, p. 1985). For example, appropriate prodrugs can be prepared by reacting a non-derivatized compound of Formula (I) with a suitable carbamylating agent (e.g., 1,1-acyloxyalkylcarbonochloridate, para-nitrophenyl carbonate, or the like).

Protected derivatives of the compounds of Formula (I) can be made by means known to those of ordinary skill in the art. A detailed description of the techniques applicable to the creation of protecting groups and their removal can be found in T. W. Greene, *Protecting Groups in Organic Synthesis, 3rd* edition, John Wiley & Sons, Inc. 1999.

Compounds of the present invention may be conveniently prepared or formed during the process of the invention, as solvates (e.g. hydrates). Hydrates of compounds of the present invention may be conveniently prepared by recrystallisation from an aqueous/organic solvent mixture, using organic solvents such as dioxin, tetrahydrofuran or methanol.

Compounds of Formula (I) can be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diasteromeric derivatives of compounds of Formula (I), dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, *Enantiomers, Racemates and Resolutions*, John Wiley & Sons, Inc. (1981).

Preparation of Biological Agents

In practicing this invention several processes for the generation or purification of biological agents are used. Methods for preparing the biologics are well known in the art as discussed below.

Monoclonal antibodies can be prepared using standard techniques well known in the art such as by the method of Kohler and Milstein, *Nature* 1975, 256:495, or a modification thereof, such as described by Buck et al. 1982, *In Vitro* 18:377. Typically, a mouse or rat is immunized with the MenB PS derivative conjugated to a protein carrier, boosted and the spleen (and optionally several large lymph nodes) removed and dissociated into single cells. If desired, the spleen cells may be screened (after removal of non-specifically adherent cells) by applying a cell suspension to a plate or well coated with the antigen. B-cells, expressing membrane-bound immunoglobulin specific for the antigen, will bind to the plate, and will not be rinsed away with the rest of the suspension. Resulting B-cells, or all dissociated spleen cells, are then induced to fuse with myeloma cells to form hybridomas. Representative murine myeloma lines for use in the hybridizations include those available from the American Type Culture Collection (ATCC).

Chimeric antibodies composed of human and non-human amino acid sequences may be formed from the mouse monoclonal antibody molecules to reduce their immunogenicity in humans (Winter et al. *Nature* 1991 349:293; Lobuglio et al. *Proc. Nat. Acad. Sci.* USA 1989 86:4220; Shaw et al. *J. Immunol.* 1987 138:4534; and Brown et al. *Cancer Res.* 1987 47:3577; Riechmann et al. *Nature* 1988 332:323; Verhoeyen et al. *Science* 1988 239:1534; and Jones et al. *Nature* 1986 321:522; EP Publication No.519, 596, published Dec. 23, 1992; and U.K. Patent Publication No. GB 2,276,169, published Sep. 21, 1994).

Antibody molecule fragments, e.g., F(ab')$_2$, FV, and sFv molecules, that are capable of exhibiting immunological binding properties of the parent monoclonal antibody molecule can be produced using known techniques. Inbar et al. *Proc. Nat. Acad. Sci.* USA 1972 69:2659; Hochman et al. *Biochem.* 1976 15:2706; Ehrlich et al. *Biochem.* 1980 19:4091; Huston et al. *Proc. Nat. Acad. Sci.* USA 1988 85(16):5879; and U.S. Pat. Nos. 5,091,513 and 5,132,405, and U.S. Pat. No. 4,946,778.

In the alternative, a phage-display system can be used to expand the monoclonal antibody molecule populations in vitro. Saiki, et al. *Nature* 1986 324:163; Scharf et al. *Science* 1986 233:1076; U.S. Pat. Nos. 4,683,195 and 4,683,202; Yang et al. *J. Mol. Biol.* 1995 254:392; Barbas, III et al. *Methods: Comp. Meth Enzymol.* 1995 8:94; Barbas, III et al. *Proc. Natl. Acad. Sci.* USA 1991 88:7978.

The coding sequences for the heavy and light chain portions of the Fab molecules selected from the phage display library can be isolated or synthesized, and cloned into any suitable vector or replicon for expression. Any suitable expression system can be used, including, for example, bacterial, yeast, insect, amphibian and mammalian systems. Expression systems in bacteria include those described in Chang et al. *Nature* 1978 275:615, Goeddel et al. *Nature* 1979 281:544, Goeddel et al. *Nucleic Acids Res.* 1980 8:4057, European Application No. EP 36,776, U.S. Pat. No. 4,551,433, deBoer et al. *Proc. Natl. Acad. Sci.* USA 1983 80:21-25, and Siebenlist et al. *Cell* 1980 20:269.

Expression systems in yeast include those described in Hinnen et al. *Proc. Natl. Acad. Sci.* USA 1978 75:1929, Ito et al. *J. Bacteriol.* 1983 153:163, Kurtz et al. *Mol. Cell. Biol.* 1986 6:142, Kunze et al. *J. Basic Microbiol.* 1985 25:141, Gleeson et al. *J. Gen. Microbiol.* 1986 132:3459, Roggenkamp et al. *Mol. Gen. Genet.* 1986 202:302, Das et al. *J. Bacteriol.* 1984 158:1165, De Louvencourt et al. *J. Bacteriol.* 1983 154:737, Van den Berg et al. *Bio/Technology* 1990 8:135, Kunze et al. *J. Basic Microbiol.* 1985 25:141, Cregg et al. *Mol. Cell. Biol.* 1985 5:3376, U.S. Pat. Nos. 4,837,148 and 4,929,555, Beach et al. *Nature* 1981 300:706, Davidow et al. *Curr. Genet.* 1985 10:380, Gaillardin et al. *Curr. Genet.* 1985 10:49, Ballance et al. *Biochem. Biophys. Res. Commun.* 1983 112:284-289, Tilburn et al. *Gene* 1983 26:205-221, Yelton et al. *Proc. Natl. Acad. Sci.* USA 1984 81:1470-1474, Kelly et al. *EMBO J.* 1985 4:475479; European Application No. EP 244,234, and International Publication No. WO 91/00357.

Expression of heterologous genes in insects can be accomplished as described in U.S. Pat. No. 4,745,051, European Application Nos. EP 127,839 and EP 155,476, Vlak et al. *J. Gen. Virol.* 1988 69:765-776, Miller et al. *Ann. Rev. Microbiol.* 1988 42:177, Carbonell et al. *Gene* 1988 73:409, Maeda et al. *Nature* 1985 315:592-594, Lebacq-Verheyden et al. *Mol. Cell. Biol.* 1988 8:3129, Smith et al. *Proc. Natl. Acad. Sci.* USA 1985 82:8404, Miyajima et al. *Gene* 1987 58:273, and Martin et al. *DNA* 1988 7:99. Numerous baculoviral strains and variants and corresponding permissive insect host cells from hosts are described in Luckow et al. *Bio/Technology* 1988 6:47-55, Miller et al. *GENETIC ENGINEERING*, Setlow, J. K. et al. eds., Vol. 8, Plenum Publishing, pp. 1986 277-279, and Maeda et al. *Nature* 1985 315:592-594.

Mammalian expression can be accomplished as described in Dijkema et al. *EMBO J.* 1985 4:761, Gorman et al. *Proc. Natl. Acad. Sci.* USA 1982 79:6777, Boshart et al. *Cell* 1985 41:521, and U.S. Pat. No. 4,399,216. Other features of mammalian expression can be facilitated as described in Ham et al. *Meth. Enz.* 1979 58:44, Barnes et al. *Anal. Biochem.* 1980 102:255, U.S. Pat. Nos. 4,767,704, 4,657,866, 4,927,762, 4,560,655 and Reissued U.S. Pat. No. RE 30,985, and in International Publication Nos. WO 90/103430, WO 87/00195.

The production of recombinant adenoviral vectors are described in U.S. Pat. No. 6,485,958.

Botulinum toxin type A can be obtained by establishing and growing cultures of *Clostridium botulinum* in a fermenter and then harvesting and purifying the fermented mixture in accordance with known procedures.

Any of the above-described protein production methods can be used to provide the biologic that would benefit from the present invention.

Pharmacology and Utility

The compounds of the invention are selective inhibitors of cysteine proteases such as cathepsin S, K, B, and/or F, and in particular cathepsin S, and accordingly are useful for treating diseases in which cysteine protease activity contributes to the pathology and/or symptomatology of the disease. For example, the compounds of the invention are useful in treating autoimmune disorders, including, but not limited to, juvenile onset diabetes, psoriasis, multiple sclerosis, pemphigus vulgaris, Graves' disease, myasthenia gravis, systemic lupus erythemotasus, rheumatoid arthritis and Hashimoto's thyroiditis, allergic disorders, including, but not limited to, asthma, allogeneic immune responses, including, but not limited to, organ transplants or tissue grafts and endometriosis.

Cathepsin S is also implicated in disorders involving excessive elastolysis, such as chronic obstructive pulmonary disease (e.g., emphysema), bronchiolitis, excessive airway elastolysis in asthma and bronchitis, pneumonities and cardiovascular disease such as plaque rupture and atheroma. Cathepsin S is implicated in fibril formation and, therefore, inhibitors of cathepsins S are of use in treatment of systemic amyloidosis.

The cysteine protease inhibitory activities of the compounds of Formula (I) can be determined by methods known to those of ordinary skill in the art. Suitable in vitro assays for measuring protease activity and the inhibition thereof by test compounds are known. Typically, the assay measures protease-induced hydrolysis of a peptide-based substrate. Details of assays for measuring protease inhibitory activity are set forth in Biological Examples 1-5, infra.

Administration and Pharmaceutical Compositions

In general, compounds of Formula (I) will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. For example, therapeutically effective amounts of a compound of Formula (I) may range from about 10 micrograms per kilogram body weight (μg/kg) per day to about 100 milligram per kilogram body weight (mg/kg) per day, typically from about 100 μg/kg/day to about 10 mg/kg/day. Therefore, a therapeutically effective amount for an 80 kg human patient may range from about 1 mg/day to about 8 g/day, typically from about 1 mg/day to about 800 mg/day. In general, one of ordinary skill in the art, acting in reliance upon personal knowledge and the disclosure of this Application, will be able to ascertain a therapeutically effective amount of a compound of Formula (I) for treating a given disease.

The compounds of Formula (I) can be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of Formula (I) in combination with at least one pharmaceutically acceptable excipient. Acceptable excipients are non-toxic, aid administration, and do not adversely affect the therapeutic benefit of the active ingredient. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, and the like). Preferred liquid carriers, particularly for injectable solutions, include water, saline, aqueous dextrose and glycols.

The amount of a compound of Formula (I) in the composition may vary widely depending upon the type of formulation, size of a unit dosage, kind of excipients and other factors known to those of skill in the art of pharmaceutical sciences. In general, a composition of a compound of Formula (I) for treating a given disease will comprise from 0.01% w to 90% w, preferably 5% w to 50% w, of active ingredient with the remainder being the excipient or excipients. Preferably the pharmaceutical composition is administered in a single unit dosage form for continuous treatment or in a single unit dosage form ad libitum when relief of symptoms is specifically required. Representative pharmaceutical formulations containing a compound of Formula (I) are described below.

EXAMPLES

The present invention is further exemplified, but not limited by, the following examples that illustrate the preparation of compounds of Formula (I) (Examples) and intermediates (References) according to the invention.

Reference A

Synthesis of trifluoromethanesulfonic acid 2,2,2-trifluoro-1-(4-fluorophenyl)ethyl ester

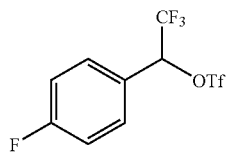

Step 1

To a stirred solution of 2,2,2,4'-tetrafluoroacetophenone (10 g, 52.1 mmol) in methanol (50 mL) was added NaBH$_4$ (0.98 g, 26.5 mmol) at 0° C. After stirring at 25° C. for 2 h, the reaction mixture was quenched by adding 1N HCl (100 mL) and then extracted with ethyl ether. The ether extract was washed with brine, dried with MgSO$_4$, and concentrated to give 2,2,2-trifluoro-1-(4-fluorophenyl)ethanol (11.32 g) which was used in next step without further purification.

Step 2

NaH (640 mg, 16 mmol, 60% in mineral oil) was washed twice with hexane (20 mL) and then suspended in dried diethyl ether (20 mL). A solution of 2,2,2-trifluoro-1-(4-fluoro-phenyl)ethanol (1.94 g, 10 mmol) in diethyl ether (10 mL) was added at 0° C. After stirring for 2 h at room temperature, a solution of trifluoromethanesulfonyl chloride (1.68 g, 10 mmol) in diethyl ether (10 mL) was added. After 2 h, the reaction mixture was quenched by adding a solution of NaHCO$_3$ and the product was extracted with diethyl ether. The extracts were washed with brine and dried, and the solvent was removed to yield trifluoromethanesulfonic acid 2,2,2-trifluoro-1-(4-fluorophenyl)ethyl ester (3.3 g).

Reference B

Synthesis of 2,2,2-trifluoro-1(R)-(4-fluorophenyl)ethanol

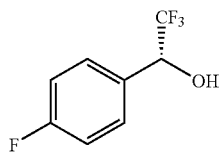

To a −78° C. toluene (25 mL)/dichloromethane (25 mL) solution of 2,2,2,4'-tetrafluoroacetophenone (2.5 g, 13.01 mmol) and 1M S-methyl CBS oxazaborolidine catalyst (1.3 mL, 1.3 mmol) was added freshly distilled catecholborane (1.66 mL, 15.62 mmol). The reaction mixture was maintained at −78° C. for 16 h at which time 4N HCl (5 mL in dioxane) was added and the reaction mixture was allowed to warm to room temperature. The reaction mixture was diluted with ethyl acetate and washed with a saturated brine solution. The organic layer was dried over magnesium sulfate, filtered and concentrated to provide a solid. The solid was suspended in hexanes and filtered off. The hexanes filtrate containing the desired product was concentrated and the residue subjected to flash chromatography (10 hexanes: 1 ethylacetate) to provide the title compound as colorless oil (2.2 g, 87% yield). The ratio of enantiomers was determined to be 95:5 by chiral HPLC (Chiralcel OD column, 95 hexanes: 5 isopropanol mobile phase. Ret. time major product 6.757 min. Ret. time minor isomer 8.274 min.).

Reference D

Synthesis of 2(R)-[2,2,2-trifluoro-1(S)-(4-fluorophenyl)ethylamino]-3-tritylsulfanylpropionic acid

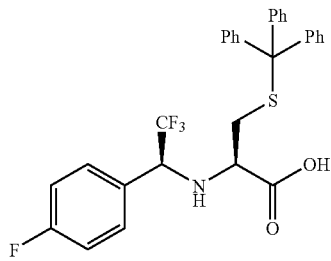

To a slurry of S-trityl-L-cysteine (4.86 g, 13.37 mmol) in dichloromethane (97 mL, 20 mL/g AA) at room temperature was added diisopropylethylamine (9.32 mL, 53.48 mmol) followed by a solution of trifluoromethanesulfonic acid 2,2,2-trifluoro-1(RS)-phenylethyl ester (5.32 g, 16.04 mmol) (major enantiomer (S), 90 ee) in dichloromethane (15 mL) via syringe all at once. After 19 h, the reaction mixture was concentrated on the rotovap to give an oil. Diethyl ether was added and the solution was washed with 1N HCl and brine. The organic layer was dried over MgSO$_4$, filtered, and concentrated. Flash chromatography of the residue with 2 hexanes/1 ethyl acetate/0.25% acetic acid as the eluent provided 2(R)-[2,2,2-trifluoro-1(RS)-(4-fluorophenyl)ethylamino]-3-tritylsulfanyl-propionic acid (6 g) (major diastereomer (R,S), 90 de) as an oil/foam.

Reference E

Synthesis of 2-(1-aminocyclopropyl)-N-cyclopropyl-2-hydroxyacetamide

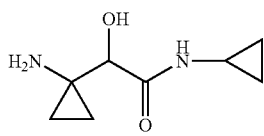

Step 1

1-Aminocyclopropanecarbonitrile chlorohydrate (6.1 g, 51.4 mmol) was refluxed in 6N hydrochloric acid (500 mL) for 7 h and then concentrated to yield 1-aminocyclopropane-carboxylic acid chlorohydrate as an off-white solid which was used in the next step without further purification.

Step 2

A solution of 1-aminocyclopropanecarboxylic acid chlorohydrate (3.6 g, 26.2 mmol) in MeOH (100 mL), containing potassium carbonate (4.0 g, 28.94 mmol) was stirred at room temperature for 48 h. After filtration, MeOH was removed under reduced pressure to yield 1-aminocyclopropanecar-boxylic acid (2.64 g) which was used in the next step without further purification.

Step 3

1-Aminocyclopropanecarboxylic acid (2.64 g, 26.1 mmol) and tetramethylammonium hydroxide (2.38 g, 26.1 mmol) was added to acetonitrile (150 mL). The reaction mixture became homogeneous after stirring at room temperature for about an hour. Boc$_2$O (8.54 g, 39.2 mmol) was then added and stirring was continued for 2 days. On the 3rd day, another portion of Boc$_2$O (2.85 g, 13.1 mmol) was added and the reaction mixture stirred an additional day. Acetonitrile was removed under reduced pressure and the residue was partitioned between H$_2$O and Et$_2$O. The aqueous layer was washed with Et$_2$O and then acidified with solid citric acid to pH ~3. The aqueous solution was extracted with EtOAc. The combined EtOAc extracts were washed with brine, dried (Na$_2$SO$_4$), and the EtOAc was removed under reduced pressure to give 1-tert-butoxycarbonylaminocyclopro-panecarboxylic acid as a white solid (2.32 g) which was used in the next step without further purification.

Step 4

To a solution of 1-tert-butoxycarbonylaminocyclopro-panecarboxylic acid (2.32 g, 11.5 mmol) in CH$_2$Cl$_2$ (25 mL) at 0° C. was added N,O-dimethylhydroxylamine hydrochloride (1.24 g, 12.7 mmol), triethylamine (2.57 g, 3.54 mL, 25.4 mmol), and HATU (4.82 g, 12.7 mmol). The reaction mixture was stirred at room temperature for 4 h. The reaction mixture was concentrated under reduced pressure and then partitioned between Et$_2$O and water. The water layer was extracted with Et$_2$O. The combined organic layer was washed with brine, dried (Na$_2$SO$_4$), and concentrated under reduced pressure to yield [1-(methoxy-methyl-carbamoyl)-cyclopropyl]car-bamic acid tert-butyl ester which was used in the next step without further purification.

Step 5

To a 0.05 M solution of [1-(methoxy-methyl-carbamoyl) cyclopropyl]carbamic acid tert-butyl ester in Et$_2$O (80 mL, 4.0 mmol) at room temperature was added dropwise lithium aluminum hydride (1.0 M in Et$_2$O, 5 mL, 5.0 mmol). The reaction mixture was stirred for another 20 min and then quenched with 6 mL of a solution of KHSO$_4$ in water. The layers were separated and the aqueous layer was extracted with Et$_2$O. The combined organic layers were washed with 1 N HCl, saturated NaHCO$_3$, and brine, dried (Na$_2$SO$_4$), and concentrated to yield (1-formylcyclopropyl)carbamic acid tert-butyl ester as a colorless oil (393 mg) which was used immediately in the next step without further purification.

Step 6

To a solution of (1-formylcyclopropyl)carbamic acid tert-butyl ester (393 mg, 2.12 mmol) in CH$_2$Cl$_2$ (4 mL) was added acetic acid (191 mg, 0.182 mL, 3.18 mmol), and cyclopropyl isocyanide (142 mg, 2.12 mmol). The reaction mixture was stirred overnight at room temperature and then concentrated under reduced pressure to yield crude acetic acid (1-tert-butoxycarbonylaminocyclopropyl)cyclopropylcarbamoyl methyl ester which was used in the next step without further purification.

Step 7

To a solution of the acetic acid (1-tert-butoxycarbonylami-nocyclopropyl)-cyclopropylcarbamoyl methyl ester in MeOH (5 mL) was added 10% NaOH (1 mL). The reaction mixture was stirred at room temperature for 2 h and then acidified with 2.5N HCl to pH 7. The solution was extracted with EtOAc, washed with brine, dried (Na$_2$SO$_4$), and concentrated under reduced pressure to yield [1-(cyclopropylcar-bamoylhydroxymethyl)cyclopropyl]-carbamic acid tert-butyl ester as a yellow oil which was used in the next step without further purification.

Step 8

A solution of [1-(cyclopropylcarbamoylhydroxymethyl) cyclopropyl]carbamic acid tert-butyl ester in CH$_2$Cl$_2$ (5 mL) and TFA (5 mL) was stirred at room temperature for 2.5 h. The reaction mixture was concentrated and chased with toluene to yield 2-(1-aminocyclopropyl)-N-cyclopropyl-2-hydroxyacetamide.

Proceeding as described in Steps 3-8 above but substituting 1-aminocyclopropane-carboxylic acid with 1-aminocyclo-hexanecarboxylic acid provided 2-(1-aminocyclohexyl)-N-cyclopropyl-2-hydroxyacetamide.

Reference F

Synthesis of 3-amino-N-cyclopropyl-2-hydroxy-3-methylbutyramide

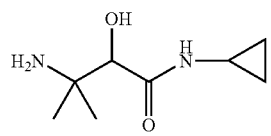

Step 1

To a solution of (2-hydroxy-1,1-dimethylethyl)-carbamic acid tert-butyl ester (284 mg, 1.5 mmol) in CH$_2$Cl$_2$ (5 mL) was added at 0° C. Dess-Martin periodane (763 mg, 1.8 mmol). After 1.5 h, a solution of 0.26M Na$_2$S$_2$O$_3$ in saturated NaHCO$_3$ (6 mL) was added and the resulting mixture was stirred for 15 min. The layers were separated and the aqueous layer was extracted with CH₂Cl₂. The combined organic layers were dried (Na₂SO₄) and concentrated to yield (1,1-dimethyl-2-oxo-ethyl)carbamic acid tert-butyl ester as a white solid which was used in the next step without further purification.

Step 2

To a solution of (1,1-dimethyl-2-oxo-ethyl)-carbamic acid tert-butyl ester in CH₂Cl₂ was added acetic acid (180 mg, 0.172 mL, 3.0 mmol) and cyclopropyl isocyanide (101 mg, 1.5 mmol). The reaction mixture was stirred overnight at room temperature and then concentrated to yield crude acetic acid 2-tert-butoxycarbonylamino-1-cyclopropylcarbamoyl-2-methylpropyl ester which was used in the next step without further purification.

Step 3

To a solution of acetic acid 2-tert-butoxycarbonylamino-1-cyclopropylcarbamoyl-2-methylpropyl ester in MeOH (10 mL) was added 10% NaOH (1.5 mL). The reaction mixture was stirred at room temperature for 3 h and then acidified with 1N Hydrochloric acid to pH 7. The reaction mixture was extracted with EtOAc. The organic layer was dried (Na₂SO₄) concentrated to yield (2-cyclopropylcarbamoyl-2-hydroxy-1,1-dimethylethyl)-carbamic acid tert-butyl ester which was used in the next step without further purification.

Step 4

A solution of (2-cyclopropylcarbamoyl-2-hydroxy-1,1-dimethylethyl)-carbamic acid tert-butyl ester in CH₂Cl₂ (10 mL) and TFA (5 mL) was stirred at room temperature for 4 h. The reaction mixture was then concentrated and chased with toluene to yield 3-amino-N-cyclopropyl-2-hydroxy-3-methylbutyramide.

Reference G

Synthesis of
3-amino-N-benzyl-2-hydroxy-3-methylbutyramide

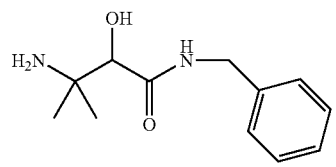

3-Amino-N-benzyl-2-hydroxy-3-methylbutyramide was made by the procedure described for 3-amino-N-cyclopropyl-2-hydroxy-3-methylbutyramide by substituting cyclopropyl isocyanide with benzyl isocyanide.

Example 1

Synthesis of 2-oxo-3(S)-{3-(pyridin-3-ylmethanesulfonyl)-2(R)-[2,2,2-trifluoro-1(S)-(4-fluorophenyl) ethylamino]-propionylamino}hexanoic acid cyclopropylamide

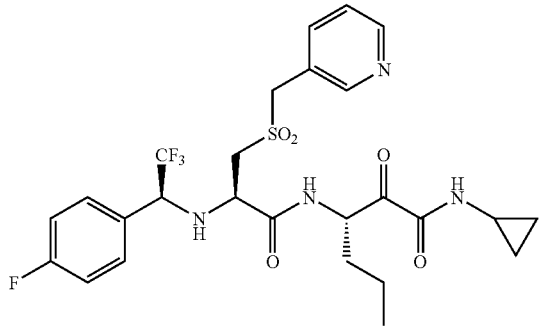

Step 1

Catecholborane (19.4 mL, 182 mmol) in dichloromethane (15 mL) was added to a dichloromethane solution of S-methyl CBS oxazaborolidine (13 mL, 13 mmol) and 2,2,2,4'-tetrafluoroacetopheone (18.2 mL, 130.13 mmol) dropwise at −78° C. in 30 min. The reaction mixture was stirred at −78° C. overnight. The reaction mixture was quenched with 4N HCl (13 mL) in dioxane at −78° C., warmed up to room temperature and the solvent was removed under reduced pressure. 10% NaHSO₃ solution (200 mL) was added to concentrate and the aqueous layer was extracted by hexane. The organic layer was washed by water and dried with MgSO₄. Solvent was removed under the reduced pressure to give 2,2,2-trifluoro-1(R)-(4-fluorophenyl)-ethanol (20 g) as colorless oil (90% e.e.).

Step 2

NaH (11.87 g, 296.7 mmol) was added to Et₂O (700 mL) at 0° C. under N₂ followed by addition of an Et₂O solution of 2,2,2-trifluoro-1(R)-(4-fluorophenyl)ethanol (44.3g, 228.2 mmol). The reaction mixture was stirred for 10 min at 0° C. then 1 h at room temperature. Trifluoromethanesulfonyl chloride (50 g, 296.7 mmol) in Et₂O was added at 0° C. under N₂ and the reaction mixture was stirred 10 min at 0° C. then 3 h at room temperature. The solvent was removed under the reduced pressure and H₂O (100 mL) was added slowly. The aqueous layer was extracted by hexane and the combined organic layer was dried over MgSO₄. The solvent was removed under the reduced pressure to give trifluoromethanesulfonic acid 2,2,2-trifluoro-1(R)-(4-fluorophenyl)ethyl ester (70 g) as colorless oil.

Step 3

2(R)-Amino-3-tritylsulfanylpropionic acid (78 g, 214.6mmol) was dissolved in CH₂Cl₂ and DIPEA (112 mL, 643.8 mmol) was added and the reaction mixture was stirred for 10 min at room temperature. Trifluoromethanesulfonic acid 2,2,2-trifluoro-1(R)-(4-fluorophenyl)ethyl ester (70 g, 214.6 mmol) in CH₂Cl₂ was added and the reaction mixture was stirred overnight at room temperature. Solvent was removed under the reduced pressure and the residue was dissolved in Et₂O and washed with 1N HCl, brine and dried over MgSO₄. Solvent was removed give 2(R)-[2,2,2-trifluoro-1(S)-(4-fluorophenyl)ethylamino]-3-tritylsulfanylpropionic acid (90 g) as a yellow solid.

Step 4

2(R)-[2,2,2-trifluoro-1(S)-(4-fluorophenyl)ethylamino]-3-tritylsulfanylpropionic acid 5.4 g, 10 mmol) was dissolved in CH₂Cl₂ and TFA (3.1 mL, 40 mmol) was added at 0° C. under N₂. Et₃SiH (3.2 mL, 20 mmol) was added at 0° C. under N₂ and the reaction mixture was warmed up to room temperature. After stirring for 2 h, the solvent was removed under the reduced pressure and the residue was dissolved in 1N NaOH (120 mL). The aqueous layer was extracted with hexane. To the aqueous solution dioxane (120 mL), 3-picolyl chloride hydrochloride (1.97 g, 12 mmol), and tris(2-carboxyethyl) phosphine hydrochloride (280 mg, 1 mmol) were added. The reaction mixture was stirred at room temperature overnight. Dioxane was removed under the reduced pressure. The aqueous solution was adjusted to pH 3 and was extracted with ethyl acetate. The combined organic extracts were dried over $MgSO_4$, filtered and concentrated under the reduced pressure to give 3-(pyridin-3-ylmethanesulfanyl)-2(R)-[2,2,2-trifluoro-1(S)-(4-fluorophenyl)-ethylamino]propionic acid which was used in the next step without further purification.

Step 5

To a solution of 3-(pyridin-3-ylmethanesulfanyl)-2(R)-[2,2,2-trifluoro-1(S)-(4-fluorophenyl)-ethylamino]propionic acid in methanol (10 mL), an aqueous solution of OXONE® (4.68 g, 15 mmol in 10 mL $H_2O$) was added. The reaction mixture was stirred at room temperature. After 2 h, solvent was removed under reduced pressure. The aqueous layer was extracted with ethyl acetate and the combined organic extracts were was washed with brine and dried with $MgSO_4$ and filtered The filtrate was concentrated under the reduced pressure to give 3-(pyridin-3-ylmethanesulfonyl)-2-(R)[2,2,2-trifluoro-1(S)-(4-fluorophenyl)ethylamino]propionic acid which was used in the next step without further purification.

Step 6

A mixture of 3-(pyridin-3-ylmethanesulfonyl)-2-(R)[2,2,2-trifluoro-1(s)-(4-fluorophenyl)ethylamino]propionic acid (420 mg, 1 mmol), 3(S)-amino-2-hydroxyhexanoic acid cyclopropylamide (186 mg, 1 mmol) prepared as described in PCT application publication No. WO-02/18369 as compound xiii, HBTU (455 mg, 1.2 mmol), and NMM (0.44 mL, 4 mmol) in acctonitrile was stirred at room temperature overnight. Sat. $NH_4Cl$ (10 mL) and ethyl acetate (10 mL) were added and after 20 min the aqueous layer was extracted with ethyl acetate. The combined organic extracts were washed with brine and dried with $MgSO_4$, filtered and the filtrated was concentrated under the reduced pressure to give 2-hydroxy-3(S)-{3-(pyridin-3-ylmethanesulfonyl)-2(R)-[2,2,2-trifluoro-1(S)-(4-fluorophenyl)-ethylamino]propionylamino}-hexanoic acid cyclopropylamide which was used in the next step without further purification.

Step 7

To a solution of 2-hydroxy-3(S)-{3-(pyridin-3-ylmethanesulfonyl)-2(R)-[2,2,2-trifluoro-1(S)-(4-fluorophenyl)ethylamino]propionylamino}hexanoic acid cyclopropylamide (590 mg, 1 mmol) in methylene chloride, DMP was added slowly. The reaction mixture was stirred at room temperature for 30 min and then a 0.26 M $Na_2S_2O_3$ in sat. $NaHCO_3$ was added. The reaction mixture was stirred for 20 min. The aqueous layer was extracted with methylene chloride and the combined organic extracts were dried over $MgSO_4$, filtered and concentrated to give 2-oxo-3(S)-{3-(pyridin-3-ylmethanesulfonyl)-2(R)-[2,2,2-trifluoro-1(s)-(4-fluorophenyl)ethylamino]-propionylamino}hexanoic acid cyclopropylamide which was purified by flash column (2% MeOH—$CH_2Cl_2$) to give pure product as a yellow solid.

$^1$H-NMR(DMSO-$d_6$): δ 0.80(m, 12H), 2.02(m, 1H), 3.3-3.7(b, 3H), 4.00(m, 1H), 4.46(m, 1H), 4.79(m, 2H), 7.25(m, 2H), 7.50(m, 2H), 7.65(b, 1H), 7.72(d, 1H), 8.01(d, 1H), 8.71(m, 3H). LC-MS: 587(M+1), 585, (M−1), 609(M+23).

Proceeding as described above but substituting 3-picolyl chloride with cyclopropylmethyl bromide provided 2-oxo-3 (S)-{3-(cyclopropylmethanesulfonyl)-2(R)-[2,2,2-trifluoro-1(S)-(4-fluorophenyl)ethylamino]-propionylamino}hexanoic acid cyclopropylamide (compound 1). $^1$H-NMR(DMSO-$d_6$): δ 0.32-0.41 (m, 2H), 0.53-0.67 (m, 6H), 0.81(t, J=7.2 Hz, 3H), 1.06-1.38 (m, 4H), 1.52-1.61 (m, 1H), 2.69-2.76 (m, 1H), 2.98 (dd, J=2.8 Hz, J=14.8 Hz, 1H), 3.19 (dd, J=8 Hz, J=14 Hz, 1H), 3.28-3.50 (m, 3H), 3.82-3.88 (m, 1H), 4.37 (quint, J=7.6 Hz, 1H), 4.70-4.76 (m, 1H), 7.22 (t, J=8.4 Hz, 2H), 7.43 (dd, J=5.6 Hz, J=8.4 Hz, 2H), 8.51 (d, J=7.2 Hz, 1H), 8.73 (d, J=5.2 Hz, 1H). LC-MS: 550(M+1), 548, (M−1).

Example 2

Synthesis of 2-oxo-3(S)-3-[2(R)-(2,2,3,3,3-pentafluoropropylamino)-3-(pyridyl-3-ylmethanesulfonyl)propionylamino]pentanoic acid cyclopropylamide

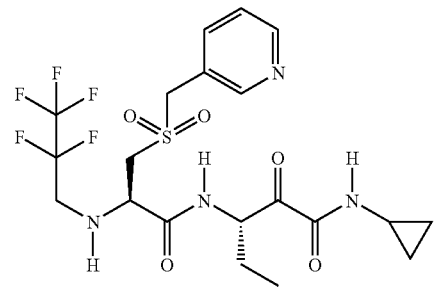

Step 1

To a −78° C. methylene chloride solution (75 mL) of 2,2,3,3,3-pentafluoropropan-1-ol (1.5 g, 10.0 mmol) and DIPEA (6.1 mL, 35.0 mmol) was added triflic anhydride (1.78 mL, 10.5 mmol). After 2.5 h, S-tritylcysteine was added all at once and the reaction mixture was stirred at 0° C. for 80 min. The reaction mixture was stirred at RT for 18 h and then concentrated on the rotovap. Ethyl acetate was added and the reaction mixture was washed with 1N HCl. The organic layer was dried over magnesium sulfate, filtered and concentrated. The crude product was purified by flash chromatography (3 hexanes/1 ethyl acetate+1% acetic acid) to provide 2(R)-(2,2,3,3,3-pentafluoropropylamino)-3-tritylsulfanylpropionic acid (3.29 g).

Step 2

To a methylene chloride solution (15 mL) of 2(R)-(2,2,3,3,3-pentafluoropropylamino)-3-tritylsulfanylpropionic acid (1.05 g, 2.12 mmol) was added TFA (0.653 mL, 8.48 mmol) followed by triethylsilane (0.677 mL, 4.24 mmol). The reaction mixture was stirred for 1.5 h at room temperature and then concentrated on the rotovap. To the residue was added 2N NaOH solution (20 mL) and the reaction mixture was extracted with hexanes. To the NaOH layer was added tris(2-carboxytriethyl)phosphine hydrochloride (60 mg) followed by 3-picolylchloride hydrochloride (348 mg, 2.12 mmol). After 1.5 h, the reaction mixture was acidified with conc. HCl to ~pH=4 and extracted with ethyl acetate. The organic layer was dried and concentrated to give 2(R)-(2,2,3,3,3-pentafluoropropylamino)-3-(pyridin-3-ylmethanesufanyl)propionic acid (530 mg).

Step 3

To a methylene chloride solution of 2(R)-(2,2,3,3,3-pentafluoropropylamino)-3-(pyridin-3-ylmethanesufanyl)propionic acid (151 mg, 0.44 mmol), 3(S)-amino-2-hydroxypentanoic acid cyclopropylamide hydrochloride (92 mg, 0.44 mmol), EDC (102 mg, 0.66 mmol), and HOBt hydrate (71 mg, 0.53 mmol) was added N-methylmorpholine (0.194 mL, 1.76 mmol). The reaction mixture was stirred for 2 h and then diluted with ethyl acetate and washed with sodium bicarbonate solution. Concentration of the organic layer gave 2-hydroxy-3(S)-[2(R)-(2,2,3,3,3-pentafluoropropylamino)-3-(pyridin-3-ylmethanesulfanyl)propionylamino]pentanoic acid cyclopropylamide (170 mg).

Step 4

To an NMP solution of 2-hydroxy-3(S)-[2(R)-(2,2,3,3,3-pentafluoropropylamino)-3-(pyridin-3-ylmethanesulfanyl)propionylamino]pentanoic acid cyclopropylamide (170 mg, 0.34 mmol) was added an aqueous solution of OXONE® (209 mg, 0.34 mmol). After 2 h, more OXONE® (105 mg, 0.17 mmol) was added with additional water plus some methanol. After an additional 1 h 40 min, the reaction mixture was diluted with ethyl acetate and washed with water. Concentration of the organic layer provided 2-hydroxy-3(S)-[2(R)-(2,2,3,3,3-pentafluoropropylamino)-3-(pyridin-3-ylmethylsulfonyl)propionylamino]pentanoic acid cyclopropylamide (176 mg).

Step 5

To a heterogeneous mixture of 2-hydroxy-3(S)-[2(R)-(2,2,3,3,3-pentafluoropropylamino)-3-(pyridin-3-ylmethanesulfonyl)propionylamino]pentanoic acid cyclopropylamide (176 mg, 0.33 mmol) in methylene chloride was added Dess-Martin periodinane (183 mg, 0.43 mmol). The reaction mixture became more heterogeneous after a couple of minutes. After 3 h, acetonitrile (3 mL) was added followed by NMP (6 mL) to give a homogeneous reaction. Additional Dess-Martin periodinane was added at this time (100 mg). After an additional 70 min of stirring, the reaction mixture was diluted with ethyl acetate and washed with sodium bicarbonate solution. The organic layer was separated and concentrated. Flash chromatography (95% methylene chloride/5% methanol) of the residue provided a solid which was suspended in a 1:1 IPA/ethanol mixture and allowed to evaporate to dyness to provide 2-oxo-3(S)-3-[2(R)-(2,2,3,3,3-pentafluoropropylamino)-3-(pyridyl-3-ylmethanesulfanyl)propionylamino]pentanoic acid cyclopropylamide (87 mg).

Example 3

Synthesis of N-(1-cyclopropylaminooxalylcyclopropyl)-3-cyclopropylmethanesulfonyl-2(R)-[2,2,2-trifluoro-1(S)-(4-fluorophenyl)ethylamino]propionamide To a solution of 3-cyclopropylmethanesulfanyl-2(R)-[2,2,2-trifluoro-1(s)-(4-fluorophenyl)ethylamino]-propionic acid (148 mg, 0.42 mmol), prepared as described in example 1 above, by substituting picolyl chloride with cyclopropylmethyl bromide, and 2-(1-amino-cyclopropyl)-N-cyclopropyl-2-hydroxyacetamide (108 mg, 0.63 mmol) in N-methylpyrrolidine (6 mL) at 0° C. was added N,N-diethylpropylamine (272 mg, 0.37 mL, 2.11 mmol), and HATU. The reaction mixture was stirred 4 hours at room temperature. The reaction mixture was diluted with EtOAc and washed with H$_2$O. The organic layer was dried (Na$_2$SO$_4$) and concentrated to yield N-[1-(cyclopropylcarbamoyl-hydroxy-methyl)cyclopropyl]-3-cyclopropylmethylsulfanyl-2-[2,2,2-trifluoro-1-(4-fluorophenyl)-ethylamino]propionamide which was converted to the title compound as described in Example 2, steps 4 and 5 above. MS (534.2 M+1, 532.1 M−1).

Follwing the procedure described in Example 3 above but substituting 2-(1-amino-cyclopropyl)-N-cyclopropyl-2-hydroxyacetamide with 3-amino-N-benzyl-2-hydroxy-3-methylbutyramide provided N-benzyl-3-{3-cyclopropylmethanesulfonyl-2(R)-[2,2,2-trifluoro-1(S)-(4-fluorophenyl)ethylamino]propionylamino}-3-methyl-2-oxo-butyramide. MS (586.3 M+1, 584.3 M−1).

Follwing the procedure described in Example 3 above but substituting 2-(1-amino-cyclopropyl)-N-cyclopropyl-2-hydroxyacetamide with 3-amino-N-benzyl-2-hydroxy-3-methylbutyramide and 2(R)-[2,2,2-trifluoro-1(S)-(4-fluorophenyl)ethylamino]-3-tritylsulfanylpropionic acid with 2(R)-[2,2,2-trifluoro-1(R)-(4-fluorophenyl)ethylamino]-3-tritylsulfanylpropionic acid provided N-benzyl-3-{3-cyclopropylmethanesulfonyl-2(R)-[2,2,2-trifluoro-1(R)-(4-fluorophenyl)ethylamino]propionylamino}-3-methyl-2-oxo-butyramide. N-Benzyl-3-{3-cyclopropylmethanesulfonyl-2-[2,2,2-trifluoro-1-(4-fluorophenyl)-ethylamino]-propionylamino}-3-methyl-2-oxo-butyramide MS (586.1 M+1, 584.1 M−1).

Follwing the procedure described in Example 3 above but substituting 2-(1-amino-cyclopropyl)-N-cyclopropyl-2-hydroxyacetamide with 3-amino-N-cyclopropyl-2-hydroxy-3-methylbutyramide provided N-cyclopropyl-3-{3-cyclopropylmethanesulfonyl-2(R)-[2,2,2-trifluoro-1(S)-(4-fluorophenyl)ethylamino]propionylamino}-3-methyl-2-oxo-butyramide. MS (536.0 M+1, 534.2 M−1).

Example 4

Synthesis of 3(S)-[3-cyclopropylmethanesulfonyl-2(R)-(2,2,3,3,3-pentafluoropropylamino)-propionylamino]-2-oxo-pentanoic acid cyclopropylamide

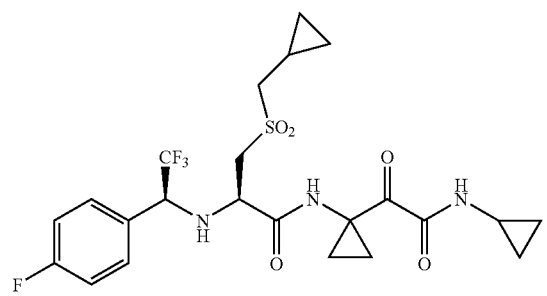

Step 1

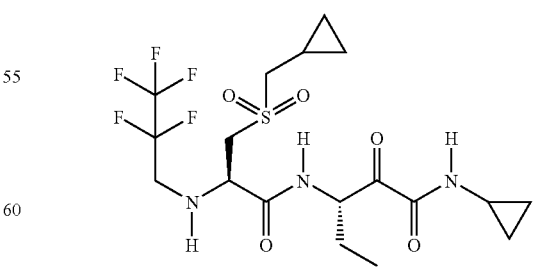

Step 1

To a −78° C. dichloromethane solution (75 mL) of 2,2,3,3,3-pentafluoropentan-1-ol (1.5 g, 10.0 mmol) and DIPEA (6.1 mL, 35.0 mmol) was added triflic anhydride (1.78 mL, 10.5 mmol) dropwise. After 2 h and 20 min, S-trityl cysteine was added to the reaction and stirring continued for 1 h and 15 min at ° C. and then 19 h at room temperature. The reaction mixture was concentrated on the rotovap and the residue was subjected to flash chromatography (3:1, hexanes/ethyl acetate with 1% acetic acid) to provide 2(R)-(2,2,3,3,3-pentafluoropropylamino)-3-tritylsulfanylpropionic acid (3.29 g).

Step 2

To a dichloromethane solution of 2(R)-(2,2,3,3,3-pentafluoropropylamino)-3-tritylsulfanylpropionic acid (1.05 g, 2.12 mmol) was added TFA (0.653 mL, 8.48 mmol) followed by triethylsilane (0.677 mL, 4.24 mmol). The reaction mixture was stirred for 1 h and 20 min at room temperature and then concentrated on the rotovap. To the residue was added 2N NaOH and hexanes. The mixture was shaken and the NaOH layer separated. To the NaOH layer was added cyclopropylmethyl bromide (0.206 mL, 2.12 mmol). The reaction mixture was stirred for 17 h at room temperature and then acidified with 1N HCl and the product extracted into ethylacetate. The ethyl acetate layer was washed with brine, dried over magnesium sulfate, filtered and concentrated to provide 2(R)-(2,2,3,3,3-pentafluoropropylamino)-3-(cyclopropylmethanesulfanyl)propionic acid (428 mg).

Step 3

To a mixture of 2(R)-(2,2,3,3,3-pentafluoropropylamino)-3-(cyclopropylmethanesulfanyl)propionic acid (150 mg, 0.49 mmol), 3(S)-amino-4-hydroxy-pentanoic acid cyclopropylamide hydrochloride (102 mg, 0.49 mmol), EDC (114 mg, 0.74 mmol) and HOBt (79 mg, 0.59 mmol) in dichlormethane was added N-methylmorpholine (0.215 mL, 1.96 mmol). The reaction mixture was stirred for 2 h at room temperature and then diluted with ethylacetate and washed with sodium bicarbonate solution. The organic layer was dried and concentrated to provide 2-hydroxy-3(S)-[2(R)-(2,2,3,3,3-pentafluoropropylamino)-3-(cyclopropylmethanesulfanyl)propionylamino]pentanoic acid cyclopropylamide (169 mg).

Step 4

To an NMP solution (5 mL) of 2-hydroxy-3(S)-[2(R)-(2,2,3,3,3-pentafluoropropylamino)-3-(cyclopropylmethanesulfanyl)propionylamino]pentanoic acid cyclopropylamide (169 mg, 0.37 mmol) was added an aqueous solution(5 mL) of OXONE (342 mg, 0.56 mmol). After stirring for 2 h at room temperature more aqueous OXONE (228 mg) was added along with methanol (5 mL). After stirring for additional 2 h the reaction was diluted with ethylacetate and washed with a sat'd brine solution. The organic layer was separated, dried and concentrated to provide a white solid to which was added dichloromethane (10 mL) and Dess-Martin periodane. To this heterogeneous mixture was added acetonitrile (3 mL) followed by NMP (6 mL) which provided a homogeneous reaction. After 5 h, the reaction was diluted with ethylacetate and washed with sodium bicarbonate solution. The organic layer was dried and concentrated to provide the crude product as a white solid. To this white solid was added ethanol and the mixture was heated to reflux. The still heterogeneous mixture was allowed to cool to room temperature and was filtered to provide the title compound as a white solid (115 mg). M. pt 196.1-196.7° C.

Proceeding as above the following compounds were prepared:

N-cyclopropyl-3S-{3-benzenesulfonyl-2R-[2,2,2-trifluoro-1S-(4-fluoro-phenyl)-ethylamino]-propionylamino}-2-oxo-pentanamide, LC-MS 558(M+H); and N-cyclopropyl-3S-[3-cyclopropylmethanesulfonyl-2R-(2,2,3,3,4,4,4-heptafluorobutylamino)-propionylamino]-2-oxo-pentanamide, LC-MS 542(M+H).

Example 5

Synthesis of N-cyclopropyl-3S-{4-methanesulfonyl-2S-[2,2,2-trifluoro-1S-(4-fluoro-phenyl)-ethylamino]-butyrylamino}-2-oxo-pentanamide

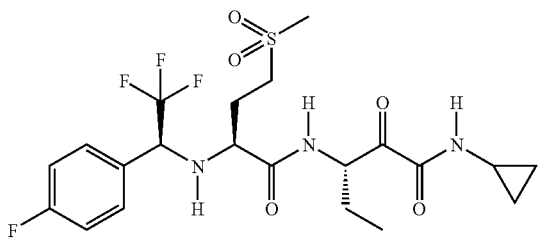

(S)Methyl 2-amino-4-methylsulfanylbutyrate hydrochloride (750 mg, 3.76 mmol) and 2,2,2-trifluoro-1-(4-fluorophenyl)-ethanone (721 mg, 3.76 mmol) was dissolved in methanol (15 mL) and then potassium carbonate (1.04 g, 7.52 mmol) was added to the solution. The mixture was stirred at 55° C. for 23 hours and then concentrated to dryness on a rotovap. The residue was combined with toluene (20 mL) and the mixture was concentrated to dryness on a rotovap. The residue was combined with acetonitrile (10 mL) and the mixture was stirred at approximately −30° C. Zinc borohydride, prepared by adding a 1M zinc chloride solution in ether (5.64 mL) to a mixture of sodium borohydride (427 mg, 11.28 mmol) stirring in ether (10 mL) and then stirring this mixture 19 hours, was added and the reaction stirred for approximately 7 hours at reduced temperature and then an additional 16 hours at room temperature. The reaction mixture was quenched with 1N HCl, diluted with ethyl acetate, and washed with brine (2×50 mL). The organic layer was dried and concentrated to provide 2S-[2,2,2-trifluoro-1S-(4-fluorophenyl)ethylamino]-4-methylsulfanylbutyric acid (1.15 g) as solid.

2S-[2,2,2-Trifluoro-1S-(4-fluorophenyl)ethylamino]-4-methylsulfanylbutyric acid (150 mg, 0.46 mmol), cyclopropyl 3S-amino-2-hydroxypentanamide hydrochloride (106 mg, 0.51 mmol), EDC (132 mg, 0.69 mmol) and HOBt (75 mg, 0.55 mmol) were combined in DCM (10 mL) and the mixture was stirred at room temperature while N-methylmorpholine (0.253 mL, 2.3 mmol) was added. The mixture was stirred for 2 hours and 15 minutes and then diluted with ethyl acetate. The mixture was washed with sodium bicarbonate solution (2×35 mL) and the he organic layer was dried and concentrated to provide N-cyclopropyl-2-hydroxy-3S-{4-methanesulfonyl-2S-[2,2,2-trifluoro-1S-(4-fluoro-phenyl)-ethylamino]-butyrylamino}-pentanamide (188 mg) as a white solid.

N-Cyclopropyl-2-hydroxy-3S-{4-methanesulfonyl-2S-[2,2,2-trifluoro-1S-(4-fluoro-phenyl)-ethylamino]-butyrylamino}-pentanamide (188 mg, 0.39 mmol) was dissolved in 1-methyl-2-pyrrolidinone (5 mL) and the solution was stirred at room temperature while an aqueous solution of oxone (5 mL, 434 mg, 0.71 mmol) was added. The mixture was stirred for 1 hour and 45 minutes and then diluted with ethyl acetate. The mixture was washed with brine (3×25 mL) and the organic layer was dried and concentrated. The residue was dissolved in 1-methyl-2-pyrrolidinone (5 mL) and then Dess-Martin (232 mg, 0.55 mmol) was added to the solution. The reaction was allowed to proceed for 1 hour and then the solution was diluted with ethyl acetate. The mixture was washed with sodium bicarbonate solution (3×30 mL) and the organic layer was dried and concentrated. The residue was combine with ether was added to the solid. The mixture was scraped and filtered to provide N-cyclopropyl-3S-{4-methanesulfonyl-2S-[2,2,2-trifluoro-1S-(4-fluoro-phenyl)-ethylamino]-butyrylamino}-2-oxo-pentanamide (114 mg) as a white solid (mp 152.5-153.5° C.). LC-MS 510(M+H).

BIOLOGICAL EXAMPLES

Example 1

Cathepsin B Assay

Solutions of test compounds in varying concentrations were prepared in 10 μL of dimethyl sulfoxide (DMSO) and then diluted into assay buffer (40 μL, comprising: N,N-bis(2-hydroxyethyl)-2-aminoethanesulfonic acid (BES), 50 mM (pH 6); polyoxyethylenesorbitan monolaurate, 0.05%; and dithiothreitol (DTT), 2.5 mM). Human cathepsin B (0.025 pMoles in 25 μL of assay buffer) was added to the dilutions. The assay solutions were mixed for 5-10 seconds on a shaker plate, covered and incubated for 30 min at room temperature. Z-FR-AMC (20 nMoles in 25 μL of assay buffer) was added to the assay solutions and hydrolysis was followed spectrophotometrically at (λ 460 nm) for 5 min. Apparent inhibition constants ($K_i$) were calculated from the enzyme progress curves using standard mathematical models.

Compounds of the invention were tested by the above-described assay and observed to exhibit cathepsin B inhibitory activity.

Example 2

Cathepsin K Assay

Solutions of test compounds in varying concentrations were prepared in 10 μL of dimethyl sulfoxide (DMSO) and then diluted into assay buffer (40 μL, comprising: MES, 50 mM (pH 5.5); EDTA, 2.5 mM; and DTT, 2.5 mM). Human cathepsin K (0.0906 pMoles in 25 μL of assay buffer) was added to the dilutions. The assay solutions were mixed for 5-10 seconds on a shaker plate, covered and incubated for 30 min at room temperature. Z-Phe-Arg-AMC (4 nMoles in 25 μL of assay buffer) was added to the assay solutions and hydrolysis was followed spectrophotometrically at (λ 460 nm) for 5 min. Apparent inhibition constants ($K_i$) were calculated from the enzyme progress curves using standard mathematical models.

Compounds of the invention were tested by the above-described assay and observed to exhibit cathepsin K inhibitory activity.

Example 3

Cathepsin L Assay

Solutions of test compounds in varying concentrations were prepared in 10 μL of dimethyl sulfoxide (DMSO) and then diluted into assay buffer (40 μL, comprising: MES, 50 mM (pH 5.5); EDTA, 2.5 mM; and DTT, 2.5 mM). Human cathepsin L (0.05 pMoles in 25 μL of assay buffer) was added to the dilutions. The assay solutions were mixed for 5-10 seconds on a shaker plate, covered and incubated for 30 min at room temperature. Z-Phe-Arg-AMC (1 nMoles in 25 μL of assay buffer) was added to the assay solutions and hydrolysis was followed spectrophotometrically at (λ 460 nm) for 5 min. Apparent inhibition constants ($K_i$) were calculated from the enzyme progress curves using standard mathematical models.

Compounds of the invention were tested by the above-described assay and observed to exhibit cathepsin L inhibitory activity.

Example 4

Cathepsin S Assay

Solutions of test compounds in varying concentrations were prepared in 10 μL of dimethyl sulfoxide (DMSO) and then diluted into assay buffer (40 μL, comprising: MES, 50 mM (pH 6.5); EDTA, 2.5 mM; and NaCl, 100 mM); β-mercaptoethanol, 2.5 mM; and BSA, 0.00%. Human cathepsin S (0.05 pMoles in 25 μL of assay buffer) was added to the dilutions. The assay solutions were mixed for 5-10 seconds on a shaker plate, covered and incubated for 30 min at room temperature. Z-Val-Val-Arg-AMC (4 nMoles in 25 μL of assay buffer containing 10% DMSO) was added to the assay solutions and hydrolysis was followed spectrophotometrically (at λ 460 mn) for 5 min. Apparent inhibition constants ($K_i$) were calculated from the enzyme progress curves using standard mathematical models.

Compounds of the invention were tested by the above-described assay and observed to exhibit cathepsin S inhibitory activity of <or =100 nm.

Example 5

Cathepsin F Assay

Solutions of test compounds in varying concentrations were prepared in 10 μL of dimethyl sulfoxide (DMSO) and then diluted into assay buffer (40 μL, comprising: MES, 50 mM (pH 6.5); EDTA, 2.5 mM; and NaCl, 100 mM); DTT, 2.5 mM; and BSA, 0.01%. Human cathepsin F (0.1 pMoles in 25 μL of assay buffer) was added to the dilutions. The assay solutions were mixed for 5-10 seconds on a shaker plate, covered and incubated for 30 min at room temperature. Z-Phe-Arg-AMC (2 nMoles in 25 μL of assay buffer containing 10% DMSO) was added to the assay solutions and hydrolysis was followed spectrophotometrically (at λ 460 nm) for 5 min. Apparent inhibition constants ($K_i$) were calculated from the enzyme progress curves using standard mathematical models.

Compounds of the invention were tested by the above-described assay and observed to exhibit cathepsin F inhibitory activity.

Example 1

Representative pharmaceutical formulations Containing a Compound of Formula (I)

| ORAL FORMULATION | |
| --- | --- |
| Compound of Formula (I) | 10-100 mg |
| Citric Acid Monohydrate | 105 mg |
| Sodium Hydroxide | 18 mg |

-continued

ORAL FORMULATION

| | |
|---|---|
| Flavoring | |
| Water | q.s. to 100 mL |

INTRAVENOUS FORMULATION

| | |
|---|---|
| Compound of Formula (I) | 0.1-10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

TABLET FORMULATION

| | |
|---|---|
| Compound of Formula (I) | 1% |
| Microcrystalline Cellulose | 73% |
| Stearic Acid | 25% |
| Colloidal Silica | 1% |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

What is claimed is:

1. A compound of Formula ():.

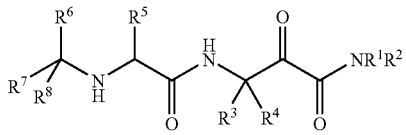

where:

$R^1$ is hydrogen or alkyl;

$R^2$ is cycloalkyl, cycloalkylalkyl, aralkyl, heteroaryl, or heteroaralkyl optionally substituted with one or two substitutents independently selected from alkyl, alkoxy, or halo;

$R^3$ is alkyl or alkoxyalkyl;

$R^4$ is hydrogen or alkyl; or $R^3$ and $R^4$ together with the carbon atom to which they are attached form cycloalkylene optionally substituted with one to four halo or heterocycloalkylene optionally substituted with alkyl, alkoxyalkyl, hydroxyalkyl, acyl, cycloalkyl, cycloalkylalkyl, or haloalkyl;

$R^5$ is alkyl, haloalkyl optionally substituted with cycloalkyl, aryl, heteroaryl, heterocycloalkyl, cycloalkylalkyl, aralkyl, heteroaralkyl, heterocycloalkylalkyl, -(alkylene)-X—$R^9$ (where X is —O—, —S—, —SO—, —SO$_2$—, —CONH—, —NHCO—, or —NHSO$_2$— and $R^9$ is alkyl, haloalkyl, cycloalkylalkyl, aryl, aralkyl, heteroaryl, heteroaralkyl, heterocycloalkyl, or heterocycloalkylalkyl), or -(alkylene)-$X^1$-(haloalkylene)-$R^{10}$ (where $X^1$ is —O—, —S—, —SO—, —SO$_2$—, —CONH—, —NHCO—, or —NHSO$_2$— and $R_{10}$ is cycloalkyl, aryl, heteroaryl, or heterocycloalkyl), wherein the aromatic or alicyclic ring in $R^5$ is optionally substituted with one, two, or three $R^a$ independently selected from alkyl, haloalkyl, alkoxy, hydroxy, haloalkoxy, cyano, or halo; optionally substituted with one or two $R^b$ independently selected from hydrogen, alkyl, haloalkyl, alkoxy, hydroxy, haloalkoxy, halo, carboxy, or alkoxycarbonyl and one $R^c$ selected from cyano, hydroxyalkyl, alkoxyalkyl, aminoalkyl, aryl, heteroaryl, aralkyl, heteroaralkyl, cycloalkyl, cycloalkylalkyl, heterocycloalkyl, heterocycloalkylalkyl, acyl, acylalkyl, alkoxycarbonyl, aryloxycarbonyl, aralkyloxycarbonyl, heteroaryloxycarbonyl, heteroaralkyloxycarbonyl, heterocycloalkyloxycarbonyl, cycloalkyloxycarbonyl, aryloxy, heteroaryloxy, aralkyloxy, heteroaralkyloxy, aminocarbonyl, aminosulfonyl, or —SO$_2$R$^{11}$ (where R$^{11}$ is alkyl, aryl, heteroaryl, or heterocycloalkyl); and further wherein the aromatic or alicyclic ring in $R^c$ is optionally substituted with one, two, or three $R^d$ independently selected from alkyl, haloalkyl, alkoxy, hydroxy, haloalkoxy, or halo;

$R^6$ is haloalkyl;

$R^7$ is hydrogen or haloalkyl; and $R^8$ is hydrogen, alkyl, haloalkyl, cycloalkyl, aryl, heteroaryl, heterocycloalkyl attached via a carbon atom wherein the aromatic or alicyclic ring in $R^8$ is optionally substituted with one, two, or three $R^e$ independently selected from alkyl, halo, haloalkyl, hydroxy, alkoxy, haloalkoxy, alkoxycarbonyl, carboxy, cyano, alkylsulfonyl, or aminosulfonyl; or a pharmaceutically acceptable salts thereof.

2. The compound of claim 1 wherein $R^1$ is hydrogen and $R^2$ is cyclopropyl, 1-phenylethyl, or 1H-pyrazol-5-yl.

3. The compound of claim 1 wherein $R^1$ is hydrogen and $R^2$ is cyclopropyl.

4. The compound of claim 2 or 3 wherein $R^3$ is hydrogen and $R^4$ is alkyl.

5. The compound of claim 2 or 3 wherein $R^3$ is hydrogen and $R^4$ is methyl, ethyl, propyl or butyl.

6. The compound of claim 2 or 3 wherein $R^3$ is hydrogen and $R^4$ ethyl.

7. The compound of claim 2 or 3 wherein $R^3$ and $R^4$ are alkyl.

8. The compound of claim 2 or 3 wherein $R^3$ and $R^4$ are independently methyl or ethyl.

9. The compound of claim 2 or 3 wherein $R^3$ and $R^4$ are methyl.

10. The compound of claim 2 or 3 wherein $R^3$ and $R^4$ together with the carbon atom to which they are attached form cycloalkylene.

11. The compound of claim 2 or 3 wherein $R^3$ and $R^4$ together with the carbon atom to which they are attached form cyclopropylene.

12. The compound of any of the claims 2-11 wherein $R^6$ is haloalkyl and $R^7$ and $R^8$ are hydrogen.

13. The compound of any of the claims 2-11 wherein $R^6$ is 2,2,2-trifluoroethyl or 1,1,2,2,2-pentafluoroethyl and $R^7$ and $R^8$ are hydrogen.

14. The compound of any of the claims 2-11 wherein $R^6$ is haloalkyl, $R^7$ is haloalkyl, and $R^8$ is hydrogen.

15. The compound of any of the claims 2-11 wherein $R^6$ is haloalkyl, $R^7$ is alkyl, and $R^8$ is hydrogen.

16. The compound of any of the claims 2-11 wherein $R^6$ is haloalkyl, $R^7$ is hydrogen, and $R^8$ is aryl optionally substituted with one, two, or three $R^e$.

17. The compound of any of the claims 2-11 wherein $R^6$ is trifluoromethyl or difluoromethyl, $R^7$ is hydrogen, and $R^8$ is 4-fluorophenyl, 2,3-, 2,4-, 2,5-, 2,6-, 3,4, or 3,5-difluorophenyl.

18. The compound of any of the claims 2-11 wherein $R^6$ is haloalkyl, $R^7$ is hydrogen, and $R^8$ and $R^8$ is heteroaryl optionally substituted with one, two, or three $R^e$.

19. The compound of any of the claims 2-18 wherein $R^5$ is cycloalkylalkyl optionally substituted with one, two, or three $R^a$ independently selected from alkyl or halo or an $R^c$ selected from aralkyl or heteroaralkyl.

20. The compound of any of the claims 2-18 wherein $R^5$ is 1-methylcyclopentylmethyl, 1-methylcyclohexyl, 1-methylcyclobutyl, 1-methyl-3,3-difluorocyclobutylmethyl, 1-methyl-4,4-difluorocyclohexylmethyl, 1-benzyl-cyclopropylmethyl, 1-thiazol-2-ylmethylcyclopropyl-methyl, or 1-methyl-3,3-difluorocyclopentylmethyl.

21. The compound of any of the claims 2-18 wherein $R^5$ is alkyl.

22. The compound of any of the claims 2-18 wherein $R^5$ is haloalkyl substituted with aryl, heteroaryl or heterocycloalkyl.

23. The compound of any of the claims 2-18 wherein $R^5$ is 2,2-difluoro-3-phenylpropyl, 2,2-difluoro-3-tetrahydropyran-4-ylpropyl, 2,2-difluoro-3-morpholin-1-ylpropyl, 2,2-difluoro-3-pyridin-2-ylpropyl, 2,2-difluoro-3-pyridin-3-ylpropyl, or 2,2-dichloro-3-phenylpropyl.

24. The compound of any of the claims 2-18 wherein $R^5$ is -(alkylene)-S(O)$_2$—$R^9$ where $R^9$ is alkyl.

25. The compound of any of the claims 2-18 wherein $R^5$ is methylsulfonylmethyl, ethylsulfonylmethyl, propyl-1-sulfonylmethyl, 2-methylpropylsulfonylmethyl, 2-methysulfonylethyl, or 2-ethylsulfonylethyl.

26. The compound of any of the claims 2-18 wherein $R^5$ is -(alkylene)-S(O)$_2$—$R^9$ where $R^9$ is is aryl or aralkyl optionally substituted with one, two, or three $R^a$ independently selected from alkyl, haloalkyl, alkoxy, hydroxy, haloalkoxy, cyano, or halo; or optionally substituted with one or two $R^b$ independently selected from hydrogen, alkyl, haloalkyl, alkoxy, hydroxy, haloalkoxy, halo, carboxy, or alkoxycarbonyl and one $R^c$ selected from hydroxyalkyl, alkoxyalkyl, aminoalkyl, aryl, heteroaryl, aralkyl, heteroaralkyl, cycloalkyl, cycloalkylalkyl, heterocycloalkyl, heterocycloalkylalkyl, acyl, alkoxycarbonyl, aryloxycarbonyl, aralkyloxycarbonyl, heteroaryloxycarbonyl, heteroaralkyloxycarbonyl, aryloxy, heteroaryloxy, aralkyloxy, heteroaralkyloxy, aminocarbonyl, aminosulfonyl, or —SO$_2$R$^{11}$ (where R$^{11}$ is alkyl, aryl, heteroaryl, or heterocycloalkyl); and further wherein the aromatic or alicyclic ring in R$^c$ is optionally substituted with one, two, or three $R^d$ independently selected from alkyl, haloalkyl, alkoxy, hydroxy, haloalkoxy, or halo.

27. The compound of any of the claims 2-18 wherein $R^5$ is 2-difluoromethoxyphenyl-methanesulfonylmethyl, 2-phenylsulfonylethyl, 4-fluorophenylmethanesulfonylmethyl, 4-aminocarbonylphenylmethanesulfonylmethyl, 4-piperazin-1-ylphenylmethanesulfonylmethyl, 2-fluorophenyl-methanesulfonylmethyl, 3-fluorophenylmethanesulfonyl-methyl, 2,4,6-trifluorophenylmethanesulfonylmethyl, 2-, 3-, or 4-trifluoromethylphenylmethanesulfonyl-methyl, phenyl-methanesulfonylmethyl, 2-(2-, 3-, or 4-trifluoromethylphenyl)sulfonylethyl, phenylmethanesulfonylmethyl, or 2-(2-, 3-, or 4-fluorophenyl)sulfonylethyl.

28. The compound of any of the claims 2-18 wherein $R^5$ is -(alkylene)-S(O)$_2$—$R^9$ where $R^9$ is heteroaryl or heteroaralkyl optionally substituted with one, two, or three $R^a$ independently selected from alkyl, haloalkyl, alkoxy, hydroxy, haloalkoxy, cyano, or halo; or optionally substituted with one or two $R^b$ independently selected from hydrogen, alkyl, haloalkyl, alkoxy, hydroxy, halo alkoxy, halo, carboxy, or alkoxycarbonyl and one $R^c$ selected from hydroxyalkyl, alkoxyalkyl, aminoalkyl, aryl, heteroaryl, aralkyl, heteroaralkyl, cycloalkyl, cycloalkylalkyl, heterocycloalkyl, heterocycloalkylalkyl, acyl, alkoxycarbonyl, aryloxycarbonyl, aralkyloxycarbonyl, heteroaryloxycarbonyl, heteroaralkyloxycarbonyl, aryloxy, heteroaryloxy, aralkyloxy, heteroaralkyloxy, aminocarbonyl, aminosulfonyl, or —SO$_2$R$^{11}$ (where R$^{11}$ is alkyl, aryl, heteroaryl, or heterocycloalkyl); and further wherein the aromatic or alicyclic ring in R$^c$ is optionally substituted with one, two, or three R$^d$ independently selected from alkyl, haloalkyl, alkoxy, hydroxy, haloalkoxy, or halo.

29. The compound of any of the claims 2-18 wherein $R^5$ is pyridin-2-ylmethanesulfonyl-methyl, pyridin-3-ylmethanesulfonylmethyl, pyridin-4-ylmethanesulfonylmethyl, 3-difluoro-methoxypyridin-2-ylmethanesulfonylmethyl, 2-difluoromethoxypyridin-3-ylmethane-sulfonylmethyl, 4-difluoromethoxypyridin-3-ylmethanesulfonylmethyl, 3-difluoromethoxy-pyridin-4-ylmethanesulfonylmethyl, pyrimidin-2-ylmethanesulfonylmethyl, pyrimidin-5-yl-methanesulfonylmethyl, 3-trifluoromethylpyridin-2-yl-methanesulfonylmethyl, 4-trifluoromethylpyridin-3-yl-methanesulfonylmethyl, 3,5-dimethylisoxazol-4-ylmethane-sulfonylmethyl, 2-fluorofuran-5-ylmethanesulfonylmethyl, 2-methylthiazol-4-ylmethane-sulfonylmethyl, furan-2-yl-methanesulfonylmethyl, 2-pyridin-2-ylethanesulfonylmethyl, 2-pyridin-3-ylethanesulfonylmethyl, 2-pyridin-4-ylethanesulfonylmethyl, 2-pyridin-3-yl-sulfonylethyl, 2-pyridin-4-ylsulfonylethyl, 3-pyridin-3-ylsulfonylpropyl, 1,3,5-triazin-2-yl-methanesulfonylmethyl, 1,3,4-thiadiazol-2-ylmethanesulfonylmethyl, oxazol-5-yl-methanesulfonylmethyl, thiazol-5-ylmethanesulfonylmethyl, or thiazol-2-yl-methane-sulfonylmethyl.

30. The compound of any of the claims 2-18 wherein $R^5$ is -(alkylene)-S(O)$_2$—$R^9$ where $R^9$ is cycloalkylalkyl.

31. The compound of any of the claims 2-18 wherein $R^5$ is cyclopropylmethanesulfonylmethyl.

32. A pharmaceutical composition comprising a compound of any of the claims 1-31 in admixture with one or more suitable excipients.

33. The compound of claim 1 wherein:
$R^3$ is alkyl and $R^4$ is alkyl.

34. The compound of claim 1 wherein:
$R^3$ and $R^4$ together with the carbon atom to which they are attached form cycloalkylene.

35. The compound of claim 1 wherein:
$R^3$ and $R^4$ together with the carbon atom to which they are attached form piperidin-4-yl substituted at the nitrogen atom with ethyl, 2,2,2-trifluoroethyl or cyclopropyl, tetrahydropyran-4-yl, tetrahydrothiopyran-4-yl, or 1,1-dioxotetrahydrothiopyran-4-yl.

36. The compound of claim 1 wherein:
$R^6$ is haloalkyl and $R^7$ and $R^8$ are hydrogen.

37. The compound of claim 1 wherein:
$R^6$ is haloalkyl, $R^7$ is haloalkyl, and $R^8$ are hydrogen.

38. The compound of claim 1 wherein:
$R^6$ is haloalkyl, $R^7$ is alkyl, and $R^8$ are hydrogen.

39. The compound of claim 1 wherein:
$R^1$ is hydrogen, $R^2$ is cyclopropyl, $R^3$ is hydrogen, $R^4$ is ethyl, $R^5$ is 2-methylsulfonylethyl, $R^6$ is trifluoromethyl, $R^7$ is hydrogen and $R^8$ is 4-fluorophenyl, namely N-cyclopropyl-3-{4-methanesulfonyl-2-[2,2,2-trifluoro-1-(4-fluoro-phenyl)-ethylamino]-butyrylamino}-2-oxo-pentanamide.

40. The compound of claim 39 which is N-cyclopropyl-3S-{4-methanesulfonyl-2S-[2,2,2-trifluoro-1S-(4-fluoro-phenyl)-ethylamino]-butyrylamino}-2-oxo-pentanamide.

41. The compound of claim 1 wherein:
$R^1$ is hydrogen, $R^2$ is cyclopropyl, $R^3$ is hydrogen, $R^4$ is ethyl, $R^5$ is 2-phenylsulfonylmethyl, $R^6$ is trifluoromethyl, $R^7$ is hydrogen and $R^8$ is 4-fluorophenyl, namely N-cyclopropyl-3-{3-benzenesulfonyl-2-[2,2,2-trifluoro-1-(4-fluoro-phenyl)-ethylamino]-propionylamino}-2-oxo-pentanamide.

42. The compound of claim 41 which is N-cyclopropyl-3S-{3-benzenesulfonyl-2R-[2,2,2-trifluoro-1S-(4-fluoro-phenyl)-ethylamino]-propionylamino}-2-oxo-pentanamide.

43. The compound of claim 1 wherein:
$R^1$ is hydrogen, $R^2$ is cyclopropyl, $R^3$ is hydrogen, $R^4$ is ethyl, $R^5$ is cyclopropylmethylsulfonylmethyl, $R^6$ is perfluoropropyl, $R^7$ is hydrogen and $R^8$ is hydrogen, namely N-cyclopropyl-3-[3-cyclopropylmethanesulfonyl-2-(2,2,3,3,4,4,4-heptafluoro-butylamino)-propionylamino]-2-oxo-pentanamide.

44. The compound of claim 43 which is N-cyclopropyl-3S-[3-cyclopropylmethanesulfonyl-2R-(2,2,3,3,4,4,4-heptafluoro-butylamino)-propionylamino]-2-oxo-pentanamide.

* * * * *

UNITED STATES PATENT AND TRADEMARK OFFICE
CERTIFICATE OF CORRECTION

PATENT NO. : 7,488,848 B2
APPLICATION NO. : 11/384023
DATED : February 10, 2009
INVENTOR(S) : Michael Graupe, John O. Link and Michael G. Roepel It is certified that error appears in the above-identified patent and that said Letters Patent is hereby corrected as shown below:

Claim 1, Column 55, lines 39-47:

"1. A compound of Formula ():

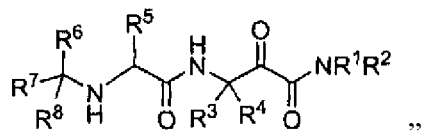

,, should read:

-- 1. A compound of Formula (I):

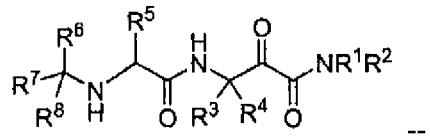

--

Claim 1, Column 56, line 5:

"–NHSO$_2$– and R$_{10}$ is cycloalkyl, aryl, heteroaryl, or"

Should read:

-- –NHSO$_2$– and R$^{10}$ is cycloalkyl, aryl, heteroaryl, or --

Signed and Sealed this

Twenty-sixth Day of May, 2009

JOHN DOLL
*Acting Director of the United States Patent and Trademark Office*